United States Patent
Lamarque et al.

(10) Patent No.: US 11,993,618 B2
(45) Date of Patent: May 28, 2024

(54) WATER SOLUBLE MONO-BRANCHED AND DI-BRANCHED COMPLEXING AGENTS, AND CORRESPONDING LANTHANIDE COMPLEXES

(71) Applicant: CISBIO BIOASSAYS, Codolet (FR)

(72) Inventors: Laurent Lamarque, Saint-Victor la Coste (FR); Jurriaan Zwier, Rochefort-du-Gard (FR); Emmanuel Bourrier, Bagnols-sur-Ceze (FR)

(73) Assignee: CISBIO BIOASSAYS, Codolet (FR)

( * ) Notice: Subject to any disclaimer, the term of this patent is extended or adjusted under 35 U.S.C. 154(b) by 1202 days.

(21) Appl. No.: 16/622,123

(22) PCT Filed: Jun. 11, 2018

(86) PCT No.: PCT/FR2018/051354
§ 371 (c)(1),
(2) Date: Dec. 12, 2019

(87) PCT Pub. No.: WO2018/229408
PCT Pub. Date: Dec. 20, 2018

(65) Prior Publication Data
US 2023/0017272 A1    Jan. 19, 2023

(30) Foreign Application Priority Data
Jun. 12, 2017 (FR) .................... 1755214

(51) Int. Cl.
C07D 401/14 (2006.01)
C07F 5/00 (2006.01)
(52) U.S. Cl.
CPC ............ C07F 5/003 (2013.01); C07D 401/14 (2013.01)

(58) Field of Classification Search
CPC .................................................. C07D 401/14
See application file for complete search history.

(56) References Cited

FOREIGN PATENT DOCUMENTS

| WO | 2013011236 A1 | 1/2013 |
| WO | 2014147288 A1 | 9/2014 |
| WO | 2014162105 A1 | 10/2014 |
| WO | 2016066641 A1 | 5/2016 |

OTHER PUBLICATIONS

English Translation of International Search Report from PCT/FR2018/051354 dated Aug. 10, 2018 (3 pages).
Matthieu Starck et al: Structural Control of Cell Permeability with Highly Emissive Europium( I I I) Complexes Permits Different—Microscopy Applications11 , Chemistry a European Journal, vol. 22, No. 2, Jan. 11, 2016 (Jan. 11, 2016), pp. 570-580, XP055434704.

*Primary Examiner* — Brian E McDowell
(74) *Attorney, Agent, or Firm* — Calfee, Halter & Griswold LLP

(57) ABSTRACT

The invention relates to complexing agents of formula (I):

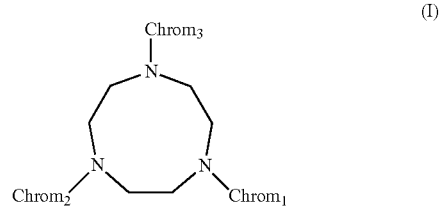

wherein $Chrom_1$, $Chrom_2$ and $Chrom_3$ are as defined in the description. The invention also relates to lanthanide complexes obtained from these complexing agents.

13 Claims, 5 Drawing Sheets

WATER SOLUBLE MONO-BRANCHED AND DI-BRANCHED COMPLEXING AGENTS, AND CORRESPONDING LANTHANIDE COMPLEXES

The present invention relates to water-soluble complexing agents or ligands, to lanthanide complexes obtained from these complexing agents, and to the use of these lanthanide complexes to label molecules and detect them by time-resolved fluorescence techniques.

STATE OF THE ART

The use of lanthanide complexes has greatly expanded in the last twenty years in the field of life sciences. The reason for this is that these fluorescent compounds have advantageous spectroscopic characteristics, which make them labels of choice for detecting biological molecules. These fluorescent compounds are particularly suitable for use in conjunction with compatible fluorophores for performing Forster resonance energy transfer (FRET) measurements, whose application for studying interactions between biomolecules is commercially exploited by several companies, including Cisbio Bioassays and its range of HTRF® products. The relatively long lifetime of lanthanide complexes also makes it possible to perform time-resolved fluorescence measurements, i.e. with a delay after excitation of the fluorophores, which makes it possible to limit fluorescence interferences due to the measuring medium. The latter feature is all the more useful when the measuring medium tends toward a biological medium, which comprises numerous proteins whose fluorescence might interfere with that of the compounds under study.

Many lanthanide complexes have been described. Latva et al, for example, disclosed 41 Eu(III) and Tb(III) complexes and studied their luminescence (Journal of Luminescence 1997, 75, 149). Compound 39 in particular, consists of a 1,4,7-triazacyclononane ring (hereinafter "TACN"), whose nitrogen atoms are substituted by chromophores derived from phenylethynylpyridine. Although the quantum yield of the complex consisting of this chromophore and Eu(III) is considered good by the authors, this complex is not suitable for coupling with a biomolecule. In addition, the use of this compound in an aqueous medium can be problematic since it is very hydrophobic. Finally, the absorption of this complex is optimal at 315 nm, while the excitation wavelength often used in plate readers for bioassays is rather at 337 nm.

D'Aldo et al have described the synthesis of lanthanide complexes composed of three ligands derived from dipicolonic acid (Inorganic Chemistry 2008, 47, 10258). One of these ligands (L1) consists of a dipicolinic acid molecule substituted by a phenylethynyl group, itself carrying a polyethylene glycol ether-oxide (hereinafter "PEG") on the phenyl group. According to the authors, the PEG group gives this product good solubility in aqueous media and organic solvents. However, these complexes are not sufficiently stable in aqueous media and cannot be used in a bioconjugation reaction.

Several other lanthanide complexes have been disclosed, and some are commercially exploited: particular mention may be made of the macropolycyclic lanthanide cryptates (EP-A-0 180 492; EP-A-0 321 353; EP-A-0 601 113; EP-A-0 601 113; WO 2001/96877; WO 2008/063721), lanthanide complexes containing a coumarin-derived unit linked to a diethylenetriamine penta-acid unit (U.S. Pat. No. 5,622,821), and those containing pyridine derivatives (U.S. Pat. Nos. 4,920,195; 4,761,481), bipyridine derivatives (U.S. Pat. No. 5,216,134), or terpyridine derivatives (U.S. Pat. Nos. 4,859,777; 5,202,423; 5,324,825).

Patent application WO 2013/011236 describes complexing agents of formula:

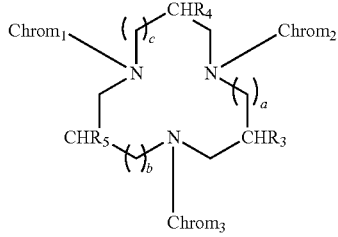

In this application the inventors envisage complexes with three chromophores to increase brightness. In addition, to make these complexes water-soluble, the inventors use PEG groups. Although these PEG groups are neutral from an "overall charge" point of view, they confer adsorption properties on plastic and glass on the complexes, which makes their use in an immunoassay difficult.

Patent application WO 2014/111661 describes complexing agents, comprising three chromophore groups, represented by the formula:

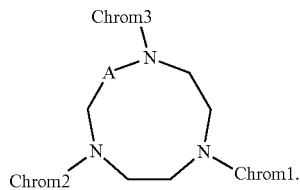

In this application, the inventors replaced the PEG groups with anionic or cationic charged groups. These complexes are perfectly soluble and no longer adsorb onto plastic or glass. These complexes have fairly large star structures and very high brightness properties.

Patent application WO 2014/162105 concerns lanthanide complexes containing at least two betaine groups on the organic part, giving them advantageous properties in terms of solubility in water and biological media. These solubilizing groups are presented as limiting non-specific adsorption phenomena with living cells. On the other hand, these complexes have three identical or different chromophores, which, as in application WO 2014/111661, generate quite large star structures and good brightness properties.

Patent applications WO 2014/147288 and WO 2016/066641 describe TACN complexes with high molar absorption coefficients. These complexes have a high brightness but also have three chromophores. The inventors are looking for the brightest possible complexes in order to have an optimal energy transfer (FRET). The star structures of the complexes are once again voluminous, and their brightness is high.

The introduction of three chromophores on a triazacyclonane macrocycle is not always an advantage since the chromophores are synthons from a long and tedious synthesis. The presence of three chromophores in a TACN complex increases the size of the molecule, which increases steric hindrance with biomolecules. Nevertheless, the higher the number of chromophores, the higher the brightness, since this parameter depends on the quantum yield and the molar absorption coefficient (epsilon) of the molecule. By introducing three chromophores into a molecule, the brightness is increased.

In the present invention we have discovered that there is no correlation between the brightness of a complex and its ability to detect a biological target in an immunoassay based on time-resolved FRET in which the complex is used as an energy donor. This invention aims to overcome the drawbacks of the prior art, i.e. to simplify synthesis by introducing one or two chromophores, to reduce steric hindrance and finally to have a fluorescent probe with at least the same performance in terms of energy transfer.

The present invention therefore aims to provide fluorescent lanthanide complexes with a lower brightness than the compounds of the prior art when excited at about 337 nm but whose ability to detect a biological target in a time-resolved FRET based immunoassay is comparable or better than that of analogues carrying three chromophores. These complexes also have good solubility in aqueous media, an emission spectrum suitable for use in FRET experiments, and good practicality for labelling biomolecules since they are smaller in size.

COMPLEXING AGENTS

Figure 1:
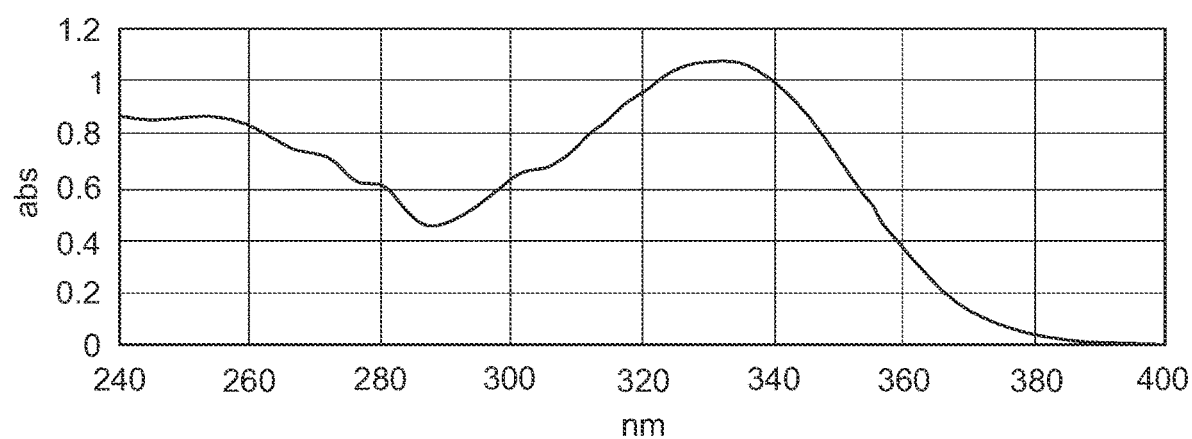
FIGS. 1 to 3 represent respectively the UV spectrum, the chromatogram and the mass spectrum of a complex representative of the invention.

The complexing agents according to the invention are the compounds of formula (I):

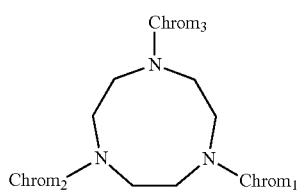
(I)

wherein:

$Chrom_1$, $Chrom_2$ and $Chrom_3$, independently of one another, represent a group of formula:

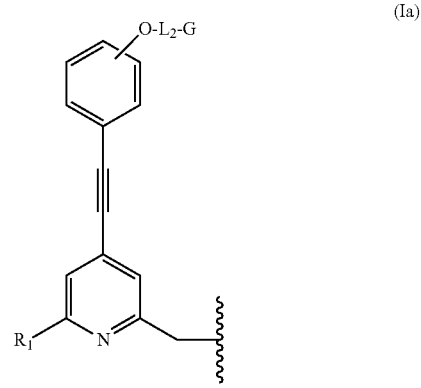
(Ia)

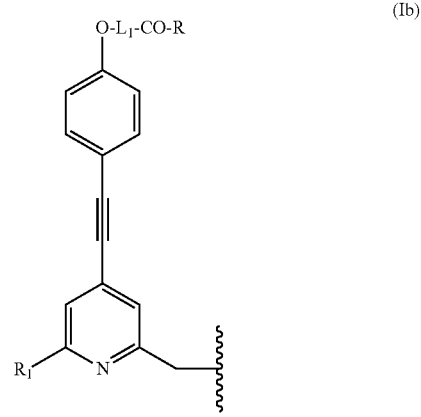
(Ib)

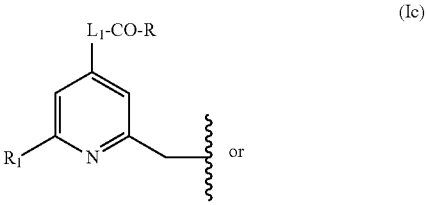
(Ic)

or

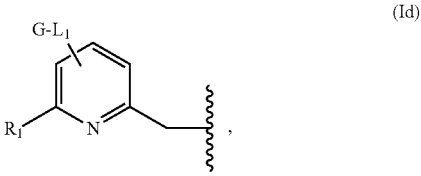
(Id)

provided that the compound of formula (I) (necessarily) comprises (i) one or two groups selected from the groups (Ia) and (Ib) and (ii) at least one $L_1$-CO—R group;

R is a —$OR_2$ or —NH-E group;

$R_1$ is a —$CO_2H$ or —P(O)(OH)$R_3$ group;

$R_2$ is H or a ($C_1$-$C_4$)alkyl;

$R_3$ is a ($C_1$-$C_4$)alkyl, preferably methyl; phenyl optionally substituted by a —$SO_3$— group, the latter preferably in the meta or para position; or benzyl;

$L_1$ is a direct bond; a —$(CH_2)_r$— group optionally interrupted by at least one atom selected from an oxygen atom, a nitrogen atom and a sulphur atom; a —CH=CH— group; a —CH=CH—$CH_2$— group; a —$CH_2$—CH=CH— group; or a PEG group;

$L_2$ is a divalent linking group;

G is a reactive group;

E is a —CH$_2$—(CH$_2$)$_s$—CH$_2$—SO$_3$— or —(CH$_2$)$_s$—N$^+$Alk$_1$Alk$_2$Alk$_3$ group, or a sulfobetaine;

r is an integer from 1 to 6, preferably from 1 to 3;

s is 0, 1 or 2;

Alk$_1$, Alk$_2$, Alk$_3$, which may be identical or different, represent a (C$_1$-C$_6$)alkyl.

The complexing agents according to the invention therefore comprise either one or two groups selected from the groups (Ia) and (Ib) and, consequently, one or two groups selected from the groups (Ic) and (Id)—since the structure of formula (I) comprises three chromophores (Chrom$_1$, Chrom$_2$ and Chrom$_3$). An additional requirement for compounds of formula (I) is that at least one L$_1$-CO—R group must be present in the structure.

PEG group refers to a polyethylene glycol group of formula —CH$_2$—(CH$_2$OCH$_2$)$_y$—CH$_2$OCH$_3$, where y is an integer from 1 to 5.

Sulfobetaine refers to a group selected from:

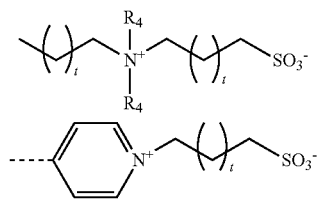

with R$_4$ which represents (C$_1$-C$_6$)alkyl, preferably methyl or ethyl, and t which is equal to 1, 2, 3, 4, 5 or 6, and preferably which is equal to 1 or 2, the sulfobetaine of formula —(CH$_2$)$_2$N$^+$(CH$_3$)$_2$—(CH$_2$)$_3$—SO$_3$— being preferred. Depending on the pH, the —SO$_3$H, —CO$_2$H and —PO(OH)$_2$ groups are in deprotonated form or not. These groups therefore also refer in the following text to the groups —SO$_3$—, —CO$_2$ and —PO(OH)O—, and vice versa.

A first preferred family of complexing agents consists of compounds of formula (I) where Chrom$_1$ is a group of formula (Ia) and Chrom$_2$ and Chrom$_3$ are each a group of formula (Ic), identical or different. In one embodiment, Chrom$_2$ and Chrom$_3$ are identical. In another embodiment, which can be combined with the preceding embodiment, R$_1$ is a —CO$_2$H or —P(O)(OH)R$_3$ group wherein R$_3$ is a (C$_1$-C$_4$)alkyl or phenyl.

A second preferred family of complexing agents consists of compounds of formula (I) where Chrom$_1$ and Chrom$_2$ are each a group of formula (Ib), identical or different, and Chrom$_3$ is a group of formula (Id). In one embodiment, Chrom$_1$ and Chrom$_2$ are identical. In another embodiment, which can be combined with the preceding embodiment, R$_1$ is a —CO$_2$H or —P(O)(OH)R$_3$ group wherein R$_3$ is a (C$_1$-C$_4$)alkyl or phenyl.

Among these two preferred families, preferred sub-families are those where the complexing agents include one or more of the following features:

R$_2$ is H;

L$_1$ is a direct bond; a —(CH$_2$)$_r$— group optionally interrupted by at least one atom selected from an oxygen atom and a sulphur atom, and r=2 or 3; a —CH=CH— group; a —CH=CH—CH$_2$— group; or a —CH$_2$—CH=CH— group;

E is a —CH$_2$—(CH$_2$)$_s$—CH$_2$—SO$_3$— group with s=0 or 1; —(CH$_2$)$_s$—N$^+$Alk$_1$Alk$_2$Alk$_3$ with Alk$_1$, Alk$_2$ Alk$_3$, identical or different, representing (C$_1$-C$_4$)alkyl and s=0 or 1; or a group of formula:

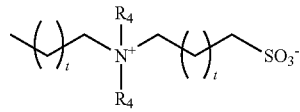

wherein R$_4$ is a (C$_1$-C$_4$)alkyl and t is 1 or 2.

In one embodiment of the invention, when the complexing agents of formula (I) comprise several E groups, at most one of these groups represents a sulfobetaine.

The reactive group G carried by a spacer arm L$_1$ or L$_2$, allows the compounds according to the invention to be coupled with a species that is to be made fluorescent, for example an organic molecule, a peptide or a protein. The techniques for conjugating two organic molecules are based on the use of reactive groups and are part of the general knowledge of the skilled person. These classical techniques are described for example in Bioconjugate Techniques, G. T. Hermanson, Academic Press, Second Edition 2008, pp. 169-211.

Typically, the reactive group is an electrophilic or nucleophilic group that can form a covalent bond when it is respectively in the presence of an appropriate nucleophilic or electrophilic group. The conjugation reaction between a compound according to the invention comprising a reactive group and an organic molecule, a peptide or a protein carrying a functional group results in the formation of a covalent bond comprising one or more atoms of the reactive group.

Preferably, the reactive group G is a group derived from one of the following compounds: an acrylamide, an activated amine (for example cadaverine or ethylenediamine), an activated ester, an aldehyde, an alkyl halide, an anhydride, an aniline, an azide, an aziridine, a carboxylic acid, a diazoalkane, a haloacetamide, a halotriazine, such as monochlorotriazine, dichlorotriazine, a hydrazine (including hydrazides), an imido ester, an isocyanate, an isothiocyanate, a maleimide, a sulfonyl halide, a thiol, a ketone, an amine, an acid halide, a succinimidyl ester, a hydroxysuccinimidyl ester, a hydroxysulfosuccinimidyl ester, an azidonitrophenyl, an azidophenyl, a 3-(2-pyridyldithio)-propionamide, a glyoxal, a triazine, an acetylenic group, and in particular a group selected from the groups of formulae:

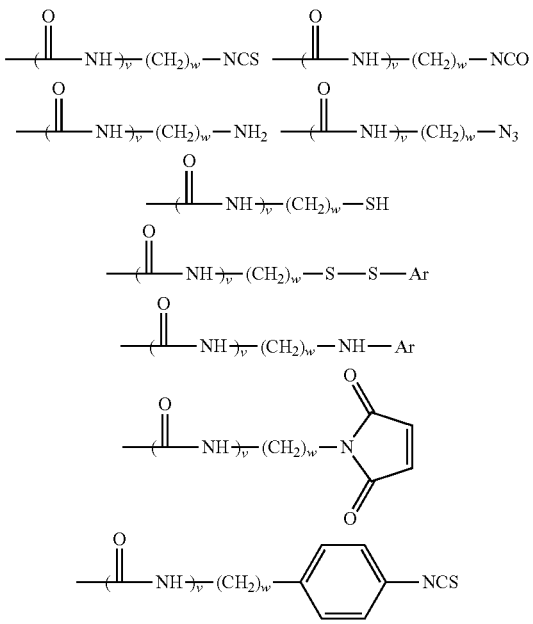

-continued

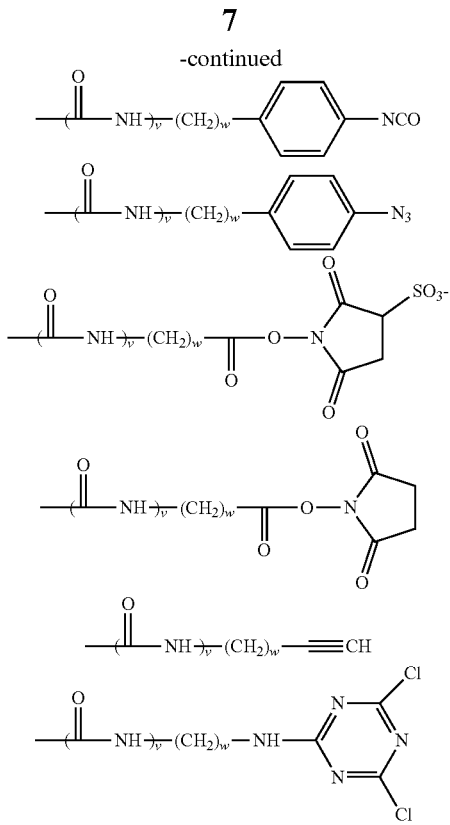

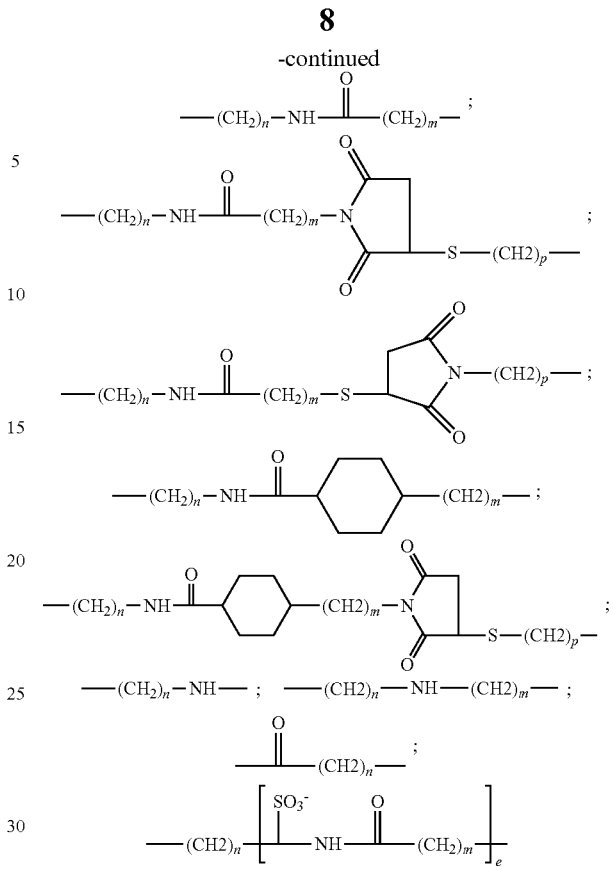

wherein w varies from 0 to 8 and v is equal to 0 or 1, and Ar is a saturated or unsaturated 5- or 6-membered heterocycle, comprising 1 to 3 heteroatoms, optionally substituted by a halogen atom.

Preferably, the reactive group G is an amine (optionally protected in —NHBoc form), a succinimidyl ester, a haloacetamide, a hydrazine, an isothiocyanate, a maleimide group, or a carboxylic acid (optionally protected as a —CO$_2$Me, —CO$_2$tBu group). In the latter case, the acid must be activated as an ester in order to react with a nucleophilic species.

The reactive group G is bound to the complexing agent via a spacer arm $L_1$ or $L_2$, advantageously constituted by a divalent organic radical. In particular, the spacer arm $L_2$ can be selected from:
- a direct bond;
- a linear or branched $C_1$-$C_{20}$, preferably $C_1$-$C_8$, alkylene group optionally containing one or more double or triple bonds;
- a $C_5$-$C_8$ cycloalkylene group; a $C_6$-$C_{14}$ arylene group;
- said alkylene, cycloalkylene or arylene groups optionally containing one or more heteroatoms, such as oxygen, nitrogen, sulphur, phosphorus or one or more carbamoyl or carboxamido groups, and said alkylene, cycloalkylene or arylene groups being optionally substituted by 1 to 5, preferably 1 to 3, $C_1$-$C_8$ alkyl, $C_6$-$C_{14}$ aryl, sulfonate or oxo groups.
- a group selected from divalent groups of the following formulae:

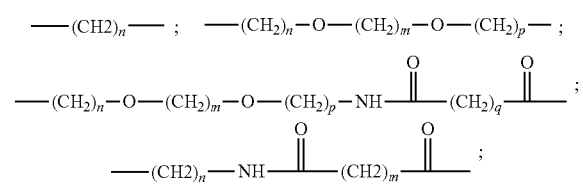

wherein n, m, p, q are integers from 1 to 16, preferably from 1 to 5 and e is an integer from 1 to 6, preferably from 1 to 4.

In groups of formula (Ia), the -$L_2$-G group is preferably composed of a reactive group G selected from: a carboxylic acid (optionally protected in the form of a —CO$_2$Me, —CO$_2$tBu group), an amine (optionally protected in —NHBoc form), a succinimidyl ester, a haloacetamide, a hydrazine, an isothiocyanate, a maleimide group, and a spacer arm $L_2$ consisting of an alkylene chain containing from 1 to 5 carbon atoms or a group selected from the groups of formula:

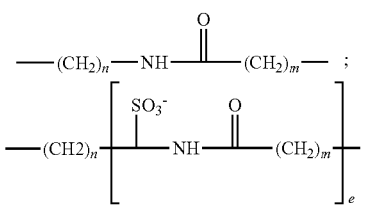

where n, m, are integers from 1 to 16, preferably from 1 to 5 and e is an integer from 1 to 6, preferably from 1 to 4, the group G being linked to either end of these divalent groups.

Complexes

The invention also relates to lanthanide complexes consisting of a lanthanide atom complexed by a complexing agent as described above, the lanthanide being selected from: $Eu^{3+}$, $Sm^{3+}$, $Tb^{3+}$, $Gd^{3+}$, $Dy^{3+}$, $Nd^{3+}$, $Er^{3+}$. The lanthanide is preferably $Tb^{3+}$ or $Eu^{3+}$ and even more preferably $Eu^{3+}$.

These complexes are prepared by reacting the complexing agents according to the invention with a lanthanide salt.

Thus the reaction between one equivalent of complexing agent and 1 to 5 equivalents of lanthanide salt (europium or terbium in the form of chlorides, acetates or triflates) in a solvent (acetonitrile, methanol or other solvent compatible with these salts) or a buffer leads to the corresponding complex after a few minutes of stirring.

As previously mentioned, the fluorescent complexes obtained have excellent photophysical properties, in particular with regard to their quantum yield, their luminescence lifetime and their excitation spectrum, which is particularly suited to laser excitation at about 337 nm or flash lamp. In addition, the distribution of the bands of their emission spectra is centred around 620 nm, thus giving the complexes exceptional and very favourable properties when using FRET with cyanine-type or allophycocyanin-type acceptors (such as XL665 marketed by Cisbio Bioassays). Due to the high stability of these complexes in biological environments containing most of the divalent cations ($Ca^{2+}$, $Mg^{2+}$, etc.) or EDTA, their luminescence remains excellent compared with complexes bearing three chromophores of the prior art.

Conjugates

The complexing agents and lanthanide complexes according to the invention containing a G group are particularly suitable for labelling organic or biological molecules containing a functional group capable of reacting with the reactive group to form a covalent bond. Thus, the invention also relates to the use of lanthanide complexes for labelling molecules of interest (proteins, antibodies, enzymes, hormones etc.).

The invention also relates to molecules labelled with a complex according to the invention. All organic or biological molecules can be conjugated with a complex according to the invention if they have a functional group capable of reacting with the reactive group. In particular, the conjugates according to the invention comprise a complex according to the invention and a molecule selected from: an amino acid, a peptide, a protein, an antibody, a sugar, a carbohydrate chain, a nucleoside, a nucleotide, an oligonucleotide, an enzyme substrate (in particular a suicide enzyme substrate such as benzylguanine or benzylcytosine (enzyme substrates marketed as Snaptag and Cliptag)), a chloroalkane (substrate of the enzyme marketed under the name Halotag), coenzyme A (substrate of the enzyme marketed under the name ACPtag or MCPtag).

Synthesis

The general strategy for the preparation of complexing agents (ligands) and complexes according to the invention is described schematically below (scheme 1: single antenna and scheme 2: two antennae), and in more detail in the experimental part.

Scheme 1

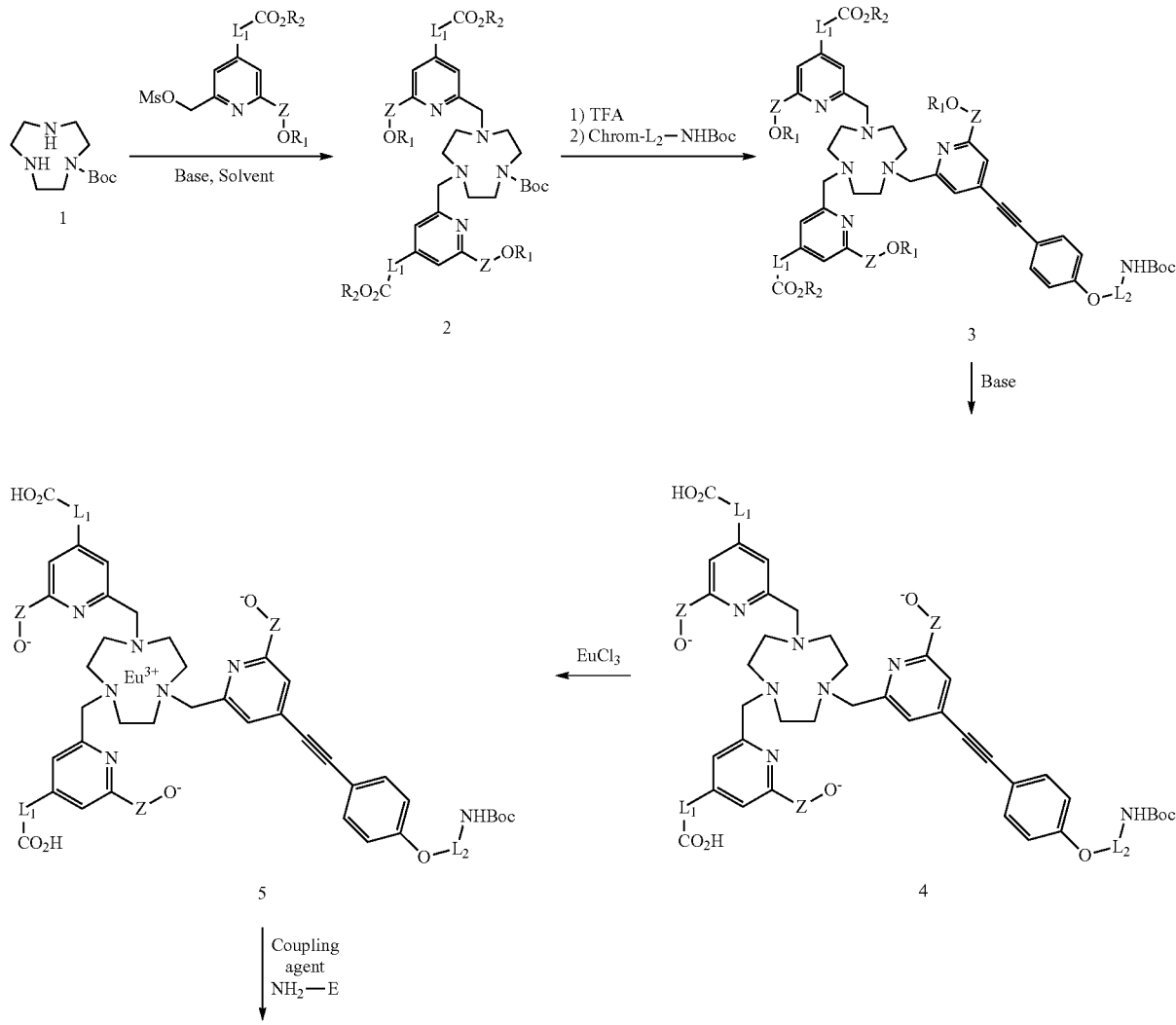

-continued

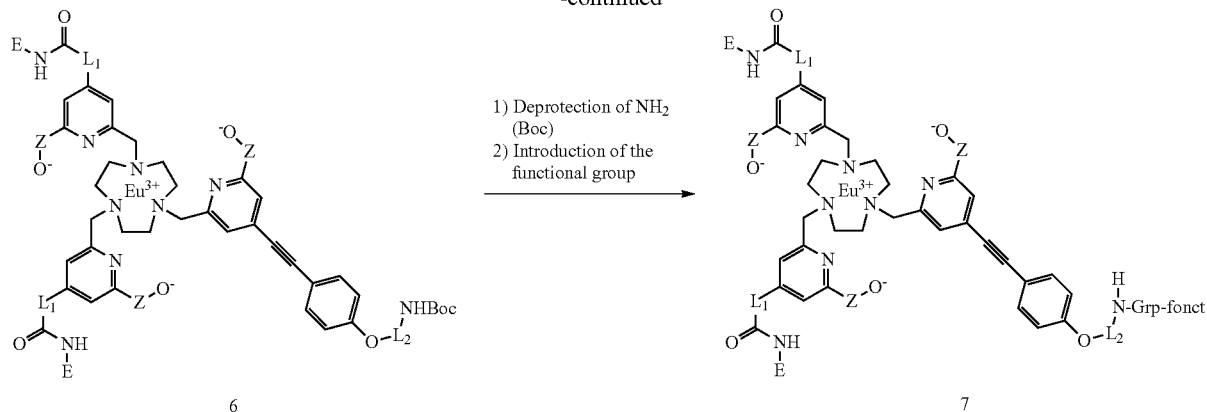

Z = PMe(O), PPh(O), CO L₁, L₂ = linker R₁, R₂ = alkyl E = solubilizing group Grp-fonct = functional group From the Boc-monoprotected triazacyclonane macrocycle 1, the two pyridinyl units were introduced which will be used to attach the two solubilizing groups. The protective group Boc was removed and then the antenna (chromophore) was added on the macrocycle leading to the ligand 3. The hydrolysis of esters (carboxylates and phosphinates) was carried out in a conventional way using basic conditions. This then allowed the europium atom to be incorporated, thus forming the complexes 5, from which the two water-solubilizing functions were introduced. Finally, after deprotection of the protective group Boc carried by the antenna (chromophore), the complexes were functionalized (7) so that they could be conjugated on biomolecules.

Scheme 2

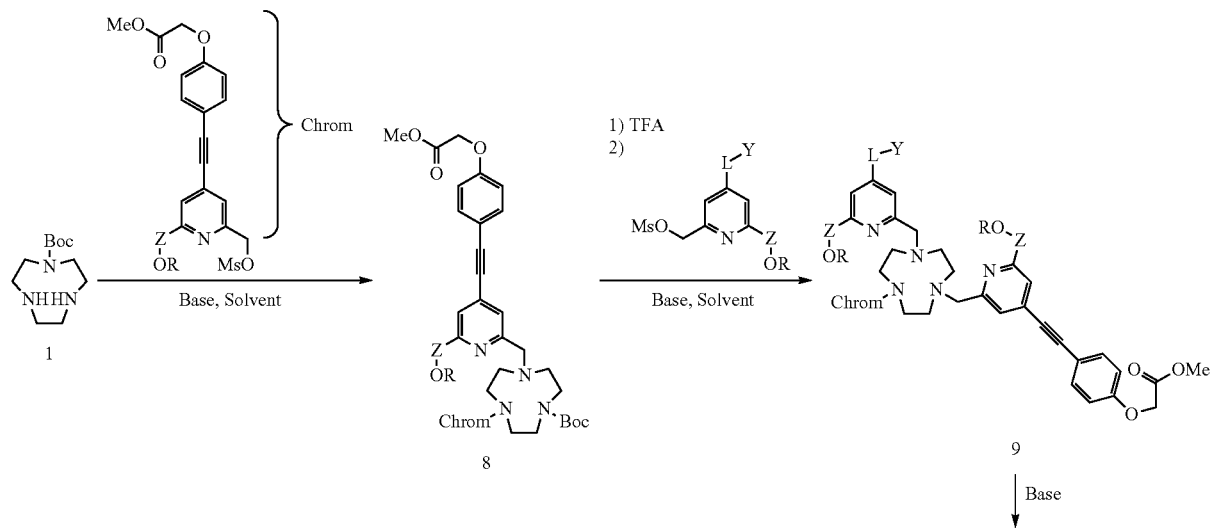

13 14

-continued

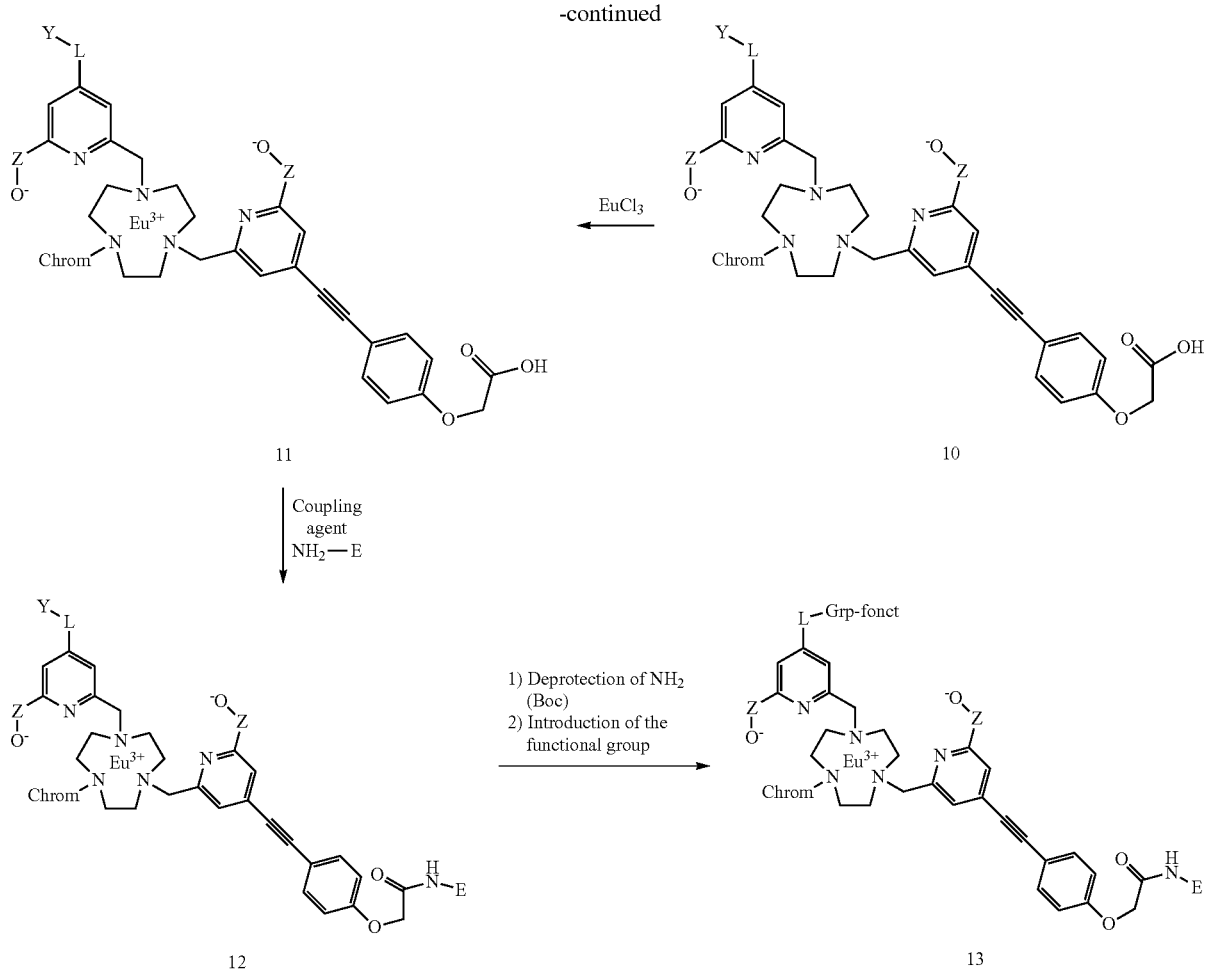

Z = PMe(O), PPh(O), CO  Y = NHBoc, CO₂tBu  L = linker  R = alkyl  E = solubilizing group  Grp-fonct = functional group Two-antenna systems were obtained by using a similar strategy but reversing the order of introduction of pyridinyl units and chromophores. This time the antennae were introduced first to lead to the compounds 8. After deletion of the Boc group, the last pyridinyl unit was introduced. The sequence was identical, namely hydrolysis of the ester functions (carboxylates and phosphinates), formation of the europium complex, introduction of the two water-solubilizing functions (this time these functions are carried by the chromophores) and then incorporation of the functional group leading to the two-antenna family 13.

1) Preparation of Pyridinyl Bricks

The following schemes (3-11) describe the various synthetic pathways for trifunctional pydininyl derivatives:
in position 2 the complexing function (carboxylic acid or phosphinic acid),
in position 4 a function that allows either to introduce the water-solubilizing group (methyl ester function) or a function that allows to incorporate the functional group (protected amine function and tert-butyl ester function)
and finally in position 6 a methyl alcohol function which is converted to the corresponding mesylate in order to be able to react with the amines of the TACN ring.

Scheme 3

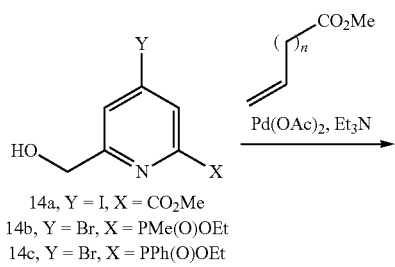

14a, Y = I, X = CO₂Me
14b, Y = Br, X = PMe(O)OEt
14c, Y = Br, X = PPh(O)OEt

15

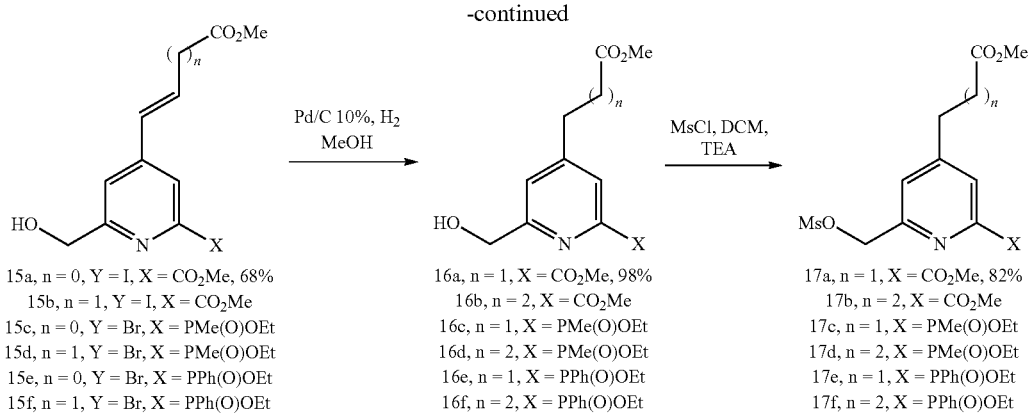

15a, n = 0, Y = I, X = CO₂Me, 68%
15b, n = 1, Y = I, X = CO₂Me
15c, n = 0, Y = Br, X = PMe(O)OEt
15d, n = 1, Y = Br, X = PMe(O)OEt
15e, n = 0, Y = Br, X = PPh(O)OEt
15f, n = 1, Y = Br, X = PPh(O)OEt 16a, n = 1, X = CO₂Me, 98%
16b, n = 2, X = CO₂Me
16c, n = 1, X = PMe(O)OEt
16d, n = 2, X = PMe(O)OEt
16e, n = 1, X = PPh(O)OEt
16f, n = 2, X = PPh(O)OEt 17a, n = 1, X = CO₂Me, 82%
17b, n = 2, X = CO₂Me
17c, n = 1, X = PMe(O)OEt
17d, n = 2, X = PMe(O)OEt
17e, n = 1, X = PPh(O)OEt
17f, n = 2, X = PPh(O)OEt

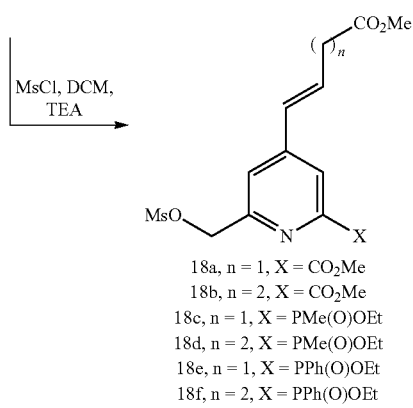

18a, n = 1, X = CO₂Me
18b, n = 2, X = CO₂Me
18c, n = 1, X = PMe(O)OEt
18d, n = 2, X = PMe(O)OEt
18e, n = 1, X = PPh(O)OEt
18f, n = 2, X = PPh(O)OEt

The syntheses of synthons 14a-c have been described above (see applications WO 2013/011236 and WO 2014/111661). From these synthons, the series of compounds 17a-f was obtained by a sequence of three reactions: Heck reaction to create the carbon-carbon bond between the pyridine derivative and the alkene. This procedure was described, for example, in patent application EP-A-2 002 836. The reduction of the double bond by catalytic hydrogenation followed by the mesylation reaction led to compounds 17a-f. Alternatively, the double bond was retained to stiffen the system and impose apical orientation on the water-solubilizing groups (18a-f).

Scheme 4

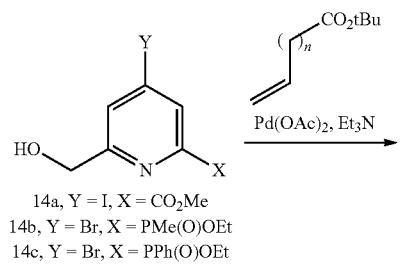

14a, Y = I, X = CO₂Me
14b, Y = Br, X = PMe(O)OEt
14c, Y = Br, X = PPh(O)OEt

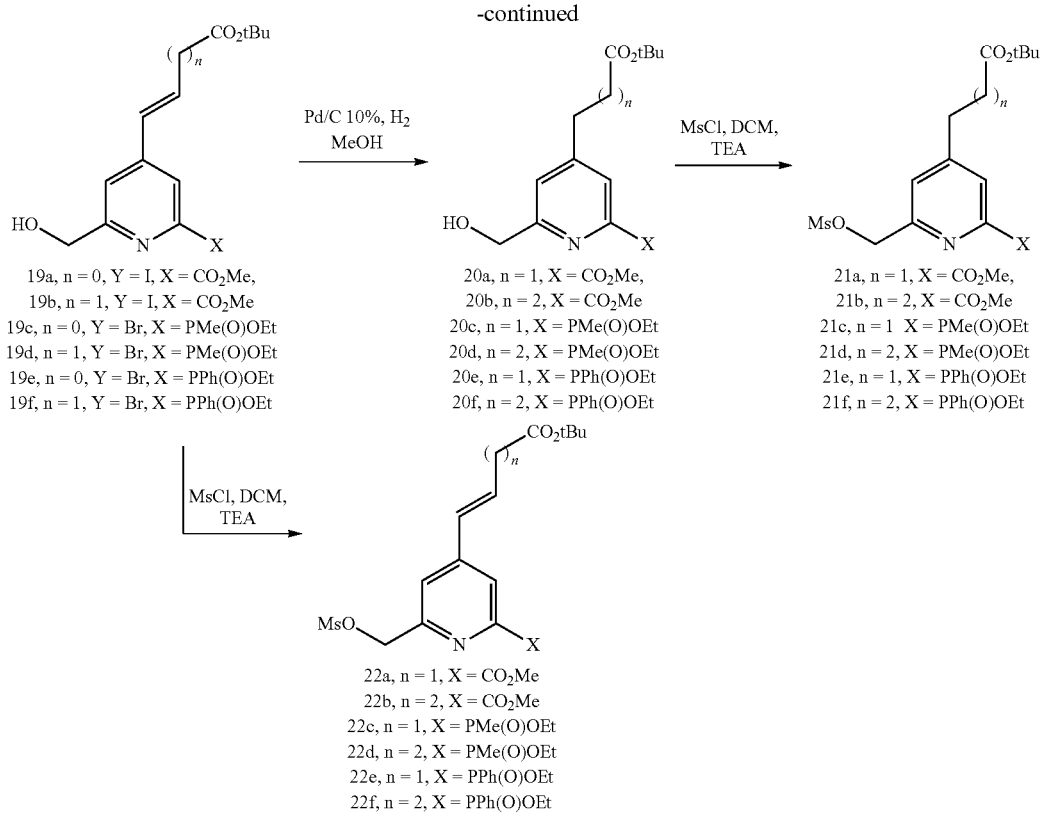
Compounds 21a-f and 22a-f (scheme 4) in tert-butyl ester form (analogues of series 17 and 18) were obtained by following the same strategy and using the corresponding alkene.
Scheme 5
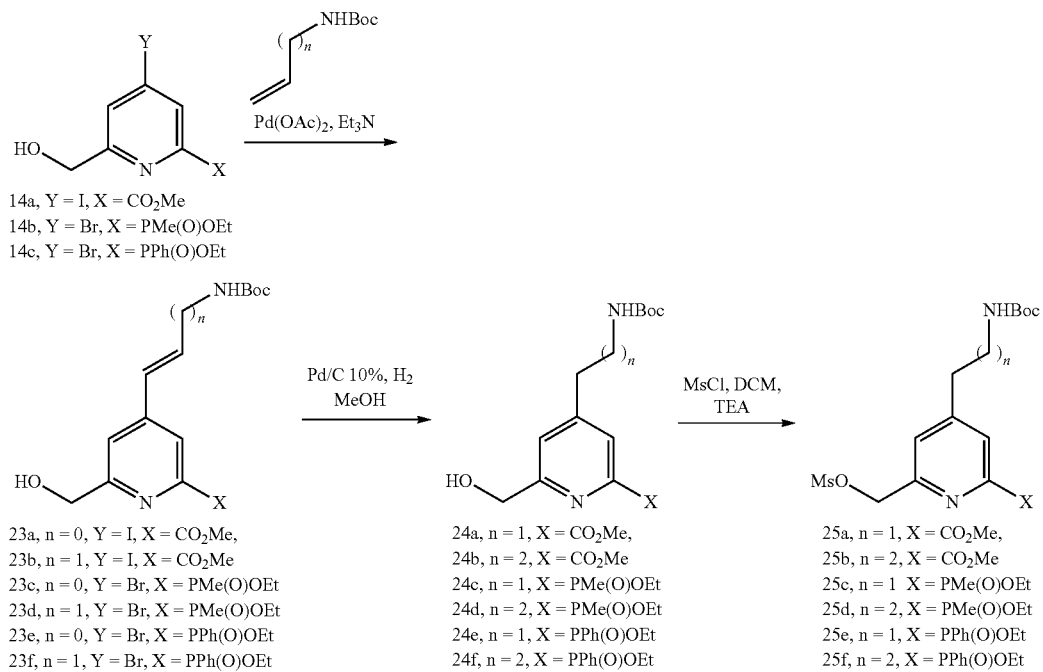

-continued

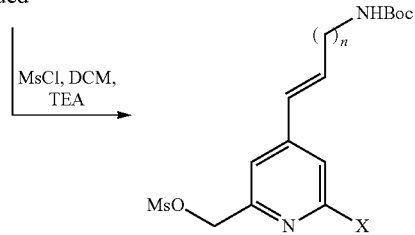

26a, n = 1, X = CO$_2$Me
26b, n = 2, X = CO$_2$Me
26c, n = 1, X = PMe(O)OEt
26d, n = 2, X = PMe(O)OEt
26e, n = 1, X = PPh(O)OEt
26f, n = 2, X = PPh(O)OEt

Compounds 25a-f and 26a-f (scheme 5) in NHBoc form (analogues of series 17 and 18) were obtained following the same strategy using the corresponding alkene.

Scheme 6

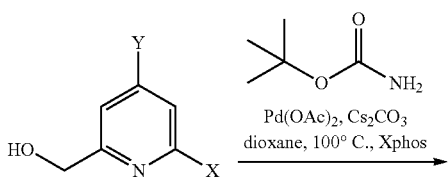

14a, Y = I, X = CO$_2$Me
14b, Y = Br, X = PMe(O)OEt
14c, Y = Br, X = PPh(O)OEt

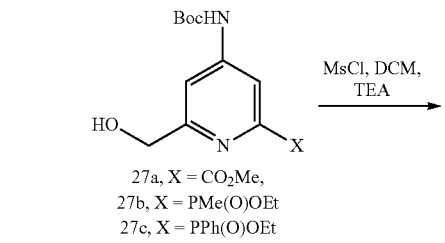

27a, X = CO$_2$Me,
27b, X = PMe(O)OEt
27c, X = PPh(O)OEt

-continued

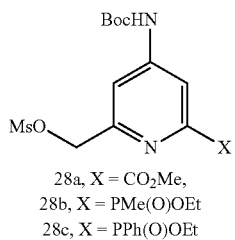

28a, X = CO$_2$Me,
28b, X = PMe(O)OEt
28c, X = PPh(O)OEt

Compounds 28a-c (carbon chain-free), analogues of the 25 series, were prepared according to a similar strategy. The introduction of the NHBoc group was carried out, for example, using the method described in the review article Tetrahedron Letters 2010, 51, 4445.

Scheme 7

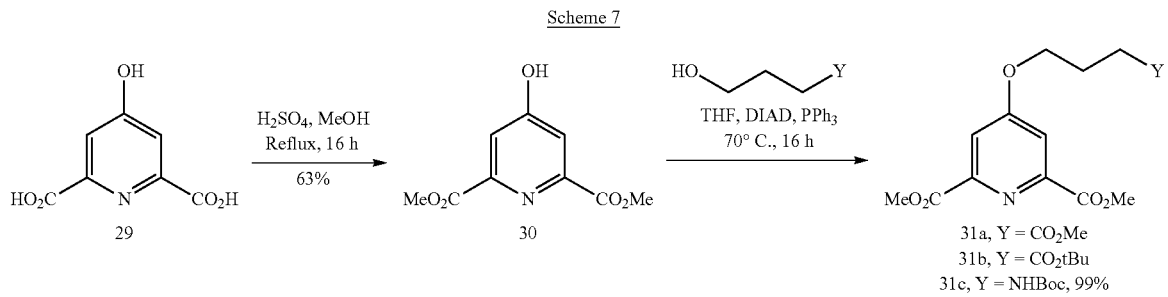

31a, Y = CO$_2$Me
31b, Y = CO$_2$tBu
31c, Y = NHBoc, 99%

NaBH$_4$
MeOH, CH$_2$Cl$_2$
0° C.

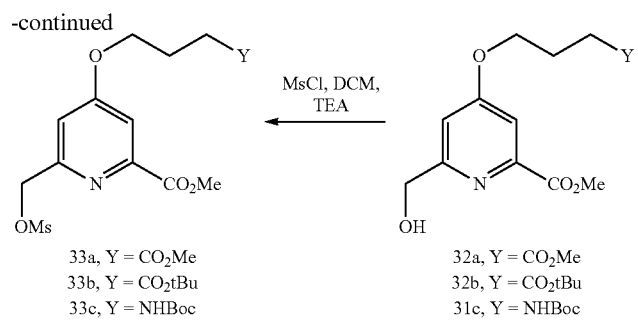

33a, Y = CO₂Me
33b, Y = CO₂tBu
33c, Y = NHBoc

32a, Y = CO₂Me
32b, Y = CO₂tBu
31c, Y = NHBoc

Pyridinyl derivatives on which an oxygen atom is interposed in position 4 between the aliphatic linker carrying the function (CO₂R or NHBoc) and the aromatic ring (pyridine), were prepared according to the method described in scheme 7. The chelidamic acid 29 was esterified as methyl diester and then the linker carrying the function was introduced using a Mitsunobu reaction (procedure described for example in Organic Biomolecular Chemistry 2012, 10, 9183). Mono-reduction using sodium borohydride produced compounds 32a-c in the form of monoalcohols which were then converted into corresponding mesylated derivatives 33a-c.

The methyl ester function in position 4 can be fixed directly to the aromatic ring (pyridine). In this case, it was necessary to start from the commercial compound 34 that was first esterified. The pyridine was then oxidized in the presence of m-CPBA leading to the corresponding N-oxide derivative 36. The N-oxide function reacted easily with trifluoroacetic anhydride which was rearranged to lead after hydrolysis to the methyl alcohol function in position 6. The latter was mesylated under conventional conditions leading to compound 38.

Scheme 8

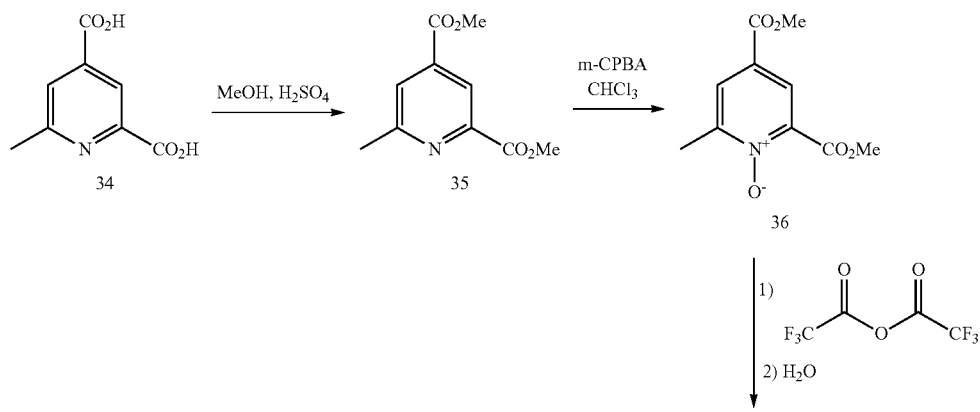

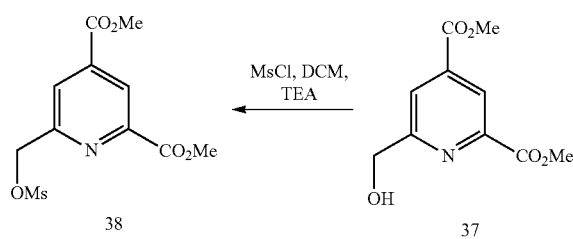

Scheme 9

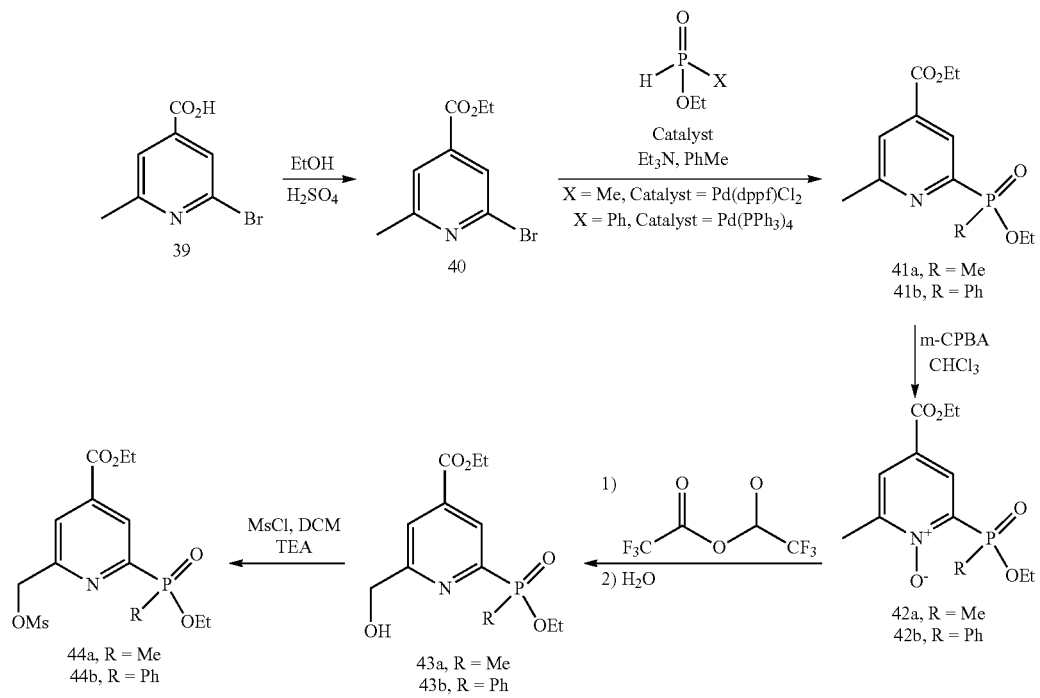

Analogous phosphinate derivatives 44a-b were prepared using compound 39 which was first esterified and then converted to phosphinate ester 41a-b. The rest of the reaction sequence was identical to that used for the synthesis of compound 38.

Derivatives 51a-b were prepared according to the reaction sequence described in scheme 10. In this example the ester functions were introduced using ethyl or tert-butyl thioglycolate.

Scheme 10

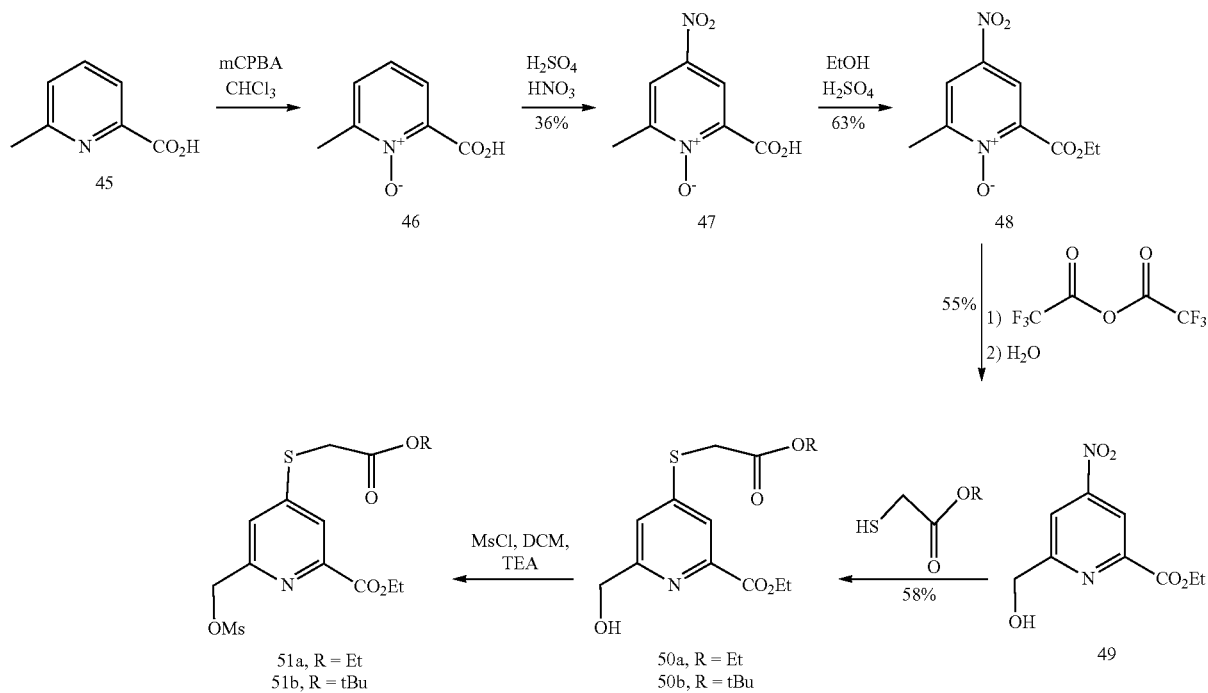

Scheme 11
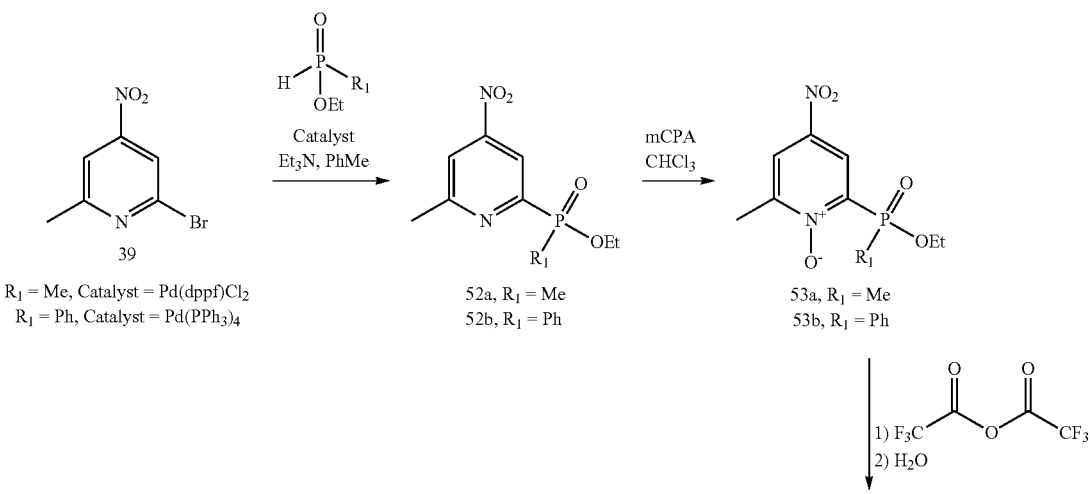
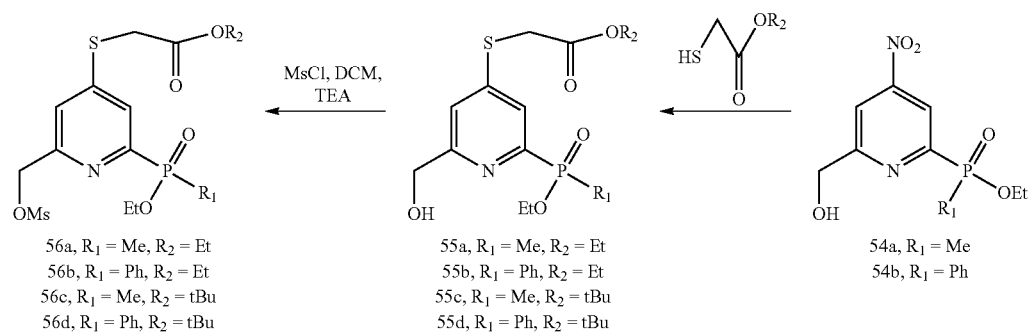

Phosphinate analogues 56a-d were prepared according to the synthesis route described in scheme 11.
1) Preparation of Chromophores
Chromophores 58a-c (scheme 12) and 60a-c (scheme 13) were prepared according to the protocols detailed in applications WO 2013/011236 and WO 2014/111661.
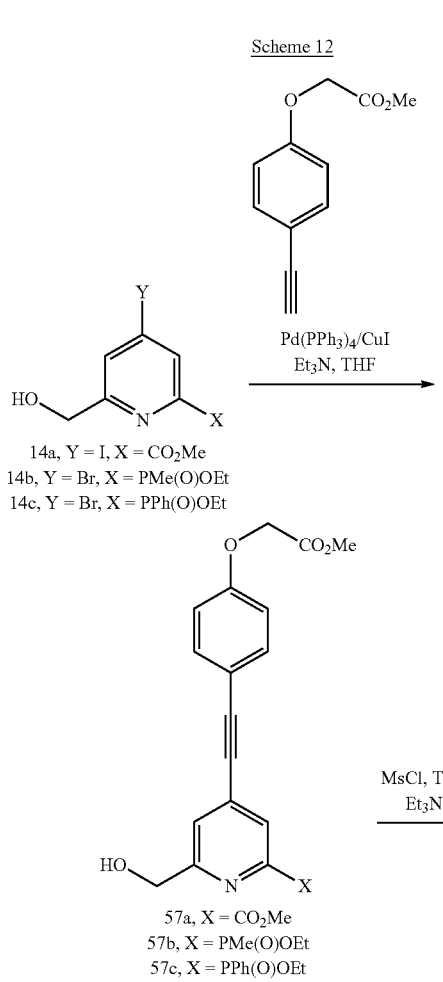
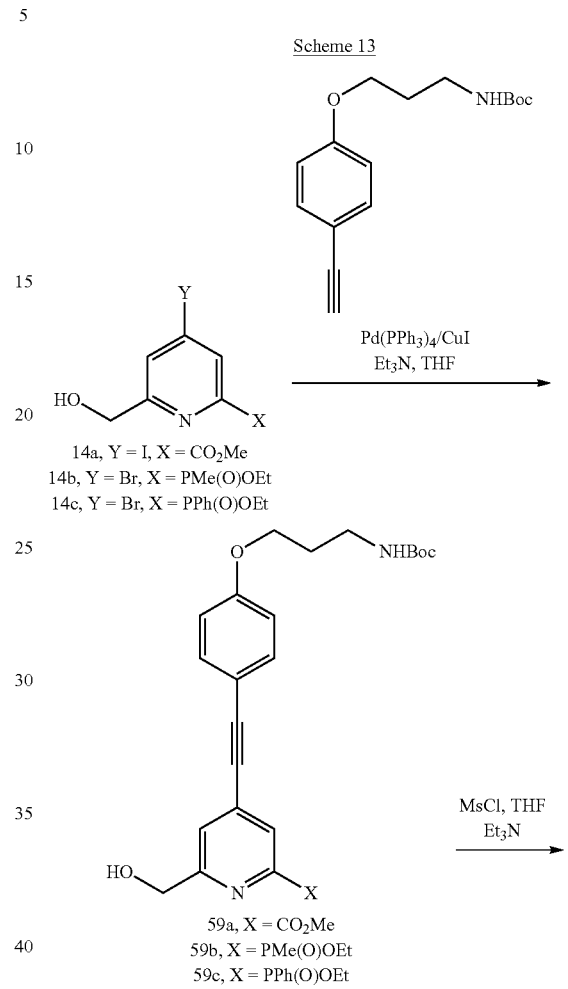
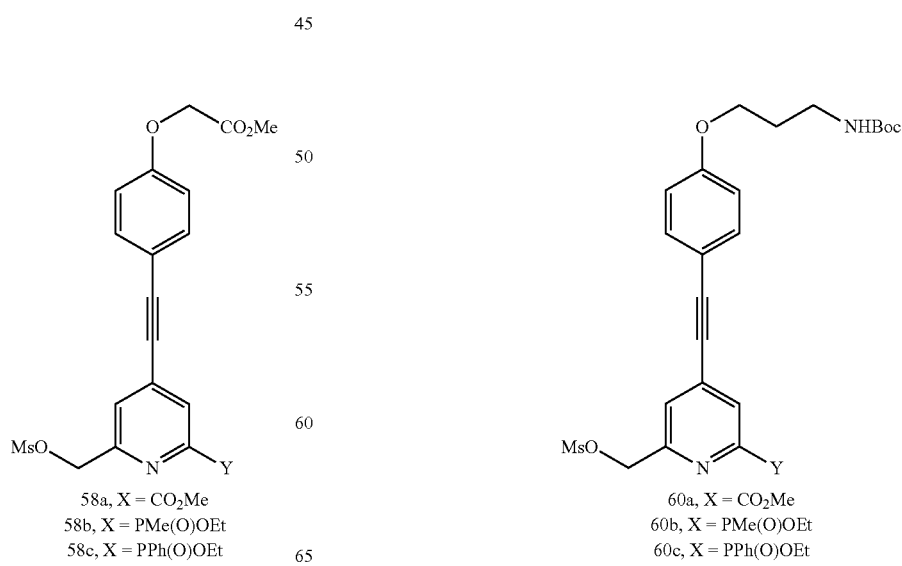

1) Synthesis of Single Antenna Complexes

Scheme 14

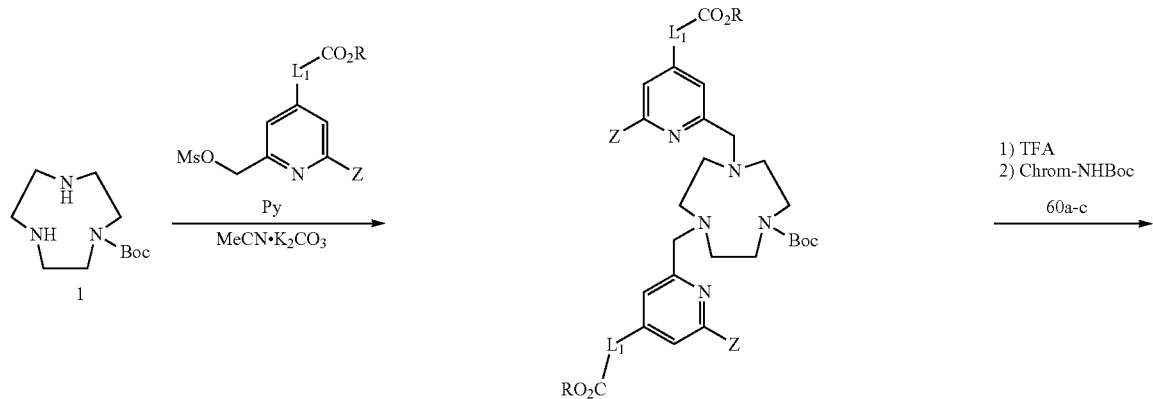

61a, Py = 38, Z = CO$_2$ME, L$_1$ = 0, R = Me
61b, Py = 44a, Z = PMe(O)OEt, L$_1$ = 0, R = Et
61c, Py = 44b, Z = PPh(O)OEt, L$_1$ = 0, R = Et
61d, Py = 17a, Z = CO$_2$Me, L$_1$ = ―(CH$_2$)$_2$―, R = Me
61e, Py = 17b, Z = CO$_2$Me, L$_1$ = ―(CH$_2$)$_3$―, R = Me
61f, Py = 17c, Z = PMe(O)OEt, L$_1$ = ―(CH$_2$)$_2$―, R = Me
61g, Py = 17d, Z = PMe(O)OEt, L$_1$ = ―(CH$_2$)$_3$―, R = Me
61h, Py = 17e, Z = PPh(O)OEt, L$_1$ = ―(CH$_2$)$_2$―, R = Me
61i, Py = 17f, Z = PPh(O)OEt, L$_1$ = ―(CH$_2$)$_3$―, R = Me
61j, Py = 33a, Z = CO$_2$Me, L$_1$ = ―O(CH$_2$)$_3$―, R = Me
61k, Py = 51a, Z = CO$_2$Me, L$_1$ = SCH$_2$, R = Et
61l, Py = 56a, Z = PMe(O)OEt, L$_1$ = SCH$_2$, R = Et
61m, Py = 56b, Z = PPh(O)OEt, L$_1$ = SCH$_2$, R = Et
61n, Py = 18a, Z = CO$_2$Me, L$_1$ = ―CH=CH―, R = Me
61o, Py = 18b, Z = CO$_2$Me, L$_1$ = ―CH=CH―CH$_2$―, R = Me
61p, Py = 18c, Z = PMe(O)OEt, L$_1$ = ―CH=CH―, R = Me
61q, Py = 18d, Z = PMe(O)OEt, L$_1$ = ―CH=CH―CH$_2$―, R = Me
61r, Py = 18e, Z = PPh(O)OEt, L$_1$ = ―CH=CH―, R = Me
61s, Py = 18f, Z = PPh(O)OEt, L$_1$ = ―CH=CH―CH$_2$―, R = Me

-continued

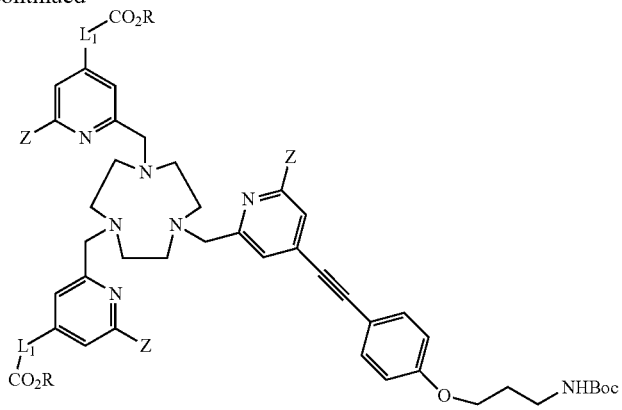

61a, Z = CO₂Me, L₁ = 0, R = Me
61b, Z = PMe(O)OEt, L₁ = 0, R = Et
61c, Z = PPh(O)OEt, L₁ = 0, R = Et
61d, Z = CO₂Me, L₁ = —(CH₂)₂—, R = Me
61e, Z = CO₂Me, L₁ = —(CH₂)₃—, R = Me
61f, Z = PMe(O)OEt, L₁ = —(CH₂)₂—, R = Me
61g, Z = PMe(O)OEt, L₁ = —(CH₂)₃—, R = Me
61h, Z = PPh(O)OEt, L₁ = —(CH₂)₂—, R = Me
61i, Z = PPh(O)OEt, L₁ = —(CH₂)₃—, R = Me
61j, Z = CO₂Me, L₁ = —O(CH₂)₃—, R = Me
61k, Z = CO₂Me, L₁ = SCH₂, R = Et
61l, Z = PMe(O)OEt, L₁ = SCH₂, R = Et
61m, Z = PPh(O)OEt, L₁ = SCH₂, R = Et
61n, Z = CO₂Me, L₁ = —CH═CH—, R = Me
61o, Z = CO₂Me, L₁ = —CH═CH—CH₂—, R = Me
61p, Z = PMe(O)OEt, L₁ = —CH═CH—, R = Me
61q, Z = PMe(O)OEt, L₁ = —CH═CH—CH₂—, R = Me
61r, Z = PPh(O)OEt, L₁ = —CH═CH—, R = Me
61s, Z = PPh(O)OEt, L₁ = —CH═CH—CH₂—, R = Me

↓ LiOH

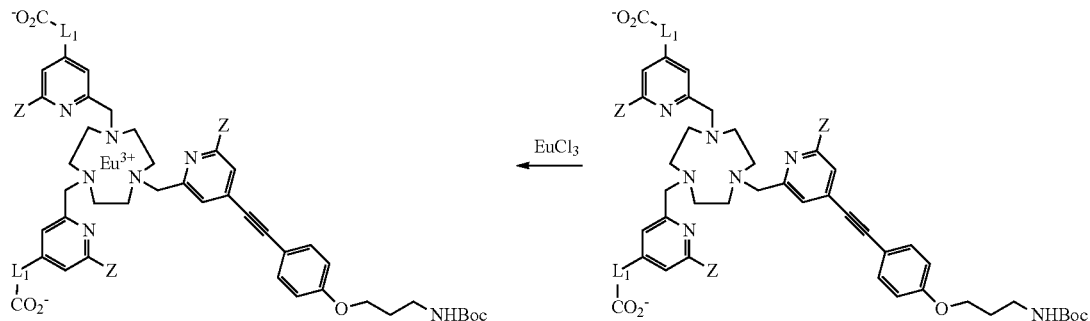

-continued

64a, Z = CO$_2^-$, L$_1$ = 0
64b, Z = PMe(O)O$^-$, L$_1$ = 0
64c, Z = PPh(O)O$^-$, L$_1$ = 0
64d, Z = CO$_2^-$ L$_1$ = —(CH$_2$)$_2$—
64e, Z = CO$_2^-$, L$_1$ = —(CH$_2$)$_3$—
64f, Z = PMe(O)O$^-$, L$_1$ = —(CH$_2$)$_2$—
64g, Z = PMe(O)O$^-$, L$_1$ = —(CH$_2$)$_3$—
64h, Z = PPh(O)O$^-$, L$_1$ = —(CH$_2$)$_2$—
64i, Z = PPh(O)O$^-$, L$_1$ = —(CH$_2$)$_3$—
64j, Z = CO$_2^-$, L$_1$ = —O(CH$_2$)$_3$—
64k, Z = CO$_2^-$, L$_1$ = SCH$_2$
64l, Z = PMe(O)O$^-$, L$_1$ = SCH$_2$
64m, Z = PPh(O)O$^-$, L$_1$ = SCH$_2$
64n, Z = CO$_2^-$, L$_1$ = —CH=CH—
64o, Z = CO$_2^-$, L$_1$ = —CH=CH—CH$_2$—
64p, Z = PMe(O)O$^-$, L$_1$ = —CH=CH—
64q, Z = PMe(O)O$^-$, L$_1$ = —CH=CH—CH$_2$—
64r, Z = PPh(O)O$^-$, L$_1$ = —CH=CH—
64s, Z = PPh(O)O$^-$, L$_1$ = —CH=CH—CH$_2$—

63a, Z = CO$_2^-$, L$_1$ = 0
63b, Z = PMe(O)O$^-$, L$_1$ = 0
63c, Z = PPh(O)O$^-$, L$_1$ = 0
63d, Z = CO$_2^-$ L$_1$ = —(CH$_2$)$_2$—
63e, Z = CO$_2^-$, L$_1$ = —(CH$_2$)$_3$—
63f, Z = PMe(O)O$^-$, L$_1$ = —(CH$_2$)$_2$—
63g, Z = PMe(O)O$^-$, L$_1$ = —(CH$_2$)$_3$—
63h, Z = PPh(O)O$^-$, L$_1$ = —(CH$_2$)$_2$—
63i, Z = PPh(O)O$^-$, L$_1$ = —(CH$_2$)$_3$—
63j, Z = CO$_2^-$, L$_1$ = —O(CH$_2$)$_3$—
63k, Z = CO$_2^-$, L$_1$ = SCH$_2$
63l, Z = PMe(O)O$^-$, L$_1$ = SCH$_2$
63m, Z = PPh(O)O$^-$, L$_1$ = SCH$_2$
63n, Z = CO$_2^-$, L$_1$ = —CH=CH—
63o, Z = CO$_2^-$, L$_1$ = —CH=CH—CH$_2$—
63p, Z = PMe(O)O$^-$, L$_1$ = —CH=CH—
63q, Z = PMe(O)O$^-$, L$_1$ = —CH=CH—CH$_2$—
63r, Z = PPh(O)O$^-$, L$_1$ = —CH=CH—
63s, Z = PPh(O)O$^-$, L$_1$ = —CH=CH—CH$_2$—

From the Boc-monoprotected TACN macrocycle, pyridinyl derivatives (Py) leading to compounds 61a-s were condensed. The macrocycle was deprotected and the corresponding chromophore (Z identical to those carried by the Py) was introduced on the ligand. The ester functions were hydrolysed (series 63) and the europium was complexed in the different ligands to lead to the series of complexes 64a-s.

Scheme 15

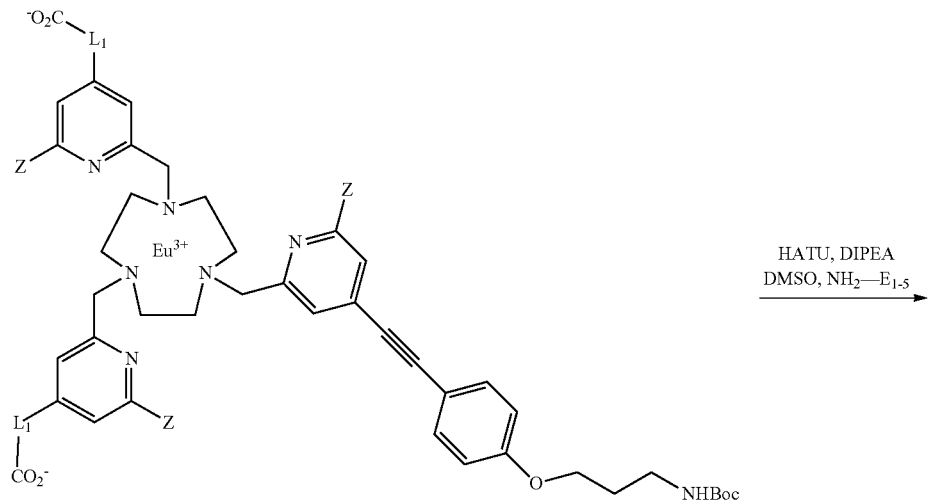

-continued

64a, Z = CO$_2^-$, L$_1$ = 0
64b, Z = PMe(O)O$^-$, L$_1$ = 0
64c, Z = PPh(O)O$^-$, L$_1$ = 0
64d, Z = CO$_2^-$, L$_1$ = —(CH$_2$)$_2$—
64e, Z = CO$_2^-$, L$_1$ = —(CH$_2$)$_3$—
64f, Z = PMe(O)O$^-$, L$_1$ = —(CH$_2$)$_2$—
64g, Z = PMe(O)O$^-$, L$_1$ = —(CH$_2$)$_3$—
64h, Z = PPh(O)O$^-$, L$_1$ = —(CH$_2$)$_2$—
64i, Z = PPh(O)O$^-$, L$_1$ = —(CH$_2$)$_3$—
64j, Z = CO$_2^-$, L$_1$ = —O(CH$_2$)$_3$—
64k, Z = CO$_2^-$, L$_1$ = SCH$_2$
64l, Z = PMe(O)O$^-$, L$_1$ = SCH$_2$
64m, Z = PPh(O)O$^-$, L$_1$ = SCH$_2$
64n, Z = CO$_2^-$, L$_1$ = —CH═CH—
64o, Z = CO$_2^-$, L$_1$ = —CH═CH—CH$_2$
64p, Z = PMe(O)O$^-$, L$_1$ = —CH═CH—
64q, Z = PMe(O)O$^-$, L$_1$ = —CH═CH—CH$_2$
64r, Z = PPh(O)O$^-$, L$_1$ = —CH═CH—
64s, Z = PPh(O)O$^-$, L$_1$ = —CH═CH—CH$_2$

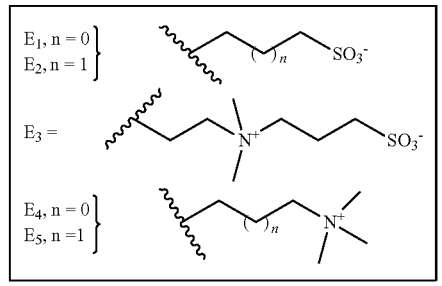

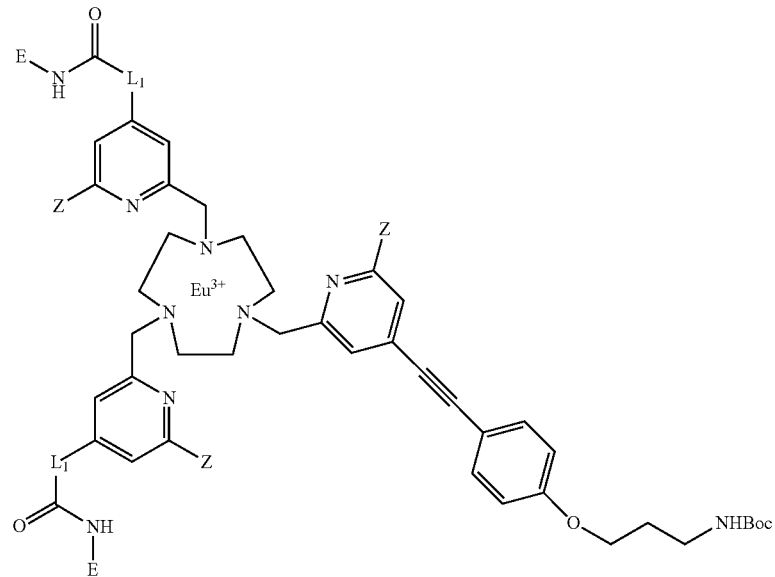

-continued

65a-E$_1$, Z = CO$_2^-$, L$_1$ = 0
65a-E$_2$, Z = CO$_2^-$, L$_1$ = 0
65a-E$_3$, Z = CO$_2^-$, L$_1$ = 0
65a-E$_4$, Z = CO$_2^-$, L$_1$ = 0
65a-E$_5$, Z = CO$_2^-$, L$_1$ = 0
65b-E$_{1-5}$, Z = PMe(O)O$^-$ L$_1$ = 0
65c-E$_{1-5}$, Z = PPh(O)O$^-$, L$_1$ = 0
65d-E$_{1-5}$, Z = CO$_2^-$, L$_1$ = —(CH$_2$)$_2$—
65e-E$_{1-5}$, Z = CO$_2^-$, L$_1$ = —(CH$_2$)$_3$—
65f-E$_{1-5}$, Z = PMe(O)O$^-$, L$_1$ = —(CH$_2$)$_2$—
65g-E$_{1-5}$, Z = PMe(O)O$^-$, L$_1$ = —(CH$_2$)$_3$—
65h-E$_{1-5}$, Z = PPh(O)O$^-$, L$_1$ = —(CH$_2$)$_2$—
65i-E$_{1-5}$, Z = PPh(O)O$^-$, L$_1$ = —(CH$_2$)$_3$—
65j-E$_{1-5}$, Z = CO$_2^-$, L$_1$ = —O(CH$_2$)$_3$—
65k-E$_{1-5}$, Z = CO$_2^-$, L$_1$ = SCH$_2$
65l-E$_{1-5}$, Z = PMe(O)O$^-$, L$_1$ = SCH$_2$
65m-E$_{1-5}$, Z = PPh(O)O$^-$, L$_1$ = SCH$_2$
65n-E$_{1-5}$, Z = CO$_2^-$, L$_1$ = —CH=CH—,
65o-E$_{1-5}$, Z = CO$_2^-$, L$_1$ = —CH=CH—CH$_2$—,
65p-E$_{1-5}$, Z = PMe(O)O$^-$, L$_1$ = —CH=CH—,
65q-E$_{1-5}$, Z = PMe(O)O$^-$, L$_1$ = —CH=CH—CH$_2$—,
65r-E$_{1-5}$, Z = PPh(O)O$^-$, L$_1$ = —CH=CH—,
65s-E$_{1-5}$, Z = PPh(O)O$^-$, L$_1$ = —CH=CH—CH$_2$—,

On series 64a-s, the compounds were made soluble in aqueous media by the introduction of two water-solubilizing groups: these groups are either anionic (sulfonates) or neutral (zwitterion: sulfobetaines), or cationic (quaternary ammonium) in nature.

Scheme 16

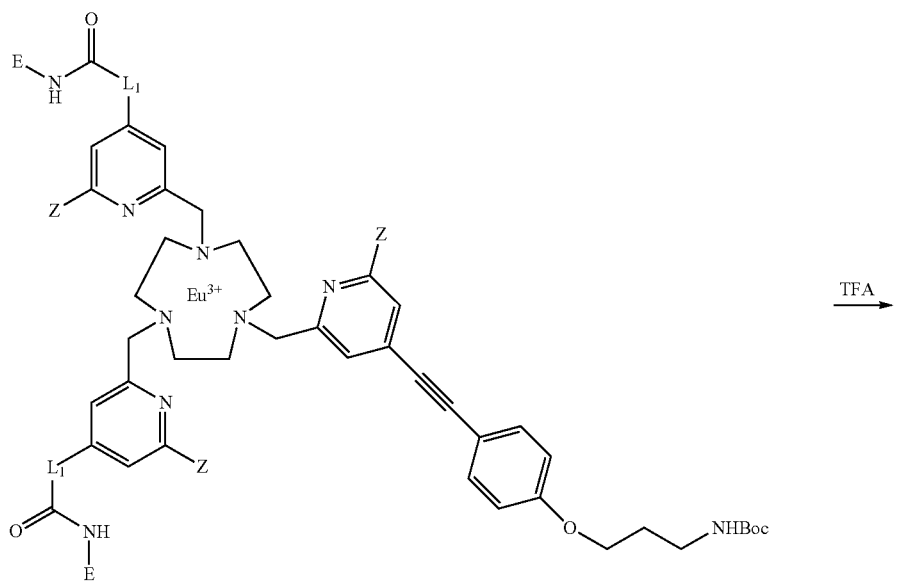

TFA →

-continued

65a-E$_1$, Z = CO$_2^-$, L$_1$ = 0
65a-E$_2$, Z = CO$_2^-$, L$_1$ = 0
65a-E$_3$, Z = CO$_2^-$, L$_1$ = 0
65a-E$_4$, Z = CO$_2^-$, L$_1$ = 0
65a-E$_5$, Z = CO$_2^-$, L$_1$ = 0
65b-E$_{1-5}$, Z = PMe(O)O$^-$ L$_1$ = 0
65c-E$_{1-5}$, Z = PPh(O)O$^-$, L$_1$ = 0
65d-E$_{1-5}$, Z = CO$_2^-$, L$_1$ = —(CH$_2$)$_2$—
65e-E$_{1-5}$, Z = CO$_2^-$, L$_1$ = —(CH$_2$)$_3$—
65f-E$_{1-5}$, Z = PMe(O)O$^-$, L$_1$ = —(CH$_2$)$_2$—
65g-E$_{1-5}$, Z = PMe(O)O$^-$, L$_1$ = —(CH$_2$)$_3$—
65h-E$_{1-5}$, Z = PPh(O)O$^-$, L$_1$ = —(CH$_2$)$_2$—
65i-E$_{1-5}$, Z = PPh(O)O$^-$, L$_1$ = —(CH$_2$)$_3$—
65j-E$_{1-5}$, Z = CO$_2^-$, L$_1$ = —O(CH$_2$)$_3$—
65k-E$_{1-5}$, Z = CO$_2^-$, L$_1$ = SCH$_2$
65l-E$_{1-5}$, Z = PMe(O)O$^-$, L$_1$ = SCH$_2$
65m-E$_{1-5}$, Z = PPh(O)O$^-$, L$_1$ = SCH$_2$
65n-E$_{1-5}$, Z = CO$_2^-$, L$_1$ = —CH=CH—,
65o-E$_{1-5}$, Z = CO$_2^-$, L$_1$ = —CH=CH—CH$_2$—,
65p-E$_{1-5}$, Z = PMe(O)O$^-$, L$_1$ = —CH=CH—,
65q-E$_{1-5}$, Z = PMe(O)O$^-$, L$_1$ = —CH=CH—CH$_2$—,
65r-E$_{1-5}$, Z = PPh(O)O$^-$, L$_1$ = —CH=CH—,
65s-E$_{1-5}$, Z = PPh(O)O$^-$, L$_1$ = —CH=CH—CH$_2$—,

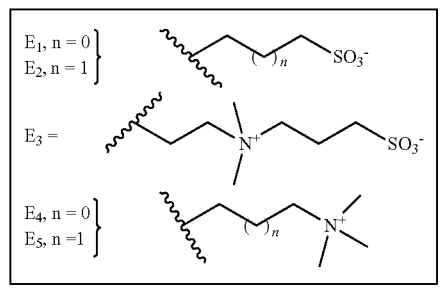

-continued

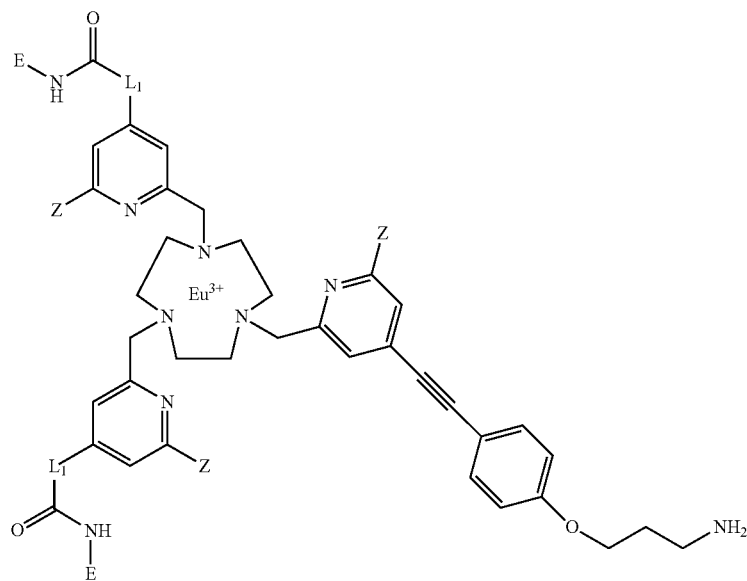

66a-E₁, Z = CO₂⁻, L₁ = 0
66a-E₂, Z = CO₂⁻, L₁ = 0
66a-E₃, Z = CO₂⁻, L₁ = 0
66a-E₄, Z = CO₂⁻, L₁ = 0
66a-E₅, Z = CO₂⁻, L₁ = 0
66b-E$_{1-5}$, Z = PMe(O)O⁻ L₁ = 0
66c-E$_{1-5}$, Z = PPh(O)O⁻, L₁ = 0
66d-E$_{1-5}$, Z = CO₂⁻, L₁ = —(CH₂)₂—
66e-E$_{1-5}$, Z = CO₂⁻, L₁ = —(CH₂)₃—
66f-E$_{1-5}$, Z = PMe(O)O⁻, L₁ = —(CH₂)₂—
66g-E$_{1-5}$, Z = PMe(O)O⁻, L₁ = —(CH₂)₃—
66h-E$_{1-5}$, Z = PPh(O)O⁻, L₁ = —(CH₂)₂—
66i-E$_{1-5}$, Z = PPh(O)O⁻, L₁ = —(CH₂)₃—
66j-E$_{1-5}$, Z = CO₂⁻, L₁ = —O(CH₂)₃—
66k-E$_{1-5}$, Z = CO₂⁻, L₁ = SCH₂
66l-E$_{1-5}$, Z = PMe(O)O⁻, L₁ = SCH₂
66m-E$_{1-5}$, Z = PPh(O)O⁻, L₁ = SCH₂
66n-E$_{1-5}$, Z = CO₂⁻, L₁ = —CH═CH—,
66o-E$_{1-5}$, Z = CO₂⁻, L₁ = —CH═CH—CH₂—,
66p-E$_{1-5}$, Z = PMe(O)O⁻, L₁ = —CH═CH—,
66q-E$_{1-5}$, Z = PMe(O)O⁻, L₁ = —CH═CH—CH₂—,
66r-E$_{1-5}$, Z = PPh(O)O⁻, L₁ = —CH═CH—,
66s-E$_{1-5}$, Z = PPh(O)O⁻, L₁ = —CH═CH—CH₂—,

Finally, the Boc group was eliminated in the presence of trifluoroacetic acid, which led to the complexes of the invention that are $NH_2$ functionalized (66).

Synthesis of Two-Antenna Complexes

The synthesis of two-antenna complexes is described in schemes 17-20.

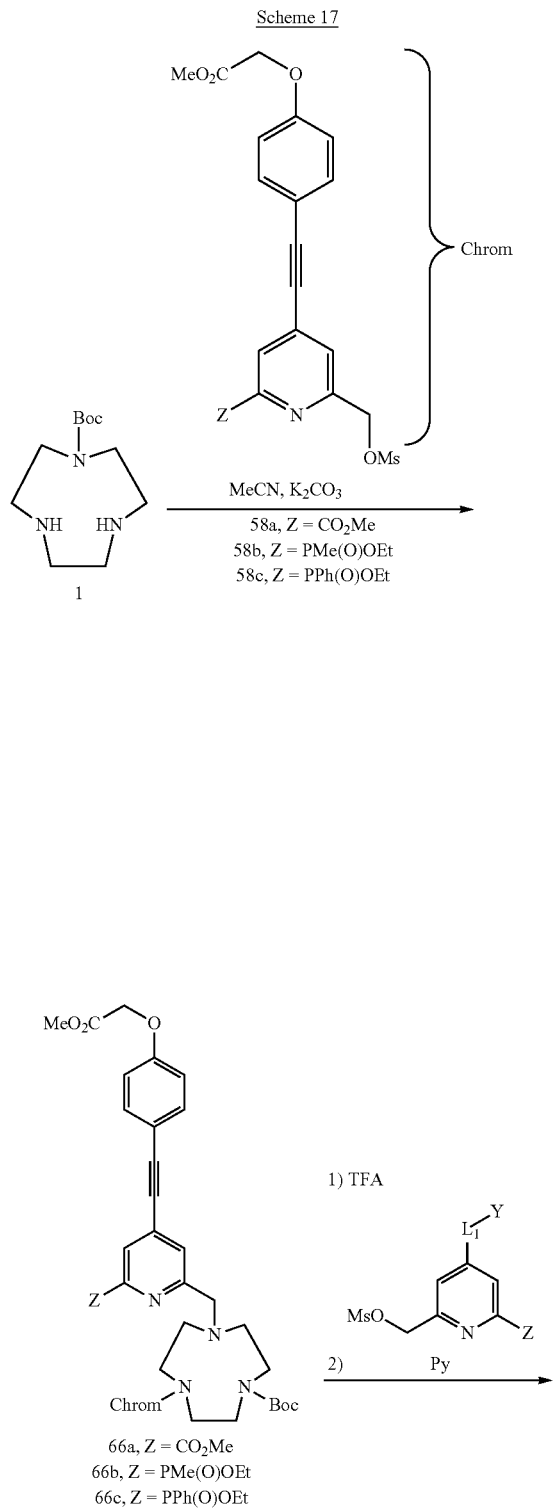

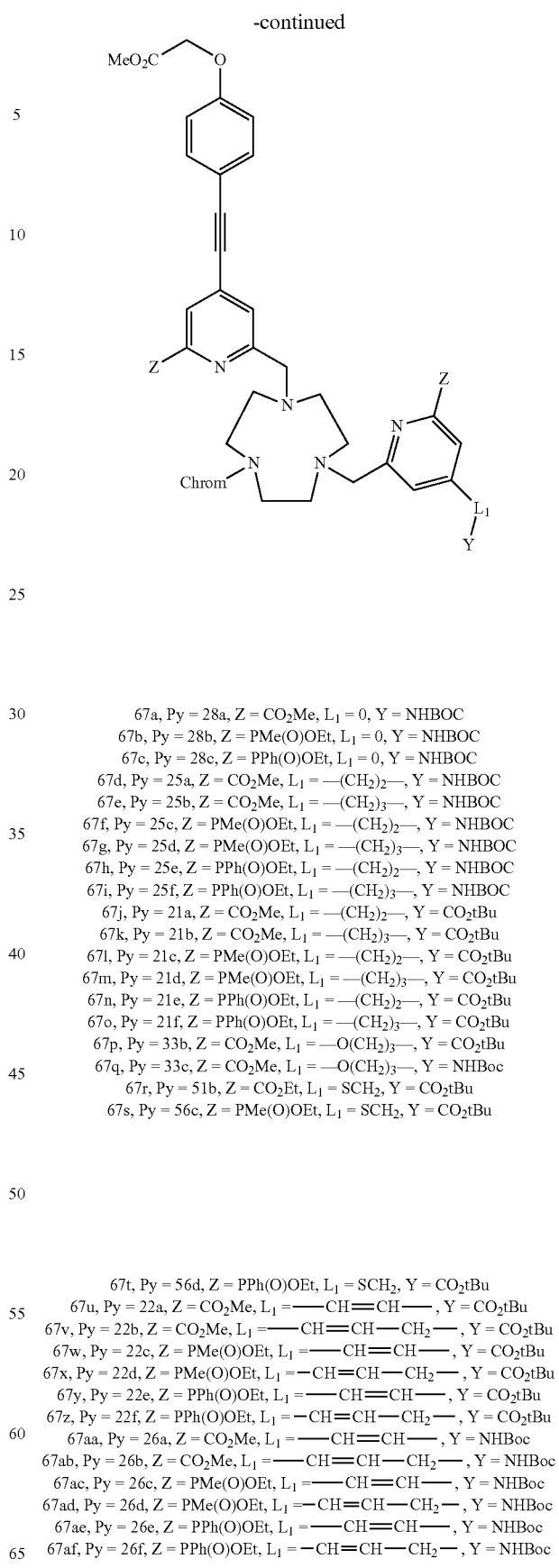

67a, Py = 28a, Z = $CO_2Me$, $L_1$ = 0, Y = NHBOC
67b, Py = 28b, Z = PMe(O)OEt, $L_1$ = 0, Y = NHBOC
67c, Py = 28c, Z = PPh(O)OEt, $L_1$ = 0, Y = NHBOC
67d, Py = 25a, Z = $CO_2Me$, $L_1$ = —$(CH_2)_2$—, Y = NHBOC
67e, Py = 25b, Z = $CO_2Me$, $L_1$ = —$(CH_2)_3$—, Y = NHBOC
67f, Py = 25c, Z = PMe(O)OEt, $L_1$ = —$(CH_2)_2$—, Y = NHBOC
67g, Py = 25d, Z = PMe(O)OEt, $L_1$ = —$(CH_2)_3$—, Y = NHBOC
67h, Py = 25e, Z = PPh(O)OEt, $L_1$ = —$(CH_2)_2$—, Y = NHBOC
67i, Py = 25f, Z = PPh(O)OEt, $L_1$ = —$(CH_2)_3$—, Y = NHBOC
67j, Py = 21a, Z = $CO_2Me$, $L_1$ = —$(CH_2)_2$—, Y = $CO_2tBu$
67k, Py = 21b, Z = $CO_2Me$, $L_1$ = —$(CH_2)_3$—, Y = $CO_2tBu$
67l, Py = 21c, Z = PMe(O)OEt, $L_1$ = —$(CH_2)_2$—, Y = $CO_2tBu$
67m, Py = 21d, Z = PMe(O)OEt, $L_1$ = —$(CH_2)_3$—, Y = $CO_2tBu$
67n, Py = 21e, Z = PPh(O)OEt, $L_1$ = —$(CH_2)_2$—, Y = $CO_2tBu$
67o, Py = 21f, Z = PPh(O)OEt, $L_1$ = —$(CH_2)_3$—, Y = $CO_2tBu$
67p, Py = 33b, Z = $CO_2Me$, $L_1$ = —$O(CH_2)_3$—, Y = $CO_2tBu$
67q, Py = 33c, Z = $CO_2Me$, $L_1$ = —$O(CH_2)_3$—, Y = NHBoc
67r, Py = 51b, Z = $CO_2Et$, $L_1$ = $SCH_2$, Y = $CO_2tBu$
67s, Py = 56c, Z = PMe(O)OEt, $L_1$ = $SCH_2$, Y = $CO_2tBu$

67t, Py = 56d, Z = PPh(O)OEt, $L_1$ = $SCH_2$, Y = $CO_2tBu$
67u, Py = 22a, Z = $CO_2Me$, $L_1$ = —CH=CH—, Y = $CO_2tBu$
67v, Py = 22b, Z = $CO_2Me$, $L_1$ = —CH=CH—$CH_2$—, Y = $CO_2tBu$
67w, Py = 22c, Z = PMe(O)OEt, $L_1$ = —CH=CH—, Y = $CO_2tBu$
67x, Py = 22d, Z = PMe(O)OEt, $L_1$ = —CH=CH—$CH_2$—, Y = $CO_2tBu$
67y, Py = 22e, Z = PPh(O)OEt, $L_1$ = —CH=CH—, Y = $CO_2tBu$
67z, Py = 22f, Z = PPh(O)OEt, $L_1$ = —CH=CH—$CH_2$—, Y = $CO_2tBu$
67aa, Py = 26a, Z = $CO_2Me$, $L_1$ = —CH=CH—, Y = NHBoc
67ab, Py = 26b, Z = $CO_2Me$, $L_1$ = —CH=CH—$CH_2$—, Y = NHBoc
67ac, Py = 26c, Z = PMe(O)OEt, $L_1$ = —CH=CH—, Y = NHBoc
67ad, Py = 26d, Z = PMe(O)OEt, $L_1$ = —CH=CH—$CH_2$—, Y = NHBoc
67ae, Py = 26e, Z = PPh(O)OEt, $L_1$ = —CH=CH—, Y = NHBoc
67af, Py = 26f, Z = PPh(O)OEt, $L_1$ = —CH=CH—$CH_2$—, Y = NHBoc

Synthesis began with the alkylation reaction on the monoprotected TACN with the three types of chromophores: carboxylate, methyl phosphinate and phenyl phosphinate. The protective group Boc was removed and the corresponding pyridines carrying the Z identical to the chromophores were introduced at the last TACN alkylation site leading to compounds 67a-af.

Scheme 18

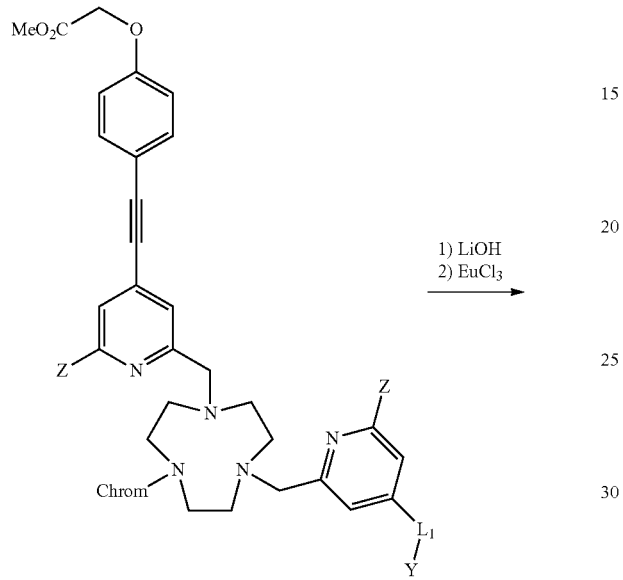

1) LiOH
2) EuCl$_3$

-continued

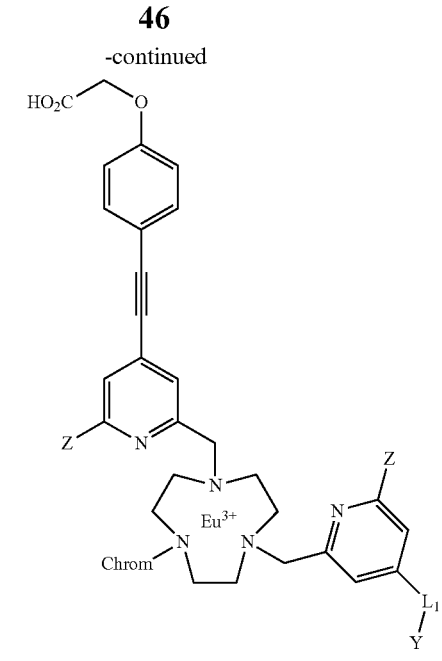

67a, Z = CO$_2$Me, L$_1$ = 0, Y = NHBoc
67b, Z = PMe(O)OEt, L$_1$ = 0, Y = NHBoc
67c, Z = PPh(O)OEt, L$_1$ = 0, Y = NHBoc
67d, Z = CO$_2$Me, L$_1$ = ——(CH$_2$)$_2$——, Y = NHBoc
67e, Z = CO$_2$Me, L$_1$ = ——(CH$_2$)$_3$——, Y = NHBoc
67f, Z = PMe(O)OEt, L$_1$ = ——(CH$_2$)$_2$——, Y = NHBoc
67g, Z = PMe(O)OEt, L$_1$ = ——(CH$_2$)$_3$——, Y = NHBoc
67h, Z = PPh(O)OEt, L$_1$ = ——(CH$_2$)$_2$——, Y = NHBoc
67i, Z = PPh(O)OEt, L$_1$ = ——(CH$_2$)$_3$——, Y = NHBoc
67j, Z = CO$_2$Me, L$_1$ = ——(CH$_2$)$_2$——, Y = CO$_2$tBu
67k, Z = CO$_2$Me, L$_1$ = ——(CH$_2$)$_3$——, Y = CO$_2$tBu
67l, Z = PMe(O)OEt, L$_1$ = ——(CH$_2$)$_2$——, Y = CO$_2$tBu
67m, Z = PMe(O)OEt, L$_1$ = ——(CH$_2$)$_3$——, Y = CO$_2$tBu
67n, Z = PPh(O)OEt, L$_1$ = ——(CH$_2$)$_2$——, Y = CO$_2$tBu
67o, Z = PPh(O)OEt, L$_1$ = ——(CH$_2$)$_3$——, Y = CO$_2$tBu
67p, Z = CO$_2$Me, L$_1$ = ——O(CH$_2$)$_3$——, Y = CO$_2$tBu
67q, Z = CO$_2$Me, L$_1$ = ——O(CH$_2$)$_3$——, Y = NHBoc
67r, Z = CO$_2$Et, L$_1$ = SCH$_2$, Y = CO$_2$tBu
67s, Z = PMe(O)OEt, L$_1$ = SCH$_2$, Y = CO$_2$tBu
67t, Z = PPh(O)OEt, L$_1$ = SCH$_2$, Y = CO$_2$tBu
67u, Z = CO$_2$Me, L$_1$ = ——CH═CH——, Y = CO$_2$tBu
67v, Z = CO$_2$Me, L$_1$ = ——CH═CH—CH$_2$——, Y = CO$_2$tBu
67w, Z = PMe(O)OEt, L$_1$ = ——CH═CH——, Y = CO$_2$tBu
67x, Z = PMe(O)OEt, L$_1$ = ——CH═CH—CH$_2$——, Y = CO$_2$tBu
67y, Z = PPh(O)OEt, L$_1$ = ——CH═CH——, Y = CO$_2$tBu
67z, Z = PPh(O)OEt, L$_1$ = ——CH═CH—CH$_2$——, Y = CO$_2$tBu
67aa, Z = CO$_2$Me, L$_1$ = ——CH═CH——, Y = NHBoc
67ab, Z = CO$_2$Me, L$_1$ = ——CH═CH—CH$_2$——, Y = NHBoc
67ac, Z = PMe(O)OEt, L$_1$ = ——CH═CH——, Y = NHBoc
67ad, Z = PMe(O)OEt, L$_1$ = ——CH═CH—CH$_2$——, Y = NHBoc
67ae, Z = PPh(O)OEt, L$_1$ = ——CH═CH——, Y = NHBoc
67af, Z = PPh(O)OEt, L$_1$ = ——CH═CH—CH$_2$——, Y = NHBoc

68a, Z = CO$_2$$^-$, L$_1$ = 0, Y = NHBoc
68b, Z = PMe(O)O$^-$, L$_1$ = 0, Y = NHBoc
68c, Z = PPh(O)O$^-$, L$_1$ = 0, Y = NHBoc
68d, Z = CO$_2$$^-$, L$_1$ = ——(CH$_2$)$_2$——, Y = NHBoc
68e, Z = CO$_2$$^-$, L$_1$ = ——(CH$_2$)$_3$——, Y = NHBoc
68f, Z = PMe(O)O$^-$, L$_1$ = ——(CH$_2$)$_2$——, Y = NHBoc
68g, Z = PMe(O)O$^-$, L$_1$ = ——(CH$_2$)$_3$——, Y = NHBoc
68h, Z = PPh(O)O$^-$, L$_1$ = ——(CH$_2$)$_2$——, Y = NHBoc
68i, Z = PPh(O)O$^-$, L$_1$ = ——(CH$_2$)$_3$——, Y = NHBoc
68j, Z = CO$_2$$^-$, L$_1$ = ——(CH$_2$)$_2$——, Y = CO$_2$tBu
68k, Z = CO$_2$$^-$, L$_1$ = ——(CH$_2$)$_3$——, Y = CO$_2$tBu
68l, Z = PMe(O)O$^-$, L$_1$ = ——(CH$_2$)$_2$——, Y = CO$_2$tBu
68m, Z = PMe(O)O$^-$, L$_1$ = ——(CH$_2$)$_3$——, Y = CO$_2$tBu
68n, Z = PPh(O)O$^-$, L$_1$ = ——(CH$_2$)$_2$——, Y = CO$_2$tBu
68o, Z = PPh(O)O$^-$, L$_1$ = ——(CH$_2$)$_3$——, Y = CO$_2$tBu
68p, Z = CO$_2$$^-$, L$_1$ = ——O(CH$_2$)$_3$——, Y = CO$_2$tBu
68q, Z = CO$_2$$^-$, L$_1$ = ——O(CH$_2$)$_3$——, Y = NHBoc
68r, Z = CO$_2$$^-$, L$_1$ = SCH$_2$, Y = CO$_2$tBu
68s, Z = PMe(O)O$^-$, L$_1$ = SCH$_2$, Y = CO$_2$tBu
68t, Z = PPh(O)O$^-$, L$_1$ = SCH$_2$, Y = CO$_2$tBu
68u, Z = CO$_2$$^-$, L$_1$ = ——CH═CH——, Y = CO$_2$tBu
68v, Z = CO$_2$$^-$, L$_1$ = ——CH═CH—CH$_2$——, Y = CO$_2$tBu
68w, Z = PMe(O)O$^-$, L$_1$ = ——CH═CH——, Y = CO$_2$tBu
68x, Z = PMe(O)O$^-$, L$_1$ = ——CH═CH—CH$_2$——, Y = CO$_2$tBu
68y, Z = PPh(O)O$^-$, L$_1$ = ——CH═CH——, Y = CO$_2$tBu
68z, Z = PPh(O)O$^-$, L$_1$ = ——CH═CH—CH$_2$——, Y = CO$_2$tBu
68aa, Z = CO$_2$$^-$, L$_1$ = ——CH═CH——, Y = NHBoc
68ab, Z = CO$_2$$^-$, L$_1$ = ——CH═CH—CH$_2$——, Y = NHBoc
68ac, Z = PMe(O)O$^-$, L$_1$ = ——CH═CH——, Y = NHBoc
68ad, Z = PMe(O)O$^-$, L$_1$ = ——CH═CH—CH$_2$——, Y = NHBoc
68ae, Z = PPh(O)O$^-$, L$_1$ = ——CH═CH——, Y = NHBoc
68af, Z = PPh(O)O$^-$, L$_1$ = ——CH═CH—CH$_2$——, Y = NHBoc

The ligands were hydrolysed and the europium atom was introduced into the macrocycle leading to series 68.

Scheme 19

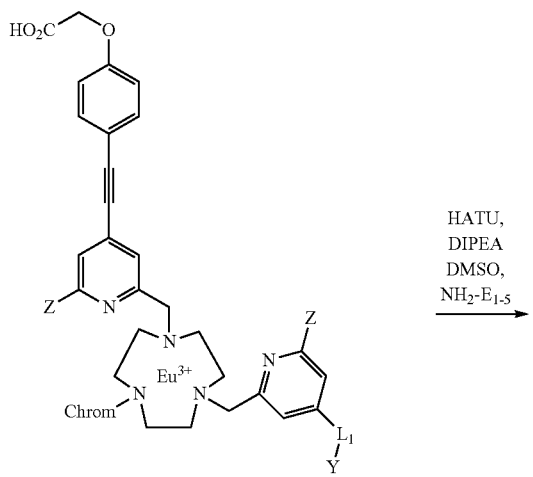

→ HATU, DIPEA DMSO, $NH_2-E_{1-5}$

68a, Z = $CO_2^-$, $L_1$ = 0, Y = NHBOC
68b, Z = PMe(O)O$^-$, $L_1$ = 0, Y = NHBOC
68c, Z = PPh(O)O$^-$, $L_1$ = 0, Y = NHBOC
68d, Z = $CO_2^-$, $L_1$ = —$(CH_2)_2$—, Y = NHBOC
68e, Z = $CO_2^-$, $L_1$ = —$(CH_2)_3$—, Y = NHBOC
68f, Z = PMe(O)O$^-$, $L_1$ = —$(CH_2)_2$—, Y = NHBOC
68g, Z = PMe(O)O$^-$, $L_1$ = —$(CH_2)_3$—, Y = NHBOC
68h, Z = PPh(O)O$^-$, $L_1$ = —$(CH_2)_2$—, Y = NHBOC
68i, Z = PPh(O)O$^-$, $L_1$ = —$(CH_2)_3$—, Y = NHBOC
68j, Z = $CO_2^-$, $L_1$ = —$(CH_2)_2$—, Y = $CO_2tBu$
68k, Z = $CO_2^-$, $L_1$ = —$(CH_2)_3$—, Y = $CO_2tBu$
68l, Z = PMe(O)O$^-$, $L_1$ = —$(CH_2)_2$—, Y = $CO_2tBu$
68m, Z = PMe(O)O$^-$, $L_1$ = —$(CH_2)_3$—, Y = $CO_2tBu$
68n, Z = PPh(O)O$^-$, $L_1$ = —$(CH_2)_2$—, Y = $CO_2tBu$
68o, Z = PPh(O)O$^-$, $L_1$ = —$(CH_2)_3$—, Y = $CO_2tBu$
68p, Z = $CO_2^-$, $L_1$ = —$O(CH_2)_3$—, Y = $CO_2tBu$
68q, Z = $CO_2^-$, $L_1$ = —$O(CH_2)_3$—, Y = NHBoc
68r, Z = $CO_2^-$, $L_1$ = $SCH_2$, Y = $CO_2tBu$
68s, Z = PMe(O)O$^-$, $L_1$ = $SCH_2$, Y = $CO_2tBu$

68t, Z = PPh(O)O$^-$, $L_1$ = $SCH_2$, Y = $CO_2tBu$
68u, Z = $CO_2^-$, $L_1$ = —CH=CH—, Y = $CO_2tBu$
68v, Z = $CO_2^-$, $L_1$ = —CH=CH-$CH_2$-, Y = $CO_2tBu$
68w, Z = PMe(O)O$^-$, $L_1$ = —CH=CH—, Y = $CO_2tBu$
68x, Z = PMe(O)O$^-$, $L_1$ = —CH=CH-$CH_2$—, Y = $CO_2tBu$
68y, Z = PPh(O)OEt, $L_1$ = —CH=CH—, Y = $CO_2tBu$
68z, Z = PPh(O)O$^-$, $L_1$ = —CH=CH-$CH_2$—, Y = $CO_2tBu$
68aa, Z = $CO_2^-$, $L_1$ = —CH=CH—, Y = NHBoc
68ab, Z = $CO_2^-$, $L_1$ = —CH=CH-$CH_2$—, Y = NHBoc
68ac, Z = PMe(O)O$^-$, $L_1$ = —CH=CH—, Y = NHBoc
68ad, Z = PMe(O)O$^-$, $L_1$ = —CH=CH-$CH_2$—, Y = NHBoc
68ae, Z = PPh(O)O$^-$, $L_1$ = —CH=CH—, Y = NHBoc
68af, Z = PPh(O)O$^-$, $L_1$ = —CH=CH-$CH_2$—, Y = NHBoc

-continued

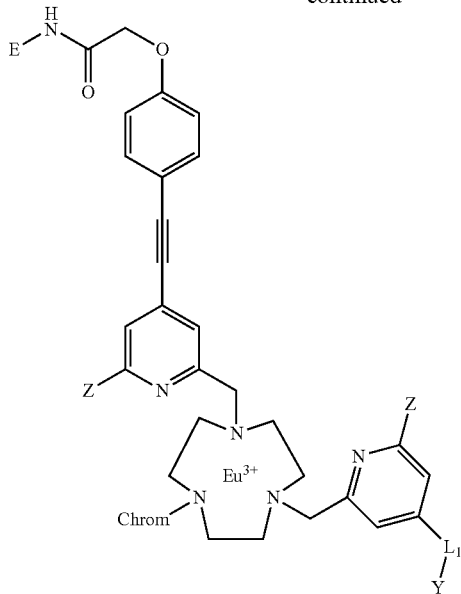
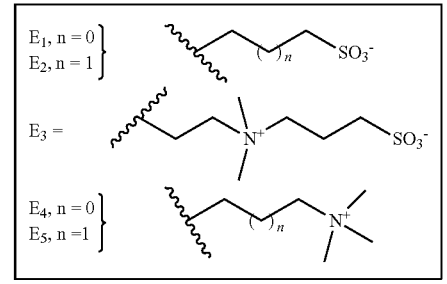

69aE$_{1-5}$, Z = CO$_2^-$, L$_1$ = 0, Y = NHBOC
69b-E$_{1-5}$, Z = PMe(O)O$^-$, L$_1$ = 0, Y = NHBOC
69c-E$_{1-5}$, Z = PPh(O)O$^-$, L$_1$ = 0, Y = NHBOC
69d-E$_{1-5}$, Z = CO$_2$, L$_1$ = —(CH$_2$)$_2$—, Y = NHBOC
69e-E$_{1-5}$, Z = CO$_2^-$, L$_1$ = —(CH$_2$)$_3$—, Y = NHBOC
69f-E$_{1-5}$, Z = PMe(O)O$^-$, L$_1$ = —(CH$_2$)$_2$—, Y = NHBOC
69g-E$_{1-5}$, Z = PMe(O)O$^-$, L$_1$ = —(CH$_2$)$_3$—, Y = NHBOC
69h-E$_{1-5}$, Z = PPh(O)O$^-$, L$_1$ = —(CH$_2$)$_2$—, Y = NHBOC
69i-E$_{1-5}$, Z = PPh(O)O$^-$, L$_1$ = —(CH$_2$)$_3$—, Y = NHBOC
69j-E$_{1-5}$, Z = CO$_2^-$, L$_1$ = —(CH$_2$)$_2$—, Y = CO$_2$tBu
69k-E$_{1-5}$, Z = CO$_2^-$, L$_1$ = —(CH$_2$)$_3$—, Y = CO$_2$tBu
69l-E$_{1-5}$, Z = PMe(O)O$^-$, L$_1$ = —(CH$_2$)$_2$—, Y = CO$_2$tBu
69m-E$_{1-5}$, Z = PMe(O)O$^-$, L$_1$ = —(CH$_2$)$_3$—, Y = CO$_2$tBu
69n-E$_{1-5}$, Z = PPh(O)O$^-$, L$_1$ = —(CH$_2$)$_2$—, Y = CO$_2$tBu
69o-E$_{1-5}$, Z = PPh(O)O$^-$, L$_1$ = —(CH$_2$)$_3$—, Y = CO$_2$tBu

69p-E$_{1-5}$, Z = CO$_2^-$, L$_1$ = —O(CH$_2$)$_3$—, Y = CO$_2$tBu
69q-E$_{1-5}$, Z = CO$_2^-$, L$_1$ = —O(CH$_2$)$_3$—, Y = NHBoc
69r-E$_{1-5}$, Z = CO$_2^-$, L$_1$ = SCH$_2$, Y = CO$_2$tBu
69s-E$_{1-5}$, Z = PMe(O)O$^-$, L$_1$ = SCH$_2$, Y = CO$_2$tBu
69t-E$_{1-5}$, Z = PPh(O)O$^-$, L$_1$ = SCH$_2$, Y = CO$_2$tBu
69u-E$_{1-5}$, Z = CO$_2^-$, L$_1$ = —CH=CH—, Y = CO$_2$tBu
69v-E$_{1-5}$, Z = CO$_2^-$, L$_1$ = —CH=CH—CH$_2$—, Y = CO$_2$tBu
69w-E$_{1-5}$, Z = PMe(O)O$^-$, L$_1$ = —CH=CH—, Y = CO$_2$tBu
69x-E$_{1-5}$, Z = PMe(O)O$^-$, L$_1$ = —CH=CH—CH$_2$—, Y = CO$_2$tBu
69y-E$_{1-5}$, Z = PPh(O)OEt, L$_1$ = —CH=CH—, Y = CO$_2$tBu
69z-E$_{1-5}$, Z = PPh(O)O$^-$, L$_1$ = —CH=CH—CH$_2$—, Y = CO$_2$tBu
69-E$_{1-5}$aa, Z = CO$_2^-$, L$_1$ = —CH=CH—, Y = NHBoc
69ab-E$_{1-5}$, Z = CO$_2^-$, L$_1$ = —CH=CH—CH$_2$—, Y = NHBoc
69ac-E$_{1-5}$, Z = PMe(O)O$^-$, L$_1$ = —CH=CH—, Y = NHBoc
69ad-E$_{1-5}$, Z = PMe(O)O$^-$, L$_1$ = —CH=CH—CH$_2$—, Y = NHBoc
69ae-E$_{1-5}$, Z = PPh(O)O$^-$, L$_1$ = —CH=CH—, Y = NHBoc
69af-E$_{1-5}$, Z = PPh(O)O$^-$, L$_1$ = —CH=CH—CH$_2$—, Y = NHBoc

The water-solubilizing groups (E$_1$-E$_5$) were then introduced on both chromophores (scheme 19). They are anionic, neutral or cationic in nature.

Scheme 20

69a-E$_{1-5}$, Z = CO$_2^-$, L$_1$ = 0, Y = NHBOC
69b-E$_{1-5}$, Z = PMe(O)O$^-$, L$_1$ = 0, Y = NHBOC
69c-E$_{1-5}$, Z = PPh(O)O$^-$, L$_1$ = 0, Y = NHBOC
69d-E$_{1-5}$, Z = CO$_2$, L$_1$ = —(CH$_2$)$_2$—, Y = NHBOC
69e-E$_{1-5}$, Z = CO$_2^-$, L$_1$ = —(CH$_2$)$_3$—, Y = NHBOC
69f-E$_{1-5}$, Z = PMe(O)O$^-$, L$_1$ = —(CH$_2$)$_2$—, Y = NHBOC
69g-E$_{1-5}$, Z = PMe(O)O$^-$, L$_1$ = —(CH$_2$)$_3$—, Y = NHBOC
69h-E$_{1-5}$, Z = PPh(O)O$^-$, L$_1$ = —(CH$_2$)$_2$—, Y = NHBOC
69i-E$_{1-5}$, Z = PPh(O)O$^-$, L$_1$ = —(CH$_2$)$_3$—, Y = NHBOC
69j-E$_{1-5}$, Z = CO$_2^-$, L$_1$ = —(CH$_2$)$_2$—, Y = CO$_2$tBu
69k-E$_{1-5}$, Z = CO$_2^-$, L$_1$ = —(CH$_2$)$_3$—, Y = CO$_2$tBu
69l-E$_{1-5}$, Z = PMe(O)O$^-$, L$_1$ = —(CH$_2$)$_2$—, Y = CO$_2$tBu
69m-E$_{1-5}$, Z = PMe(O)O$^-$, L$_1$ = —(CH$_2$)$_3$—, Y = CO$_2$tBu
69n-E$_{1-5}$, Z = PPh(O)O$^-$, L$_1$ = —(CH$_2$)$_2$—, Y = CO$_2$tBu
69o-E$_{1-5}$, Z = PPh(O)O$^-$, L$_1$ = —(CH$_2$)$_3$—, Y = CO$_2$tBu

69p-E$_{1-5}$, Z = CO$_2^-$, L$_1$ = —O(CH$_2$)$_3$—, Y = CO$_2$tBu
69q-E$_{1-5}$, Z = CO$_2^-$, L$_1$ = —O(CH$_2$)$_3$—, Y = NHBoc
69r-E$_{1-5}$, Z = CO$_2^-$, L$_1$ = SCH$_2$, Y = CO$_2$tBu
69s-E$_{1-5}$, Z = PMe(O)O$^-$, L$_1$ = SCH$_2$, Y = CO$_2$tBu
69t-E$_{1-5}$, Z = PPh(O)O$^-$, L$_1$ = SCH$_2$, Y = CO$_2$tBu
69u-E$_{1-5}$, Z = CO$_2^-$, L$_1$ = —CH=CH—, Y = CO$_2$tBu
69v-E$_{1-5}$, Z = CO$_2^-$, L$_1$ = —CH=CH—CH$_2$—, Y = CO$_2$tBu
69w-E$_{1-5}$, Z = PMe(O)O$^-$, L$_1$ = —CH=CH—, Y = CO$_2$tBu
69x-E$_{1-5}$, Z = PMe(O)O$^-$, L$_1$ = —CH=CH—CH$_2$—, Y = CO$_2$tBu
69y-E$_{1-5}$, Z = PPh(O)OEt, L$_1$ = —CH=CH—, Y = CO$_2$tBu
69z-E$_{1-5}$, Z = PPh(O)O$^-$, L$_1$ = —CH=CH—CH$_2$—, Y = CO$_2$tBu
69-E$_{1-5}$aa, Z = CO$_2^-$, L$_1$ = —CH=CH—, Y = NHBoc
69ab-E$_{1-5}$, Z = CO$_2^-$, L$_1$ = —CH=CH—CH$_2$—, Y = NHBoc
69ac-E$_{1-5}$, Z = PMe(O)O$^-$, L$_1$ = —CH=CH—, Y = NHBoc
69ad-E$_{1-5}$, Z = PMe(O)O$^-$, L$_1$ = —CH=CH—CH$_2$—, Y = NHBoc
69ae-E$_{1-5}$, Z = PPh(O)O$^-$, L$_1$ = —CH=CH—, Y = NHBoc
69af-E$_{1-5}$, Z = PPh(O)O$^-$, L$_1$ = —CH=CH—CH$_2$—, Y = NHBoc

-continued

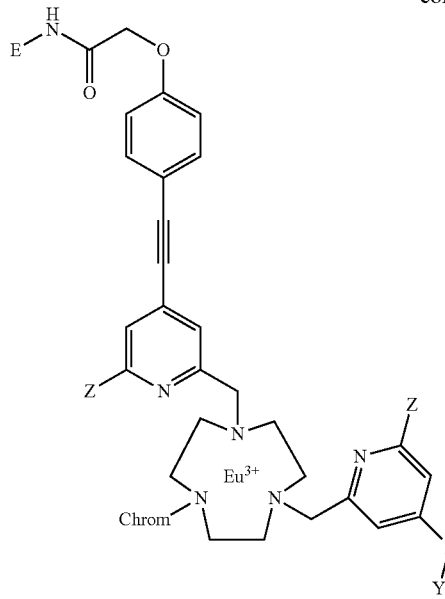

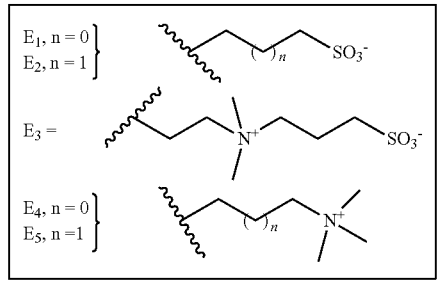

70a-$E_{1-5}$, Z = $CO_2^-$, $L_1$ = 0, Y = $NH_2$
70b-$E_{1-5}$, Z = PMe(O)$O^-$, $L_1$ = 0, Y = $NH_2$
70c-$E_{1-5}$, Z = PPh(O)$O^-$, $L_1$ = 0, Y = $NH_2$
70d-$E_{1-5}$, Z = $CO_2$, $L_1$ = —$(CH_2)_2$—, Y = $NH_2$
70e-$E_{1-5}$, Z = $CO_2^-$, $L_1$ = —$(CH_2)_3$—, Y = $NH_2$
70f-$E_{1-5}$, Z = PMe(O)$O^-$, $L_1$ = —$(CH_2)_2$—, Y = $NH_2$
70g-$E_{1-5}$, Z = PMe(O)$O^-$, $L_1$ = —$(CH_2)_3$—, Y = $NH_2$
70h-$E_{1-5}$, Z = PPh(O)$O^-$, $L_1$ = —$(CH_2)_2$—, Y = $NH_2$
70i-$E_{1-5}$, Z = PPh(O)$O^-$, $L_1$ = —$(CH_2)_3$—, Y = $NH_2$
70j-$E_{1-5}$, Z = $CO_2^-$, $L_1$ = —$(CH_2)_2$—, Y = $CO_2H$
70k-$E_{1-5}$, Z = $CO_2^-$, $L_1$ = —$(CH_2)_3$—, Y = $CO_2H$
70l-$E_{1-5}$, Z = PMe(O)$O^-$, $L_1$ = —$(CH_2)_2$—, Y = $CO_2H$
70m-$E_{1-5}$, Z = PMe(O)$O^-$, $L_1$ = —$(CH_2)_3$—, Y = $CO_2H$
70n-$E_{1-5}$, Z = PPh(O)$O^-$, $L_1$ = —$(CH_2)_2$—, Y = $CO_2H$
70o-$E_{1-5}$, Z = PPh(O)$O^-$, $L_1$ = —$(CH_2)_3$—, Y = $CO_2H$
70p-$E_{1-5}$, Z = $CO_2^-$, $L_1$ = —O$(CH_2)_3$—, Y = $CO_2H$
70q-$E_{1-5}$, Z = $CO_2^-$, $L_1$ = —O$(CH_2)_3$—, Y = $NH_2$
70r-$E_{1-5}$, Z = $CO_2^-$, $L_1$ = $SCH_2$, Y = $CO_2H$
70s-$E_{1-5}$, Z = PMe(O)$O^-$, $L_1$ = $SCH_2$, Y = $CO_2H$
70t-$E_{1-5}$, Z = PPh(O)$O^-$, $L_1$ = $SCH_2$, Y = $CO_2H$
70u-$E_{1-5}$, Z = $CO_2^-$, $L_1$ = —CH=CH—, Y = $CO_2H$
70v-$E_{1-5}$, Z = $CO_2^-$, $L_1$ = —CH=CH—$CH_2$—, Y = $CO_2H$
70w-$E_{1-5}$, Z = PMe(O)$O^-$, $L_1$ = —CH=CH—, Y = $CO_2H$
70x-$E_{1-5}$, Z = PMe(O)$O^-$, $L_1$ = —CH=CH—$CH_2$—, Y = $CO_2H$
70y-$E_{1-5}$, Z = PPh(O)OEt, $L_1$ = ——CH=CH—, Y = $CO_2H$
70z-$E_{1-5}$, Z = PPh(O)$O^-$, $L_1$ = ——CH=CH—$CH_2$—, Y = $CO_2H$
70-$E_{1-5}$aa, Z = $CO_2^-$, $L_1$ = ——CH=CH—, Y = $NH_2$
70ab-$E_{1-5}$, Z = $CO_2^-$, $L_1$ = ——CH=CH—$CH_2$—, Y = $NH_2$
70ac-$E_{1-5}$, Z = PMe(O)$O^-$, $L_1$ = ——CH=CH—, Y = $NH_2$
70ad-$E_{1-5}$, Z = PMe(O)$O^-$, $L_1$ = ——CH=CH—$CH_2$—, Y = $NH_2$
70ae-$E_{1-5}$, Z = PPh(O)$O^-$, $L_1$ = ——CH=CH—, Y = $NH_2$
70af-$E_{1-5}$, Z = PPh(O)$O^-$, $L_1$ = ——CH=CH—$CH_2$—, Y = $NH_2$

Finally, the Boc or tert-butyl ester group was then removed in the presence of trifluoroacetic acid to give compounds 70a-af (scheme 20).

EXPERIMENTAL PART

Abbreviations Used

AcOEt: ethyl acetate
AcOH: acetic acid
Boc: tert-butyloxycarbonyl
TLC: thin-layer chromatography
$CDCl_3$: deuterated chloroform
$CHCl_3$: chloroform
$CsCO_3$: caesium carbonate
CuI: copper(I) iodide
$CH_2Cl_2$/DCM: dichloromethane
DIAD: diisopropyl azodicarboxylate
DIPEA: diisopropylethylamine
DMF: dimethylformamide DMSO: dimethylsulphoxide
Et: ethyl
Et₃N/TEA: triethylamine
ESI+: electrospray ionization in positive mode
EtOH: ethanol
D: day
HATU: (O-(7-azabenzotriazol-1-yl)-N,N,N',N'-tetramethyluronium hexafluorophosphate)
H$_2$O: water
H$_2$SO$_4$: sulfuric acid
HNO$_3$: nitric acid
HPLC: high-performance liquid chromatography
LC-MS: high performance liquid chromatography coupled to mass spectrometry
LiOH/Lithine: lithium hydroxide
LnCl$_3$: lanthanide chloride
m-CPBA: metachloroperbenzoic acid
Me: methyl
MeCN: acetonitrile
MeOH: methanol
MgSO$_4$: magnesium sulphate
Ms: mesyl
MsCl: mesyl chloride
NaCl: sodium chloride
NaH: sodium hydride
Pd(dppf)Cl$_2$: bis(diphenylphosphino)ferrocene]dichloropalladium(II)
Pd(PPh$_3$)$_4$: tetrakis(triphenylphosphine)palladium(O)
Pd/C: Palladium on charcoal
Pd(OAc)$_2$: palladium(II) acetate
Ph: phenyl
PPh$_3$: triphenylphosphine
PtF: melting point
Py: pyridine
Rf: solvent front
Rt: retention time
RT: room temperature
tBu: tert-butyl
TEA: triethylamine
TFA: trifluoroacetic acid
THF: tetrahydrofuran
TMS: trimethylsilyl
Ts: tosyl
TSTU: O—(N-Succinimidyl)-1,1,3,3-tetramethyluronium tetrafluoroborate
UPLC-MS: ultra-high-performance liquid chromatography coupled to mass spectrometry
Xphos: 2-dicyclohexylphosphino-2',4',6'-triisopropylbiphenyl.

Chromatography

Thin-layer chromatography was performed on Merck 60 F$_{254}$ silica gel plates on aluminium foil or on Merck 60 F$_{254}$ neutral aluminium oxide plates (type E) on aluminium foil.

Analytical and preparative High-performance liquid chromatography (HPLC) was performed on two devices:

Analytical HPLC: ThermoScientific, quaternary pump P4000, UV detector 1000 with deuterium lamp (190-350 nm), analytical column Waters XBridge C$_{18}$, 3.5 μm, 4.6×100 mm.

Preparative HPLC: Shimadzu, 2 LC-8A pumps, Varian ProStar diode array UV detector, Waters XBridge preparative column C$_{18}$, 5 μm: 19×100 mm or 50×150 mm.

Analytical ultra-high-performance liquid chromatography (UPLC) was performed on a Waters Acquity HClass device with either a UV diode strip detector of the PDA type or a simple quadrupole mass detector of the SQD2 type as the detector. The probe used is an electro-spray in positive mode: capillary voltage at 3.2 kV—cone voltage at 30 V.

Silica column chromatography was performed on Merck 60 silica gel (0.040-0.063 mm). Alumina column chromatography was performed on Sigma-Aldrich aluminium oxide, neutral, activated, Brochmann I.

Gradient A
Waters Acquity C$_{18}$ column, 300 Å, 1.7 μm, 2.1×50 mm—A/water 0.1% formic acid B/acetonitrile 0.1% formic acid t=0 min 5% B—t=0.2 min 5% B—t=5 min 100% B—0.6 mL/min.

Gradient B
Waters Xbridge C$_{18}$ column, 5 μm, 50×150 mm—A/water 25 mM TEAAc pH 7 B/acetonitrile t=0 min 10% B—t=19 min 60% B—100 mL/min.

Gradient C
Waters Acquity C$_{18}$ column, 300 Å, 1.7 μm, 2.1×50 mm—A/water 5 mM ammonium acetate B/acetonitrile t=0 min 5% B—t=0.2 min 5% B—t=5 min 100% B—0.6 mL/min.

Gradient D
Waters Xbridge C$_{18}$, 5 μm, 20×100 mm—A/water 25 mM TEAAc pH 7 B/acetonitrile t=0 min 5% B—t=19 min 60% B—20 mL/min.

Gradient E
Waters Xbridge C$_{18}$, 5 μm, 20×100 mm—A/water 25 mM TEAAc pH 7 B/acetonitrile t=0 min 2% B—t=19 min 40% B—20 mL/min.

Gradient F
Waters Xbridge C$_{18}$, 5 μm, 20×100 mm—A/water 25 mM TEAAc pH 6 B/acetonitrile t=0 min 2% B—t=19 min 40% B—20 mL/min.

Spectroscopy
Nuclear Magnetic Resonance

The NMR spectra ($^1$H, $^{13}$C and $^{31}$P) were performed using a Bruker Avance 400 MHz NanoBay spectrometer (9.4 teslas magnet), equipped with a BBFO, multicore 5 mm diameter, Z gradient and lock$^2$H measurement probe. Chemical shifts (δ) are expressed in parts per million (ppm). The following abbreviations are used:

s: singlet, br: broad singlet, d: doublet, t: triplet, q: quadruplet, m: multiplet, dd: doublet of doublets, td: triplet of doublets, qd: quadruplet of doublets, ddd: doublet of doublets of doublets.

Mass Spectrometry (LRMS)

The mass spectra (LC-MS) were performed using a single quadrupole Waters ZQ 2000 spectrometer with multimode ESI/APCI source equipped with Waters XBridge C$_{18}$, 3.5 μm, 4.6×100 mm column or a single quadrupole mass spectrometer of the SQD2 type.

High Resolution Mass Spectrometry (HRMS)

The analyses were performed with a QStar Elite mass spectrometer (Applied Biosystems SCIEX) equipped with a pneumatically assisted atmospheric pressure ionization (API) source. The sample was ionized in positive electrospray mode under the following conditions: electrospray voltage (ISV): 5500 V; orifice voltage (OR): 20 V; nebulizer gas pressure (air): 20 psi. The high-resolution mass spectrum (HRMS) was obtained with a time of flight analyser (TOF). The exact mass measurement was performed in triplicate with a double internal calibration.

EXAMPLES

Compound 1: Compound 1 was prepared according to the procedure described in applications WO 2013/011236 and WO 2014/111661.

Compounds 14a-14c: Compounds 14a-14c were prepared according to the procedure described in applications WO 2013/011236 and WO 2014/111661.

Compound 15a: in a 100 mL Schlenk flask, compound 14a (440 mg, 1.5 mmol) was solubilized in anhydrous DMF (10 mL) to give a colourless solution. To the reaction mixture was added tri(o-tolyl)phosphine (91 mg, 0.3 mmol), Pd(OAc)$_2$ (33.7 mg, 0.15 mmol), TEA (0.314 ml, 2.252 mmol) and methyl acrylate (0.203 mL, 2.252 mmol) all at once. The reaction was stirred at 70° C. for 5 hours. The progress of the reaction was monitored by UPLC-MS (gradient A). After this period, the reaction was complete. The reaction mixture was concentrated under reduced pressure, diluted in AcOEt (50 mL), washed with water (2×50 mL) and then water saturated with NaCl (50 mL). The organic phase was dried over MgSO$_4$, filtered and concentrated under reduced pressure. The crude product was purified by silica column chromatography using a DCM/MeOH solvent gradient of 100/0 to 99/1 to yield compound 15a (233 mg, 62%) in white powder form.

Pf=156.4-156.9° C.—HPLC gradient A—Rt=2.03 min—[M+H]$^+$, m/z 251.9—Rf=0.41 (silica, dichloromethane-methanol 96:4—HRMS (ESI+) calculated for $C_{12}H_{14}NO_5^+$ [M+H]$^+$, m/z 252.0868—found: 252.0866—$^1$H NMR (400 MHz, CDCl$_3$) δ: 8.13 (s, 1H, Py H$^5$), 7.67 (d, J=16.2 Hz, 1H), 7.65 (s, 1H, Py H$^3$), 7.19 (dd, J=; 16.2 Hz, 2H, HC=CH), 6.71 (d, J=16.2 Hz, 1H), 4.91 (s, 2H, CH$_2$—OH), 4.04 (s, 3H, Py-COOMe), 3.85 (s, 3H, COOMe), 3.49 (s 1, 1H, OH); $^{13}$C NMR (100 MHz, CDCl$_3$) δ: 166.20 (COOMe), 165.24 (Py-COOMe), 161.59 (Py C$^2$), 147.97 (Py-C=C), 143.74 (Py C$^6$), 140.92 (Py C$^4$), 123.77 (Py C$^3$), 122.08 (Py C$^5$), 121.86 (Py-C=C), 64.68 (CH$_2$—OH), 53.10 (Py-CO$_2$CH$_3$), 52.19 (CO$_2$CH$_3$).

Compounds 15b-15f: these compounds were prepared according to the same procedure as that used for the synthesis of 15a using the corresponding alkenes.

Compound 16a: in a 50 mL flask, compound 15a (233 mg, 0.927 mmol) was solubilized in MeOH (10 mL) to give a colourless solution. To the reaction mixture was added 10% Pd/C (23.69 mg, 0.022 mmol) all at once. The reaction was stirred at RT with bubbled dihydrogen for 2 hours. The progress of the reaction was monitored by UPLC-MS (gradient A). After this period, the reaction was complete. The reaction mixture was filtered through a 22 μm nylon filter, evaporated to dryness to give compound 16a (231 mg, 98%) in white powder form. Pf=133.2-136.4° C.—HPLC gradient A—Rt=1.86 min—[M+H]$^+$, m/z 253.2—HRMS (ESI+) calculated for $C_{12}H_{16}NO_5^+$ [M+H]$^+$, m/z 254.1023, found: 254.1024—$^1$H NMR (400 MHz, CDCl$_3$) δ: 7.9 (s, 1H, Py H$^5$), 7.41 (s, 1H, Py H$^3$), 4.85 (s, 2H, CH$_2$—OH), 4.01 (s, 3H, Py-COOMe), 3.69 (s, 3H, COOMe), 3.05 (t, J=7.6 Hz, 2H, Py-CH$_2$—CH$_2$), 2.71 (t, J=7.6 Hz, 2H, Py-CH$_2$—CH$_2$); $^{13}$C NMR (100 MHz, CDCl$_3$) δ: 172.41 (COOMe), 165.65 (Py-COOMe), 160.49 (Py C$^2$), 151.67 (Py C$^4$), 147.22 (Py C$^6$), 140.92 (Py C$^3$), 123.96 (Py C$^3$), 123.9 (Py C$^5$), 64.62 (CH$_2$—OH), 52.91 (Py-CO$_2$CH$_3$), 51.91 (CO$_2$CH$_3$), 33.97 (Py-CH$_2$—CH$_2$), 30.07 (Py-CH$_2$—CH$_2$).

Compounds 16b-16f: these compounds were prepared according to the same procedure as that used for the synthesis of 16a.

Compound 17a: in a 100 mL flask, compound 16a (231 mg, 0.912 mmol) was solubilized in anhydrous THF (30 mL) to give a colourless solution. To the reaction mixture placed in an ice bath, TEA (0.127 mL, 0.912 mmol) and MsCl (72 μL, 0.912 mmol) were added all at once. The mixture was warmed to RT and stirred for 15 minutes. The progress of the reaction was monitored by UPLC-MS (gradient A). After this period, the reaction was complete. The reaction mixture was concentrated under reduced pressure, diluted in DCM (50 mL), washed with water (2×25 mL) and then water saturated with NaCl (20 mL). The organic phase was dried over MgSO$_4$, filtered and concentrated under reduced pressure to yield compound 17a (249 mg, 82%) in white powder form. HPLC gradient A—Rt=3.2 min—[M+H]$^+$, m/z 332.3—Rf=0.23 (silica, dichloromethane-methanol 98:2—HRMS (ESI+) calculated for $C_{13}H_{18}NO_7S^+$ [M+H]$^+$, m/z 332.0799, found: 332.0799—$^1$H NMR (400 MHz, CDCl$_3$) δ: 7.98 (s, 1H, Py H$^5$), 7.54 (s, 1H, Py H$^3$), 5.41 (s, 2H, CH-OMs), 4.00 (s, 3H, Py-COOMe), 3.69 (s, 3H, COOMe), 3.16 (s, 3H, OMs), 3.07 (t, J=7.5 Hz, 2H, Py-CH$_2$—CH$_2$), 2.72 (t, J=7.5 Hz, 2H, Py-CH$_2$—CH$_2$); $^{13}$C NMR (100 MHz, CDCl$_3$) δ: 172.23 (COOMe), 165.27 (Py-COOMe), 154.56 (Py C$^2$), 152.46 (Py C$^4$), 147.93 (Py C$^6$), 125.19 (Py C$^3$), 125.03 (Py C$^5$), 70.97 (CH$_2$-OMs), 53.08 (Py-CO$_2$CH$_3$), 51.94 (CO$_2$CH$_3$), 38.05 (CH$_2$—OSO$_2$CH$_3$), 33.87 (Py-CH$_2$—CH$_2$), 30.07 (Py-CH$_2$—CH$_2$).

Compounds 17b-17f: these compounds were prepared according to the same procedure as that used for the synthesis of 16a.

Compounds 18a-18f: these compounds were prepared according to the same procedure as that used for the synthesis of 17a.

Compounds 19a-19f: these compounds were prepared according to the same procedure as that used for the synthesis of 15a.

Compounds 20a-20f: these compounds were prepared according to the same procedure as that used for the synthesis of 16a.

Compounds 21a-21f: these compounds were prepared according to the same procedure as that used for the synthesis of 17a.

Compounds 22a-22f: these compounds were prepared according to the same procedure as that used for the synthesis of 17a.

Compounds 23a-23f: these compounds were prepared according to the same procedure as that used for the synthesis of 15a using the corresponding alkenes.

Compounds 24a-24f: these compounds were prepared according to the same procedure as that used for the synthesis of 16a.

Compounds 25a-25f: these compounds were prepared according to the same procedure as that used for the synthesis of 17a.

Compounds 26a-26f: these compounds were prepared according to the same procedure as that used for the synthesis of 17a.

Compound 27a-c: compounds 27a-c were prepared according to the procedure described in the article: Tetrahedron Letters 2010, 51, 4445.

Compounds 28a-28c: these compounds were prepared according to the same procedure as that used for the synthesis of 17a.

Compound 29: this compound is commercially available.

Compound 30: compound 30 was prepared according to the procedure described in the article: Dalton Transactions 2010, 39, 707.

Compounds 31a-31c: compounds 31a-31c were prepared according to the procedure described in the article: Organic Biomolecular Chemistry 2012, 10, 9183.

Compounds 32a-32c: compounds 32a-32c were prepared according to the procedure described in the article: Journal of Organic Chemistry 2010, 75, 7175.

Compounds 33a-33c: compounds 33a-33c were prepared according to the procedure described in the article: Journal of Organic Chemistry 2010, 75, 7175.

Compound 34: this compound is commercially available.

Compound 35: compound 35 was prepared according to the procedure described in the article: Bioorganic Chemistry 2014, 57, 148.

Compound 36: compound 36 was prepared according to the procedure described in the article: Carbohydrate Research 2013, 372, 35.

Compound 37: compound 37 was prepared according to the procedure described in WO 2014/111661.

Compound 38: the compound was prepared according to the same procedure as that used for the synthesis of 17a.

Compound 39: this compound is commercially available.

Compound 40: Compound 40 was prepared according to the procedure described in the article: Bioorganic Chemistry 2014, 57, 148.

Compound 41a-b: compounds 41a-b were prepared according to the procedure described in application WO 2014/111661 using the corresponding catalyst.

Compound 42a-b: compounds 42a-b were prepared according to the same procedure as that used for the synthesis of 36.

Compound 43a-b: compounds 43a-b were prepared according to the same procedure as that used for the synthesis of 37.

Compound 44a-b: compounds 44a-b were prepared according to the same procedure as that used for the synthesis of 17a.

Compound 45: commercially available.

Compound 46: compound 46 was prepared according to the procedure described in the article: Chemistry—A European Journal, 2014, 20, 3610.

Compound 47: compound 46 (0.313 g, 2.04 mmol) was dissolved in $H_2SO_4$ (11 mL) at RT and then the solution was cooled in an ice bath. To this mixture $HNO_3$ (9.7 mL) was added dropwise and the solution was heated to 100° C. for 2 days. The mixture was cooled to RT and then poured into crushed ice (100 g). After 1 hour, the aqueous phase was extracted with $CH_2Cl_2$ (3×50 mL), the organic phases were combined, dried over $MgSO_4$ and the crude product was purified by silica column chromatography using a solvent mixture ($CH_2Cl_2$—AcOH, 98/2) to give a white solid (224 mg, 56%). $R_f$ ($CH_2Cl_2$/AcOH, 98/2)=0.38; PtF: 147° C.; $^1$H NMR (400 MHz, $CDCl_3$, δ): 16.49 (s, 1H, COO$\underline{H}$), 9.08 (s, 1H, $H^3$), 8.36 (s, 1H, $H^5$), 2.75 (s, 3H, py-$CH_3$); $^{13}$C NMR (101 MHz, $CDCl_3$, δ): 159.4 (COOH), 152.4 ($C^6$), 144.4 ($C^4$), 138.7 ($C^2$), 123.1 ($C^5$), 121.7 ($C^3$), 18.4 (py-$CH_3$); MS Calculated for $C_7H_7N_2O_5$ 199.036. Found 199.035 [M+H]$^+$.

Compound 48: compound 47 (2.9, 14.7 mmol) was dissolved in anhydrous MeOH (3 mL) at RT. To this solution $H_2SO_4$ (200 μL) was added dropwise and the solution was heated to 65° C. for 3 days. The solution was cooled to RT and the solvent was removed under reduced pressure. $H_2O$ (30 mL) was added to the residue and the solution was extracted with AcOEt (3×20 mL). The organic phases were combined, washed with a 5% sodium bicarbonate solution (2×20 mL) and then with a saturated brine solution (20 mL). After drying over $MgSO_4$, the solvent was filtered, removed under reduced pressure to yield compound 48 which was used in subsequent synthesis without further purification (57 mg, 76%). $^1$H NMR (400 MHz, $CDCl_3$, δ): 8.33 (d, 1H, $^4$J 3.1, $H^5$), 8.19 (d, 1H, $^4$J 3.1, $H^3$), 4.02 (s, 3H, $CH_3$CO), 2.57 (s, 3H, py-$CH_3$); $^{13}$C NMR (100 MHz, $CDCl_3$, δ): 160.8 (COOMe), 152.7 ($C^6$), 142.1 ($C^4$), 140.5 ($C^2$), 121.4 ($C^5$), 119.3 ($C^3$), 53.8 ($OCH_3$), 18.3 (py-$CH_3$); MS Calculated $C_8H_9N_2O_5$ 213.051. Found 213.050 [M+H]$^+$.

Compound 49: trifluoroacetic anhydride (1.48 mL, 10 mL) was added at RT to a solution of compound 48 (114 mg, 0.54 mmol) in $CHCl_3$ (10 mL). The mixture was heated to 60° C. for 5 hours in an inert atmosphere. After this period, the reaction was cooled to RT and the solvent was removed under reduced pressure. To the yellow oil, EtOH (3 mL) and $H_2O$ (3 mL) were added and the solution was stirred at RT for 2 hours. The solvents were removed under reduced pressure and the aqueous phase was extracted with $CH_2Cl_2$ (3×30 mL). The organic phases were combined, dried over $MgSO_4$ and evaporated under reduced pressure. The residue was purified by silica column chromatography using a gradient of Hexane/AcOEt solvent, 70/30 to 50/50 to yield compound 49 (74 mg, 65%). $R_f$ ($CH_2Cl_2$/MeOH, 95/5) =0.67; $^1$H NMR (400 MHz, $CDCl_3$, δ): 8.68 (d, 1H, $^4$J 2.1, $H^3$), 8.37 (d, 1H, $^4$J 2.1, $H^5$), 5.06 (s, 2H, $CH_2$OH), 4.06 (s, 3H, $C\underline{H_3}$CO); $^{13}$C NMR (100 MHz, $CDCl_3$, δ): 164.3 (COOMe), 163.6 ($C^6$), 155.3 ($C^4$), 149.7 ($C^2$), 116.4 ($C^5$), 116.3 ($C^3$), 64.5 ($CH_2$OH), 29.5 ($CO_2CH_3$).

Compound 50a: NaH (17 mg, 0.708 mmol) and ethyl thioglycolate (35 μL, 0.320 mmol) were added to a solution of compound 49 (21.6 mg, 0.102 mmol) in anhydrous DMF (1 mL) under inert atmosphere and at RT. The mixture was stirred at RT for 2 hours in an inert atmosphere. The solvent was then removed under reduced pressure and MeOH (5 mL) and $H_2SO_4$ (200 μL) were added to the yellow oil. The solution was heated to 65° C. for 72 hours under argon. The solvent was removed under reduced pressure and $H_2O$ (10 mL) was added to the residue, and the aqueous solution was extracted with AcOEt (3×20 mL). The organic phases were combined and dried over $MgSO_4$, filtered and concentrated under reduced pressure. The residue was purified by silica column chromatography using as eluent $CH_2Cl_2$-MeOH, 98/2 leading to compound 50a (8.2 mg, 25%). $R_f$(DCM/MeOH, 95/5)=0.35; $^1$H NMR (400 MHz, $CDCl_3$, δ): 7.88 (d, 1H, $^4$J 1.9, $H^5$), 7.63 (d, 1H, $^4$J 1.9, $H^3$), 4.69 (s, 2H, $CH_2$OH), 4.02 (s, 2H, $C\underline{H_2}$S), 3.96 (s, 3H, $CH_3$CO), 3.76 (s, 3H, $CH_3$CO); $^{13}$C NMR (100 MHz, $CDCl_3$, δ): 170.7 (COOMe), 166.4 (COOMe), 163.3 ($C^2$), 152.3 ($C^4$), 147.8 ($C^6$), 121.2 ($C^5$), 121.1 ($C^3$), 65.1 ($CH_2$OH), 53.3 ($CO_2C\underline{H_3}$), 48.5 ($CO_2CH_3$), 33.6 ($SCH_2$).

Compound 50b: compound 50b was prepared according to the same procedure as that used for the synthesis of 50a.

Compound 51a: triethylamine (12.5 μL, 0.09 mmol) and MsCl (3.5 μL, 0.045 mmol) were added to a solution of compound 50a (8.2 mg, 0.03 mmol) in anhydrous THF (2 mL). This solution was stirred at RT for 3.5 hours. After this period, the solvent was removed under reduced pressure and the residue dissolved in $CH_2Cl_2$ (20 mL). The organic phase was washed with $H_2O$ (3×10 mL), dried over $MgSO_4$, filtered and the solvent was removed under reduced pressure to quantitatively yield compound 51a. $R_f$ (DCM/MeOH, 95/5)=0.8; $^1$H NMR (400 MHz, $CDCl_3$, S): 7.95 (d, 1H, $^4$J 1.5, $H^5$), 7.52 (d, 1H, $^4$J 1.5, $H^3$), 5.35 (s, 2H, $CH_2$OMs), 3.98 (s, 2H, $CH_2$S), 3.82 (s, 2H, $COCH_3$), 3.77 (s, 2H, $COCH_3$), 3.14 (s, 3H, $SCH_3$).

Compound 51b: compound 51b was prepared according to the same procedure as that used for the synthesis of 51a.

Compounds 52a-b: compounds 52a-b were prepared according to the same procedures as those used for the synthesis of 14b and 14c respectively.

Compounds 53a-b: compounds 53a-b were prepared according to the same procedure as that used for the synthesis of 46.

Compounds 54a-b: compounds 54a-b were prepared according to the same procedure as that used for the synthesis of 49.

Compounds 55a-d: compounds 55a-d were prepared according to the same procedure as that used for the synthesis of 50a.

Compounds 56a-d: compounds 56a-d were prepared according to the same procedure as that used for the synthesis of 51a.

Compound 57a: compound 57a was prepared according to the same procedure as that used for the synthesis of 57b using pyridine 14a.

Compound 57b: anhydrous THF (1 mL) was added to the brominated derivative 14b (103 mg, 0.35 mmol) and the solution was degassed by three freeze-thaw cycles. To this solution were added acetylenic derivative (80 mg, 0.42 mmol) and TEA (0.24 mL, 1.75 mmol) and the solution was degassed again. To this solution were added Pd(dppf)Cl$_2$ (30 mg, 0.035 mmol) and CuI (7 mg, 0.035 mmol). This new solution was degassed again three times and then stirred at 65° C. in an inert atmosphere. The progress of the reaction was monitored by TLC. After 18 hours the reaction was complete. The reaction mixture was cooled to RT and the solvent was removed under reduced pressure. The crude product was purified by silica column chromatography (DCM/MeOH 0 to 3% in 0.1% increments) to obtain a yellow oil corresponding to compound 57b (122 mg, 87%). $^1$H NMR (400 MHz, CDCl$_3$) δ: 7.98 (s 1, 1H), 7.50 (s 1, 1H), 7.45 (d, J=8.9 Hz, 2H), 6.88 (d, J=8.9 Hz, 2H), 4.80 (s, 2H), 4.65 (s, 2H), 4.09 (m, 1H), 3.99 (s 1, 1H), 3.86 (m, 1H), 3.79 (s, 3H), 1.76 (d, J=14.9 Hz, 3H), 1.26 (t, J=6.9 Hz, 3H); $^{13}$C NMR (100 MHz, CDCl$_3$) δ: 168.9; 161.0 (d, J=19 Hz), 158.8; 153.3 (d, J=155 Hz), 133.8; 132.9 (d, J=12 Hz), 128.1 (d, J=22 Hz), 124.2; 115.1; 115.0; 95.7; 85.6; 65.2; 64.3; 61.3 (d, J=5 Hz), 52.5; 16.5 (d, J=4 Hz), 13.5 (d, J=104 Hz); $^{31}$P NMR (162 MHz, CDCl$_3$) δ: +39.5. HRMS (ESI+) calculated for C$_{20}$H$_{22}$NNaO$_6$P [M+Na]$^+$, m/z 426.1082 found: 426.1063. Rf=0.44 (silica; DCM-MeOH 90:10).

Compound 57c: compound 57c was prepared according to the same procedure as that used for the synthesis of 57b using pyridine 14c.

Compound 59a: a solution of acetylene derivative (0.864 g, 3.1 mmol) and iodine derivative 14a (0.735 g, 2.5 mmol) in a mixture of anhydrous THF (20 mL) and TEA (20 mL) was degassed under stirring for 20 minutes. To this solution were added palladium(II) bis-chloride bis-triphenylphosphine (22 mg, 0.031 mmol) and CuI (12 mg, 0.063 mmol). The reaction was stirred at RT for 12 hours. The progress of the reaction was monitored by TLC. After this period the reaction was complete. Solvents were removed under reduced pressure. To the residue was added a saturated ammonium chloride solution (50 mL) and the mixture was extracted with DCM (2×25 mL). The organic phases were combined, washed with a saturated ammonium chloride solution (50 mL), then with a saturated NaCl solution (2×50 mL) and then dried over MgSO$_4$. After filtration the solvent was removed under reduced pressure and the residue was purified by silica column chromatography (DCM/MeOH 98/2) to yield compound 59a as a white solid (0.91 g, 82%). PtF: 143-144° C. $^1$H NMR (500 MHz, CDCl$_3$) δ: 8.04 (s, 1H), 7.58 (s, 1H), 7.45 (d, J=8.7 Hz, 2H), 6.86 (d, J=8.7 Hz, 2H), 4.83 (d, J=5.4 Hz, 2H), 4.75 (s, 1H), 4.01 (t, J=6.1 Hz, 2H), 3.97 (s, 3H), 3.31 (td, J=6.1; 6.1 Hz, 2H), 1.96 (m, J=6.1 Hz, 2H), 1.41 (s, 9H). $^{13}$C NMR (125 MHz, CDCl$_3$) δ: 165.4; 160.8; 160.1; 156.2; 147.3; 134.1; 133.8; 125.8; 125.4; 114.9; 113.9; 95.9; 85.4; 66.1; 64.8; 53.2; 38.1; 29.7; 28.6. HRMS (ESI+) calculated for C$_{24}$H$_{28}$N$_2$O$_6$ [M+H]$^+$, m/z 441.2020, found: 441.2021. Rf=0.32 (silica, DCM-MeOH 96:4).

Compound 59b: anhydrous THF (10 mL) was added to the brominated derivative 14b (200 mg, 0.68 mmol) and the solution was degassed by three freeze-thaw cycles. To this solution were added acetylenic derivative (260 mg, 0.75 mmol) and TEA (5 mL) and the solution was degassed again. To this solution were added Pd(PPh$_3$)$_4$ (79 mg, 0.068 mmol) and CuI (13 mg, 0.068 mmol). This new solution was degassed again three times and then stirred at 65° C. in an inert atmosphere. The progress of the reaction was monitored by TLC. After 1 hour the reaction was complete. The reaction mixture was cooled to RT and the solvent was removed under reduced pressure. The residue was diluted in DCM (25 mL) and washed with a saturated aqueous solution of ammonium chloride (25 mL) and then with water (25 mL). The organic phase was dried over MgSO$_4$, filtered and concentrated under reduced pressure to produce a residue that was purified by silica column chromatography (DCM/MeOH 0 to 5% in 1% increments) to obtain a yellow oil corresponding to compound 59b (220 mg, 66%). HRMS (ESI+) calculated for C$_{25}$H$_{34}$N$_2$O$_6$P [M+H]$^+$, m/z 489.2149 found: 489.2152. Rf=0.35 (silica, DCM-MeOH, 95:5).

Compound 59c: anhydrous THF (10 mL) was added to the brominated derivative 14c (142 mg, 0.4 mmol) and the solution was degassed by three freeze-thaw cycles. To this solution were added acetylenic derivative (147 mg, 0.4 mmol) and TEA (5 mL) and the solution was degassed again. To this solution were added Pd(PPh$_3$)$_4$ (46 mg, 0.04 mmol) and CuI (7.6 mg, 0.04 mmol). This new solution was degassed again three times and then stirred at 65° C. in an inert atmosphere. The progress of the reaction was monitored by TLC. After 1 hour the reaction was complete. The reaction mixture was cooled to RT and the solvent was removed under reduced pressure. The residue was diluted in DCM (25 mL) and washed with a saturated aqueous solution of ammonium chloride (25 mL) and then with water (25 mL). The organic phase was dried over MgSO$_4$, filtered and concentrated under reduced pressure to produce a residue that was purified by silica column chromatography (DCM/MeOH 0 to 3% in 0.5% increments) to obtain a yellow oil corresponding to compound 59c (154 mg, 70%). $^1$H NMR (400 MHz, CDCl$_3$) δ: 8.01 (dd, J=6.4; 2.0 Hz, 1H), 7.89 (dd, J=8.4; 12.4 Hz, 2H), 7.48 (t, J=8.4 Hz, 1H), 7.40 (d, J=8.8 Hz, 2H), 7.39 (td, J=8.4; 4.2 Hz, 2H), 7.33 (d, J=2.0 Hz, 1H), 6.81 (d, J=8.8 Hz, 2H), 4.73 (s, 1H), 4.69 (s, 2H), 4.08 (qd, J=5.6; 4.8 Hz, 2H), 3.97 (t, J=6 Hz, 2H), 3.26 (m, 2H), 1.92 (q, J=6 Hz, 2H), 1.37 (s, 9H), 1.31 (t, J=5.6 Hz, 3H); $^{13}$C NMR (100 MHz, CDCl$_3$) δ: 160.3 (d, J=18 Hz), 159.8; 156.0; 153.2 (d, J=164 Hz); 133.7; 133.0 (d, J=11 Hz); 132.6 (d, J=5 Hz); 132.3 (d, J=10 Hz); 129.6 (d, J=138 Hz); 128.6 (d, J=18 Hz); 128.5 (d, J=9 Hz); 123.8 (d, J=3 Hz); 114.7; 113.8; 96.0; 85.3 (d, J=2 Hz); 79.3; 65.9; 63.8; 61.9 (d, J=6 Hz); 37.9; 29.5; 28.4; 16.6; $^{31}$P NMR (162 MHz, CDCl$_3$) δ: +25.6. HRMS (ESI+) calculated for C$_{30}$H$_{36}$N$_2$O$_6$P [M+H]$^+$, m/z 551.2306 found: 551.2305. Rf=0.24 (silica, DCM-MeOH, 95:5).

Compound 60a: to a solution of alcohol 59a (195 mg, 0.44 mmol) in anhydrous THF (7 mL), TEA (0.2 mL, 148 μmol) was added dropwise under inert atmosphere. To this mixture, cooled to 4° C., MsCl (67 μL, 0.84 mmol) was added dropwise. The progress of the reaction was monitored by TLC. After 5 minutes, the reaction was complete. The solvent was removed under reduced pressure. The residue was dissolved in DCM (10 mL) and this solution was washed with water (2×10 mL). The organic phase was dried over MgSO$_4$, filtered and concentrated under reduced pressure to produce a yellow-green oil (240 mg, quantitative). The product 60a was pure enough to be used in the subsequent synthesis without further purification. LRMS (ESI+) calculated for C$_{25}$H$_{31}$N$_2$O$_8$S [M+H]$^+$, m/z 519.1801, found: 519.13. Rf=0.6 (silica, DCM-MeOH 96:4).

Compounds 60b-c: compounds 60b-c were prepared according to the same procedure as that used for the synthesis of 60a.

Compounds 61a-c: compounds 61a-c were prepared according to the same procedure as that used for the synthesis of 61d.

Compound 61d: to a solution of compound 1 (81 mg, 0.353 mmol) in anhydrous THF (10 mL), compound 17a (234 mg, 0.706 mmol) in solution in anhydrous MeCN (10 mL) and potassium carbonate (195 mg, 1.413 mmol) were added all at once. The reaction was stirred at 60° C. overnight. The progress of the reaction was monitored by UPLC-MS (gradient A). After this period, the reaction was complete. The reaction mixture was concentrated under reduced pressure, diluted in DCM (50 mL), washed with water (25 mL×2) and then water saturated with NaCl (25 mL). The organic phase was dried over MgSO$_4$, filtered and concentrated under reduced pressure. The crude product was purified by silica column chromatography using a DCM/MeOH solvent gradient of 96/4 to 90/10 to yield compound 61d (67 mg, 27%) in white powder form.

HPLC gradient A—Rt=2.91 min—[M+H]$^+$, m/z 700.54—HRMS (ESI+) calculated for C$_{35}$H$_{50}$N$_5$O$_{10}$$^+$ [M+H]$^+$, m/z 700.3552, found: 700.3560—$^1$H NMR (400 MHz, CDCl$_3$) δ: 7.85 (s, 2H), 7.69 (s, 1H), 7.57 (s, 1H), 4.00 (s, 3H, Py-COOMe), 3.97 (s, 10H), 3, (s, 3H, OMs), 3.66 (s, 6H), 3 (m, 20H), 1.45 (s, 9H); $^{13}$C NMR (100 MHz, CDCl$_3$) δ: 172.48; 172.39; 165.90; 161.48; 155.68; 151.13; 147.55; 147.43; 126.27; 123.70; 79.29; 63.56; 63.40; 57.15; 54.84; 54.66; 54.35; 52.88; 51.84; 51.80; 50.09; 49.50; 34.07; 33.93; 30.11; 30.06; 29.68; 28.56.

Compounds 61e-s: compounds 61e-s were prepared according to the same procedure as that used for the synthesis of 61d.

Compounds 62a-c: compounds 62a-c were prepared according to the same procedure as that used for the synthesis of 62d.

Compound 62d: in a 25 mL flask, compound 61d (67 mg, 0.096 mmol) was solubilized in DCM (500 µL) to give a colourless solution. TFA (500 µL, 6.53 mmol) was added to the reaction mixture all at once. The reaction was stirred at RT for 30 minutes. The progress of the reaction was monitored by UPLC-MS (gradient A). After this period, the reaction was complete. The reaction mixture was concentrated under reduced pressure to produce a white powder (57 mg) which was used in the subsequent procedure. In a 100 mL flask, compound 60a (76 mg, 0.147 mmol) and the white powder previously obtained from two combined batches (87.4 mg, 0.122 mmol) were solubilized in anhydrous MeCN (30 mL) to give a colourless solution. Potassium carbonate (16.92 mg, 0.122 mmol) was added to the reaction mixture all at once. The reaction was stirred at 65° C. overnight. The progress of the reaction was monitored by UPLC-MS (gradient A), after this period, the reaction was complete. The reaction mixture was concentrated under reduced pressure, diluted in DCM (50 mL), washed with water (2×40 mL). The organic phase was dried over MgSO$_4$, filtered and concentrated under reduced pressure to yield compound 62d (10.8 mg, 10.6 µmol, 9%) in white powder form. HPLC gradient A—Rt=2.91 min—[M+H]$^+$, m/z 1022.65—HRMS (ESI+) calculated for C$_{54}$H$_{67}$N$_7$O$_{13}$Ag$^+$ [M+Ag]$^+$, m/z 1128.3842, found: 1128.3843.

Compounds 62e-s: compounds 62e-s were prepared according to the same procedure as that used for the synthesis of 62d.

Compounds 64a-c: compounds 64a-c were prepared according to the same procedure as that used for the synthesis of 64d.

Compound 64d: in a 50 mL flask, compound 62d (10.8 mg, 10.57 µmol) was solubilized in water (4 mL) to give a colourless suspension. LiOH (1.291 mg, 0.053 mmol) was added to the reaction mixture all at once. The reaction was stirred at RT for 1 hour. The progress of the reaction was monitored by UPLC-MS (gradient A). After this period, the deprotection was complete. The pH of the reaction mixture was adjusted to 7 with 1 M HCl. To the reaction mixture (compound 63d) europium chloride hexahydrate (5.81 mg, 15.85 µmol) was added all at once. The reaction was stirred at room temperature for 1 hour, after this period the reaction was complete. The reaction mixture was directly purified by preparative HPLC (gradient B) and led to compound 64d (6.32 mg, 5.74 µmol, 54%) in white powder form. HPLC gradient A—Rt=2.62 min—[M-2H]$^+$, m/z 1102.62—HRMS (ESI+) calculated for C$_{49}$H$_{55}$EuNO$_{13}$$^+$ [M-2H]$^+$, m/z 1100.3051, found: 1100.3064.

Compounds 64e-s: compounds 64e-s were prepared according to the same procedure as that used for the synthesis of 64d.

Complex 65d-E$_2$: in a 25 mL flask, compound 64d (6.32 mg, 5.74 µmol) was solubilized in anhydrous DMSO (1 mL) to give a colourless solution. To the reaction mixture was added 3-amino-1-propanesulphonic acid (3.29 mg, 22.96 µmol), DIPEA (4 µL, 23 µmol) and HATU (6.75 mg, 17.2 µmol) all at once. The reaction was stirred at RT for 15 minutes. The progress of the reaction was monitored by UPLC-MS (gradient C), after this period, the reaction was complete. The reaction mixture was directly purified by preparative HPLC (gradient D) and led to the soluble complex 65d-E$_2$ (5.87 mg, 4.37 µmol, 76%) in white powder form. HPLC gradient C—Rt=2.19 min—[M-2H]$^+$, m/z 1345.26—HRMS (ESI+) calculated for C$_{55}$H$_{70}$EuN$_9$O$_{17}$S$_2$$^{2+}$ [M–H]$^{2+}$, m/z 672.6768, found: 672.6769.

Complex 66d-E$_2$: in a 25 mL flask, complex 65d-E$_2$ (5.64 mg, 4.2 µmol) was solubilized in TFA (200 µL) to give a yellow solution. The reaction was stirred at RT for 30 minutes. The progress of the reaction was monitored by UPLC-MS (gradient C). After this period, the deprotection was complete. The reaction mixture was concentrated under reduced pressure and purified by preparative HPLC (gradient E) and led to complex 66d-E$_2$ (2.16 µmol, 51%) in white powder form. HPLC gradient C—Rt=1.36 min—[M-2H]$^+$, m/z 1243.45—HRMS (ESI+) calculated for C$_{50}$H$_{62}$EuN$_9$O$_{15}$S$_2$$^{2+}$ [M–H]$^{2+}$, m/z 622.6506, found: 622.6503.

Figure 2:
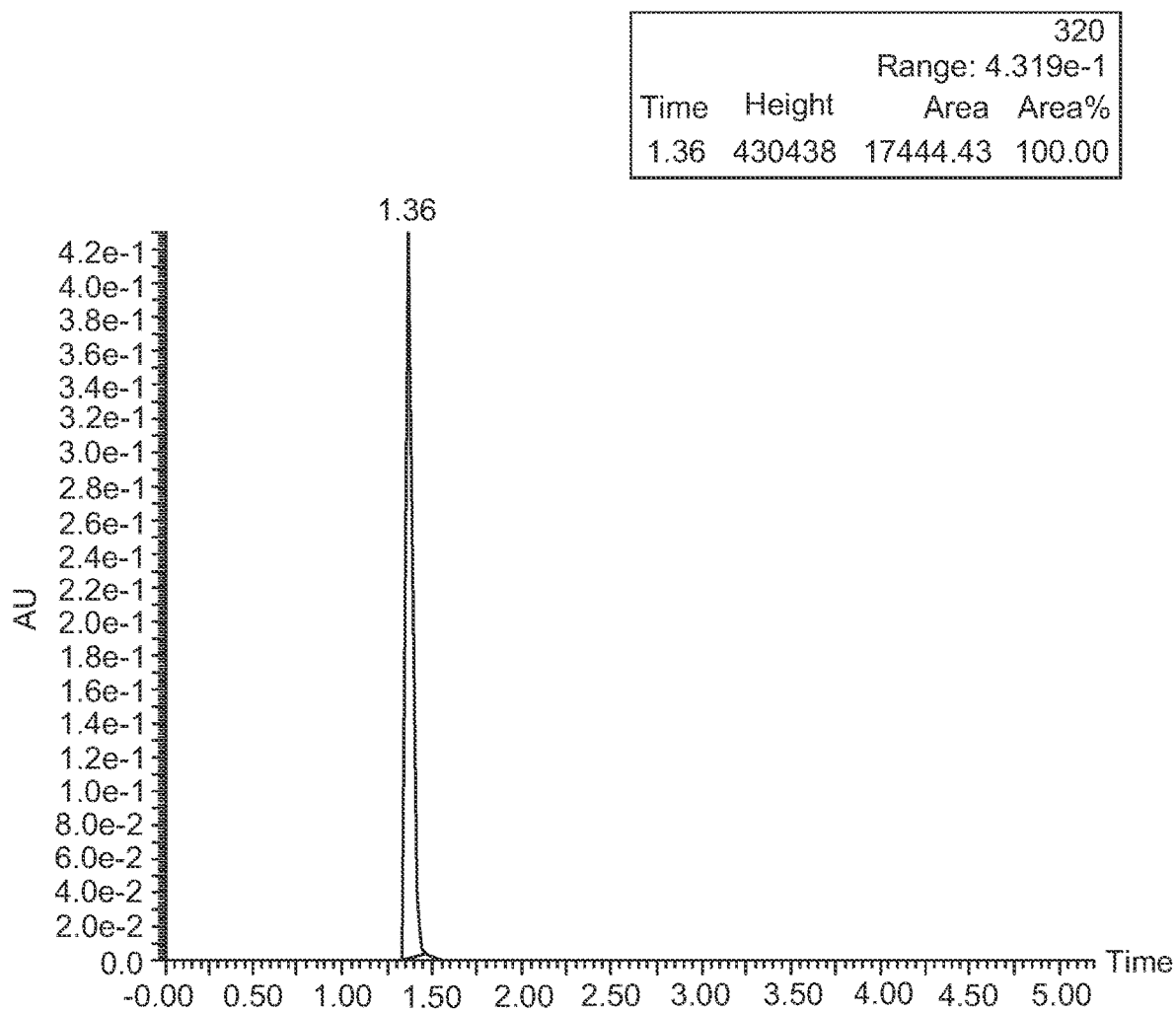
Figure 3:
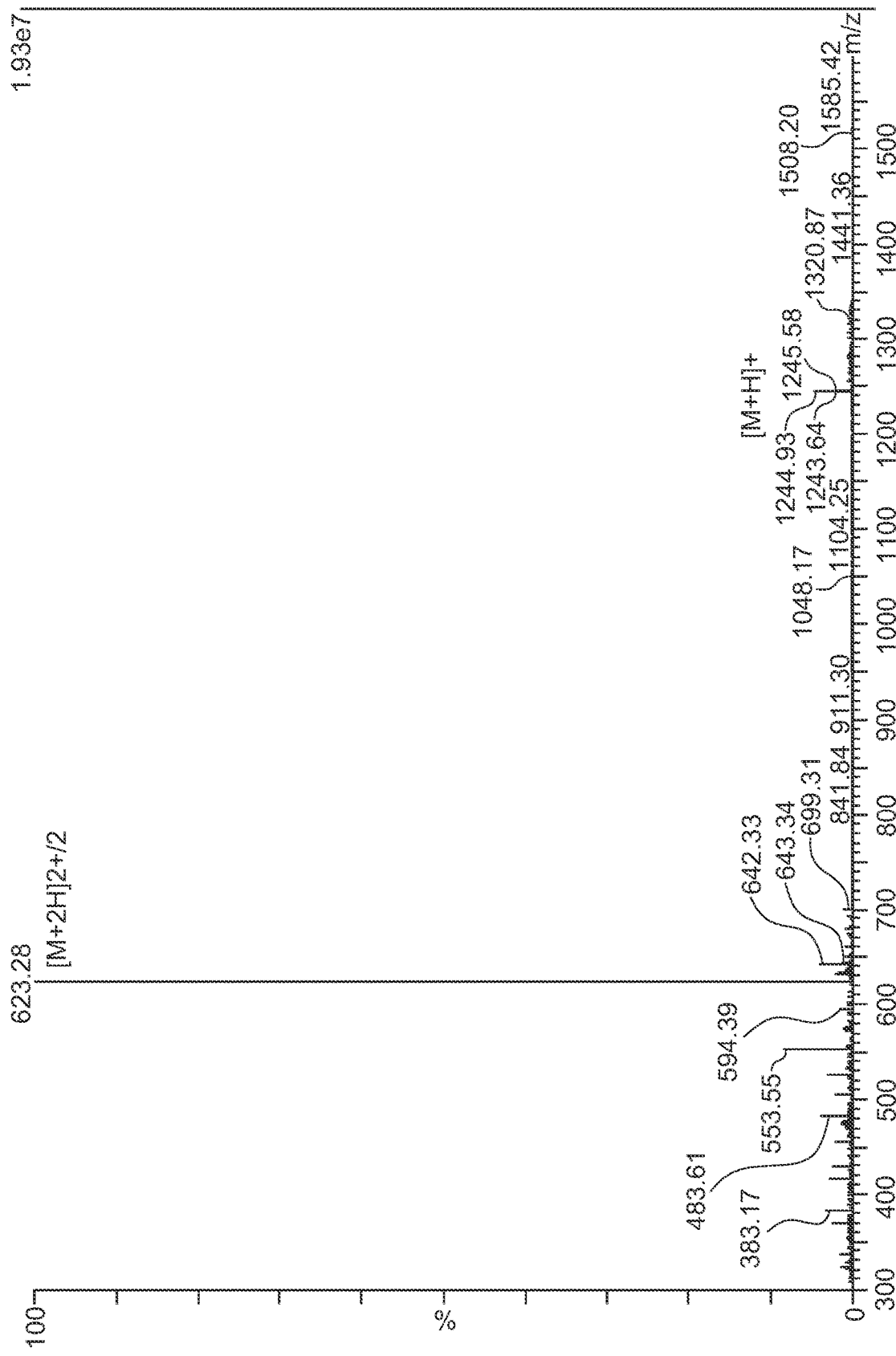

The UV spectrum, chromatogram and mass spectrum of complex 66d-E2 are shown in FIGS. 1 to 3 respectively.

We have determined the photophysical properties of complex 66d-E2 and of the three-antenna complexes (TACN-Phos-triantenna and TACN-Carbo-triantenna), synthesized as described in application WO 2014/111661, and whose structure is shown below.

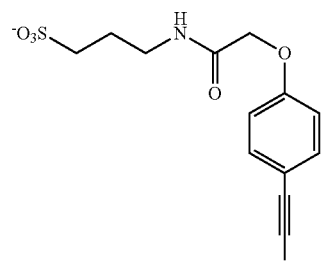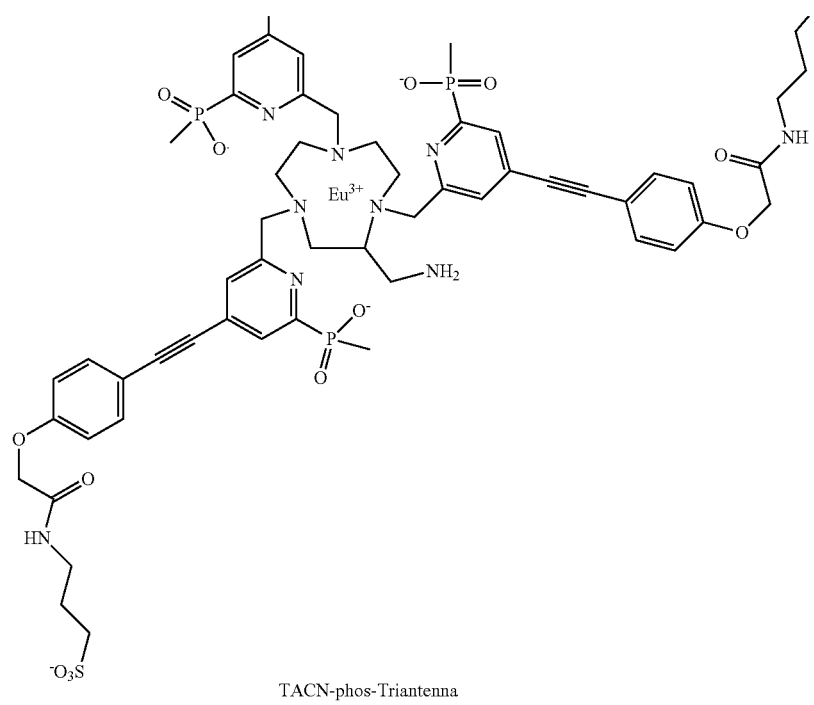
TACN-phos-Triantenna
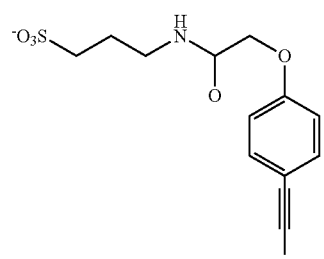

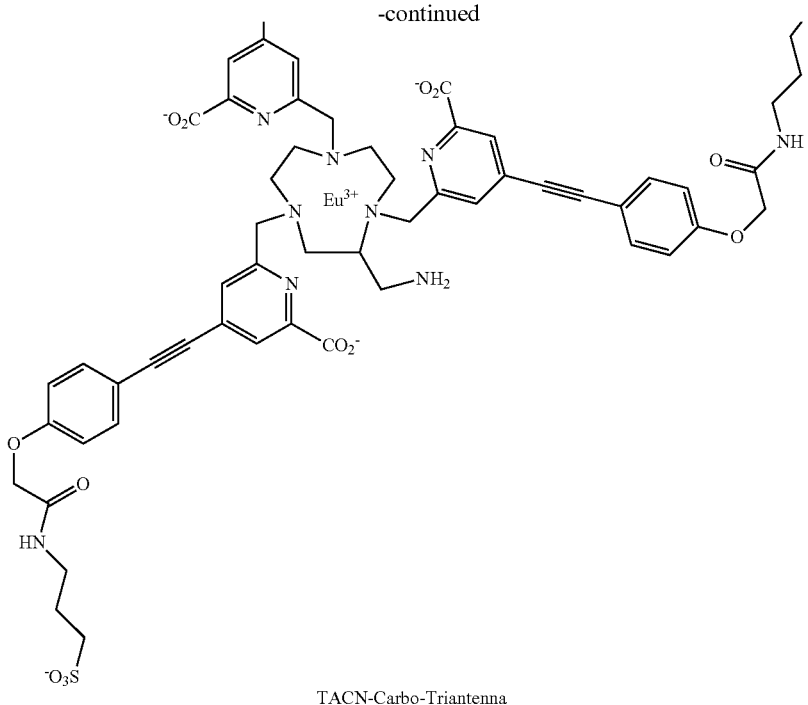

TACN-Carbo-Triantenna

As can be seen from the table below, the brightness of complex 66d-E2 is lower than that of the TACN-Phos-triantenna and TACN-Carbo-triantenna complexes with three antennae.

| Complex | Max. absorption (nm) | Brightness | Lifetime (ms) |
|---|---|---|---|
| 66d-E2 | 334 | 4800 | 0.93 |
| TACN-Phos-Triantenna | 328 | 15000 | 1.04 |
| TACN-Carbo-Triantenna | 337 | 11400 | 0.8 |

The efficiency of the 66d-E2 and TACN-Phos-triantenna complexes was also tested according to the following protocol. Each of the complexes was functionalized as an NHS ester (N-hydroxysuccinimide) using conventional techniques known to the skilled person. A batch of anti-glutathione S-transferase (anti-GST) antibodies was labelled using either the 66d-E2-NHS complex or the TACN-Phos triantenna-NHS complex. The average number of antibody-bound complexes is 7, both with the TACN-Phos triantenna complex (AntiGST-TACN-Phos-triantenna) and with complex 66d-E2 (AntiGST-66d-E2).

Figure 4:
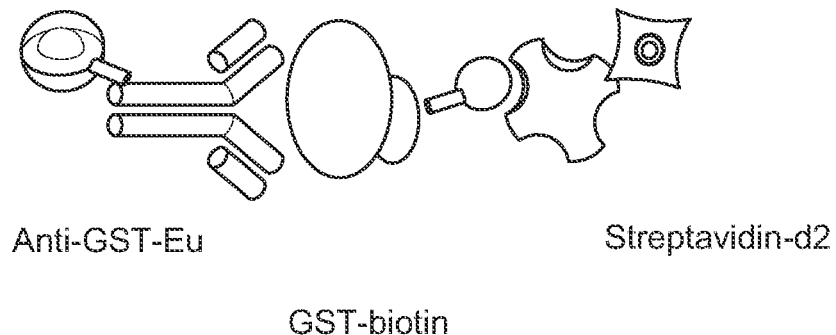
FIG. 4 schematically represents an immunoassay used to test the effectiveness of a complex representative of the invention.
Figure 5:
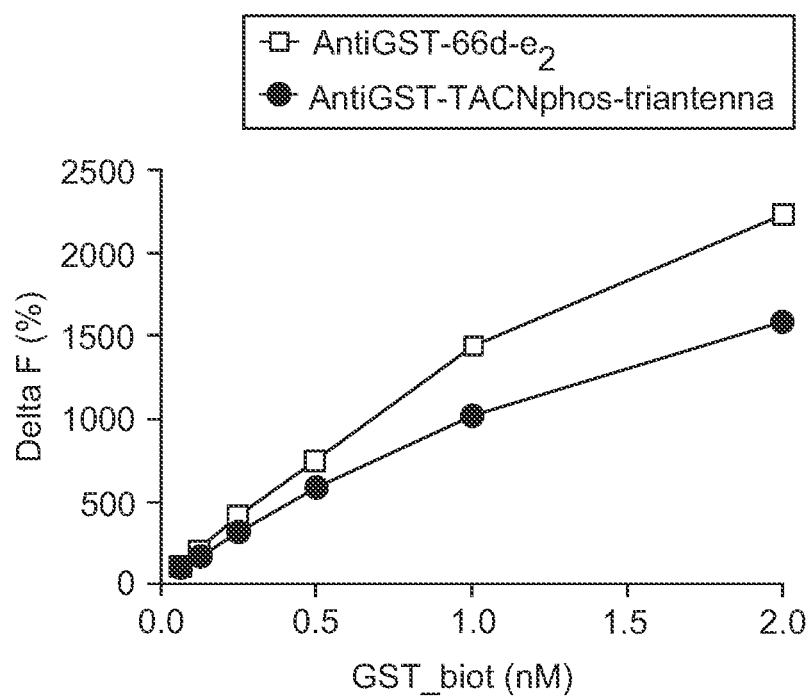
FIG. 5 represents the FRET signal (Delta F) measured during the implementation of the immunoassay in FIG. 4.

Anti-GST antibodies labelled with the europium complex 66d-E2 (AntiGST-66d-E2) or with the europium TACN-Phos-triantenna complex (AntiGST-TACN Phos-triantenna) were used in an immunoassay (shown in FIG. 4) based on time-resolved fluorescence to detect the glutathione S-transferase-biotin (GST-biotin) protein. A range of concentrations of GST-biotin diluted in phosphate buffer containing BSA was measured in the presence of a defined concentration of anti-GST-66d-E2 or anti-GST-TACN Phos-triantenna and of 5 nm of streptavidin-d2 (Cisbio Bioassays prod No. 610SADLB) in a 384-well plate in triplicate and read in HTRF mode on a Pherastar FS fluorescence reader (BMG-labtech) after 2 hours of incubation. The results are shown in FIG. 5. With the two labelled antibodies, GST-biotin is detected. Surprisingly and unexpectedly, the performance of the immunoassay using the AntiGST-66d-E2 antibody is superior to that of the AntiGST-TACN phos-triantenna, i.e. the single antenna fluorescent probe has a higher FRET capacity than the one with three antennae, despite a brightness three times lower.

To confirm this result, another immunoassay was performed using an antibody that recognizes cyclic adenosine monophosphate (cAMP). For this purpose the anti-cAMP antibody was labelled with the 66d-E2-NHS complex leading to the anti-cAMP-66d-E2 conjugate carrying on average 6.5 complexes/antibody. The same batch of antibodies was labelled with the TACN-Carbo-triantenna NHS complex leading to the anti-cAMP-TACN-Carbo-triantenna conjugate carrying an average of 6.6 complexes/antibody.

Figure 6:
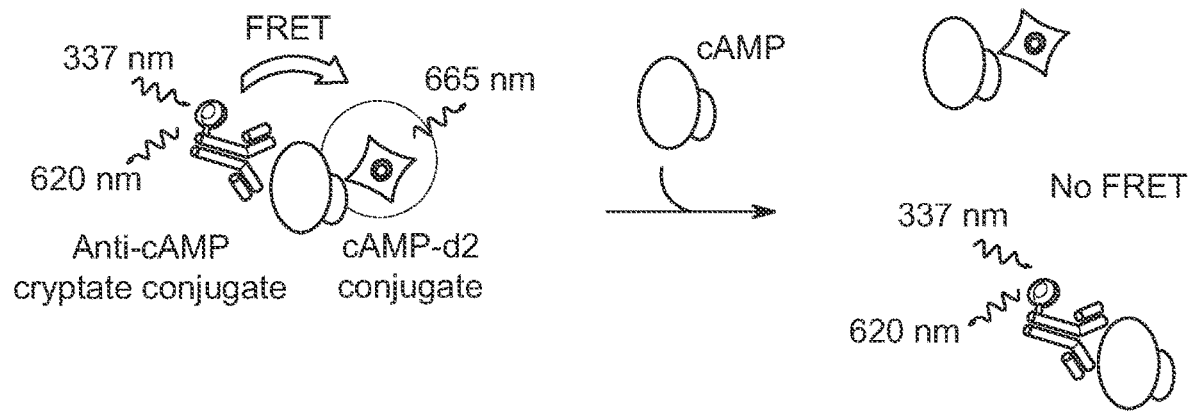
FIG. 6 schematically represents an immunoassay used to test the effectiveness of a complex representative of the invention.

The principle of the test is described in FIG. 6. Both conjugates were used in a competitive test using time-resolved fluorescence as a detection technique. The anti-cAMP labelled with a europium complex recognizes the cAMP conjugated with the fluorophore d2 (cAMP, Gs-dynamic kit, Cisbio Bioassays (ref 621M4PEC)) by giving a time-resolved fluorescence signal. A range of cAMP concentration allows the cAMP-d2 to be displaced, leading to a gradual decrease in the signal.

Figure 7:
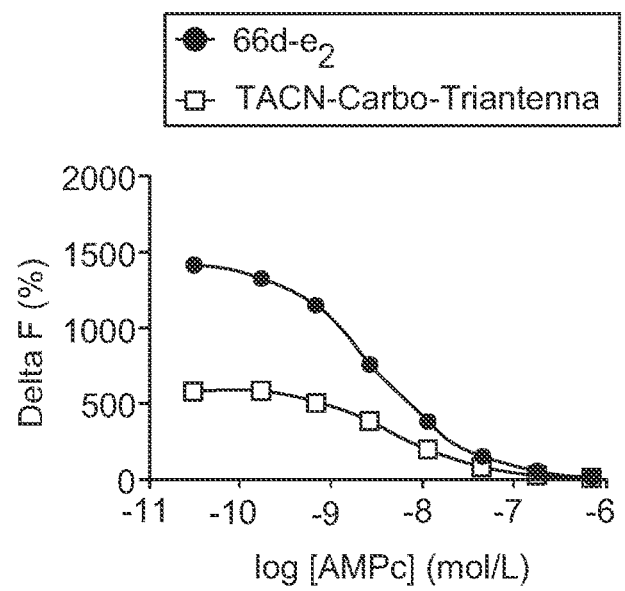
FIG. 7 represents the FRET signal (Delta F) measured during the implementation of the immunoassay in FIG. 6.

The two anti-cAMP-66d-E2 and anti-cAMP-TACN-Carbo-triantenna conjugates were used at a well-defined concentration in the presence of cAMP-d2 in a phosphate buffer in the presence of bovine serum albumin (BSA) by making a range of cAMP concentrations in a 384-well plate in triplicate and read in HTRF mode on a Pherastar FS plate reader (BMG-labtech) after 1 hour of incubation. The FRET signal inhibition response is shown in FIG. 7. In this second example, and again surprisingly, the performance of the anti-cAMP-66d-E2 conjugate is superior to that of the anti-cAMP-TACN-Carbo-triantenna conjugate, i.e. the single-antenna fluorescent probe has a higher FRET capacity than the one with three antennae, despite half the brightness.

Complexing agents consisting of a TACN macrocycle, bearing one or two phenylethynylpyridine chromophores, form stable complexes with lanthanides, and can be used to produce fluorescent conjugates of molecules of interest. The lanthanide complexes according to the invention have excellent photophysical properties, in particular with regard to their quantum yield, their luminescence lifetime and their excitation spectrum which is very well suited to laser excitation at about 337 nm. In addition, the distribution of the bands of their emission spectra is centred around 620 nm, thus giving the complexes exceptional and very favourable properties when using FRET with cyanine or allophycocyanin-type acceptors (such as XL665 marketed by Cisbio Bioassays). Due to the high stability of these complexes in biological media containing most of the divalent cations ($Ca^{2+}$, $Mg^{2+}$, etc.) or EDTA, their luminescence remains excellent.

The invention claimed is:

1. A lanthanide complex consisting of a complexing agent of formula (I) and a lanthanide:

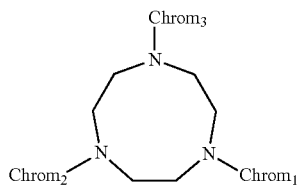

(I)

wherein:

$Chrom_1$, $Chrom_2$ and $Chrom_3$, independently of one another, represent a group of formula:

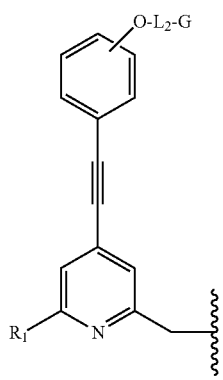

(Ia)

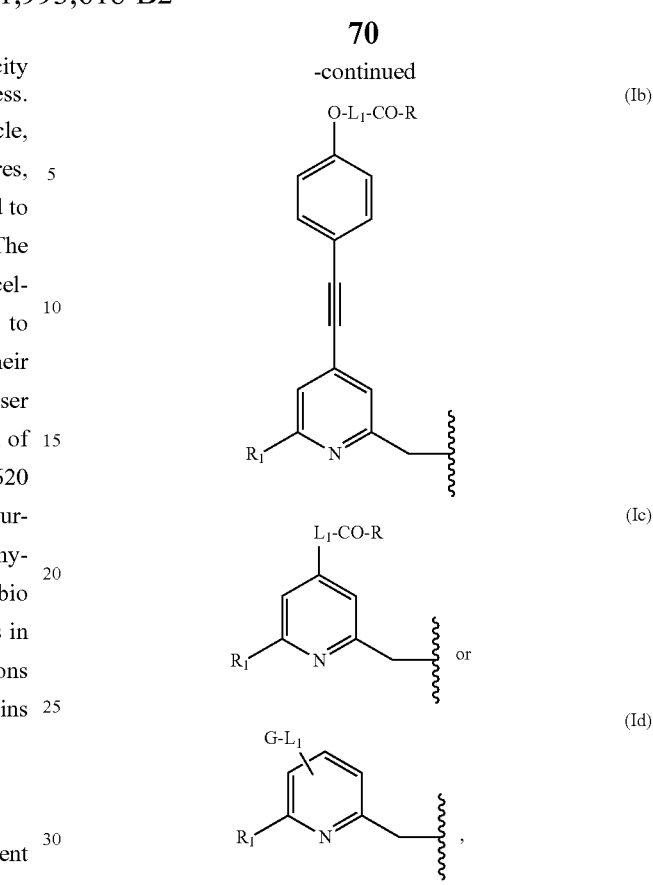

provided that the compound of formula (I) comprises (i) one or two groups selected from the groups (Ia) and (Ib) and (ii) at least one $L_1$-CO—R group;

R is a —$OR_2$ or —NH-E group;
$R_1$ is a —$CO_2H$ or —$P(O)(OH)R_3$ group;
$R_2$ is H or a ($C_1$-$C_4$)alkyl;
$R_3$ is a ($C_1$-$C_4$)alkyl; phenyl optionally substituted by a —$SO_3^-$ group; or benzyl;
$L_1$ is a direct bond; a —$(CH_2)_r$— group optionally interrupted by at least one atom selected from the group consisting of an oxygen atom, a nitrogen atom and a sulphur atom; a —CH=CH— group; a —CH=CH—$CH_2$— group; a —$CH_2$—CH=CH— group; or a PEG group of formula —$CH_2$—$(CH_2OCH_2)_y$—$CH_2OCH_3$, where y is an integer from 1 to 5;
$L_2$ is selected from the group consisting of:
a direct bond;
a linear or branched $C_1$-$C_{20}$ alkylene group, optionally containing one or more double or triple bonds;
a $C_5$-$C_8$ cycloalkylene group;
a $C_6$-$C_{14}$ arylene group;
said alkylene, cycloalkylene or arylene groups optionally containing one or more heteroatoms, or one or more carbamoyl or carboxamido groups, and said alkylene, cycloalkylene or arylene groups being optionally substituted by 1 to 5 $C_1$-$C_8$ alkyl, $C_6$-$C_{14}$ aryl, sulfonate or oxo groups; and
a divalent group of formula:

—$(CH2)_n$—;   —$(CH_2)_n$—O—$(CH_2)_m$—O—$(CH_2)_p$—;

—$(CH_2)_n$—O—$(CH_2)_m$—O—$(CH_2)_p$—NH—$\overset{O}{\underset{\|}{C}}$—$(CH_2)_q$—$\overset{O}{\underset{\|}{C}}$—;

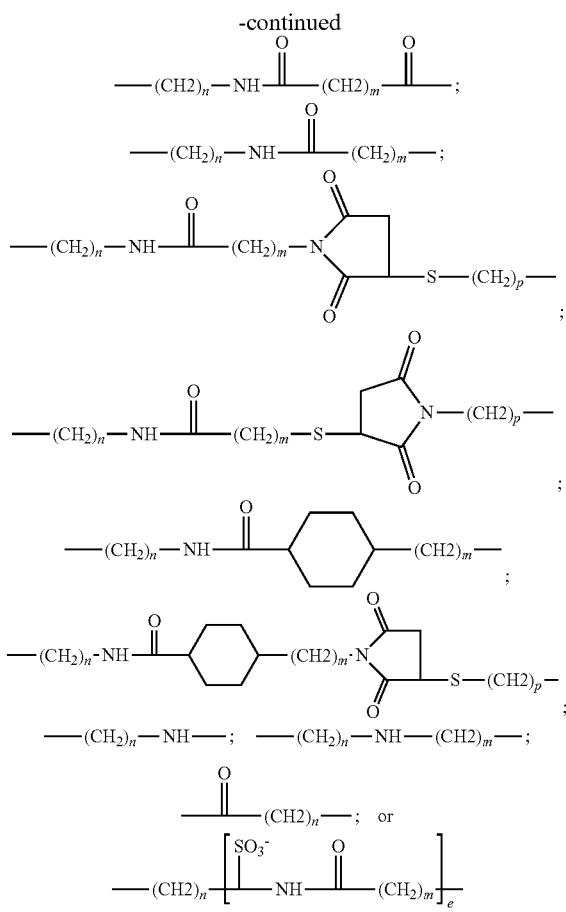

wherein n, m, p, q are integers from 1 to 16 and e is an integer from 1 to 6;

G is a reactive group selected from the group consisting of: an acrylamide, an activated ester, an aldehyde, an alkyl halide, an anhydride, an aniline, an azide, an aziridine, a carboxylic acid, a diazoalkane, a haloacetamide, a halotriazine, a hydrazine, an imido ester, an isocyanate, an isothiocyanate, a maleimide, a sulphonyl halide, a thiol, a ketone, an amine which is optionally activated, an acid halide, a succinimidyl ester, a hydroxysuccinimidyl ester, a hydroxysulfosuccinimidyl ester, an azidonitrophenyl, an azidophenyl, a 3-(2-pyridyldithio)-propionamide, a glyoxal, a triazine, and an acetylenic group;

E is a —$CH_2$—$(CH_2)_s$—$CH_2$—$SO_3$— or —$(CH_2)_s$—$N^m Alk_1 Alk_2 Alk_3$ group, or a sulfobetaine of formula

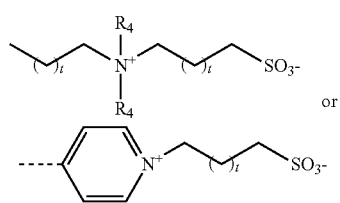

where $R_4$ represents a $(C_1$-$C_6)$alkyl, and t is equal to 1, 2, 3, 4, 5 or 6;

r is an integer from 1 to 6;

s is 0, 1 or 2;

$Alk_1$, $Alk_2$, $Alk_3$, which may be identical or different, represent a $(C_1$-$C_6)$alkyl.

2. The lanthanide complex according to claim 1, wherein the lanthanide is selected from the group consisting of: $Eu^{3+}$, $Sm^{3+}$, $Tb^{3+}$, $Gd^{3+}$, $Dy^{3+}$, $Nd^{3+}$, and $Er^{3+}$.

3. The lanthanide complex according to claim 2, wherein the lanthanide is $Eu^{3+}$ or $Tb^{3+}$.

4. The lanthanide complex according to claim 3, wherein the lanthanide is $Eu^{3+}$.

5. The lanthanide complex according to claim 1, wherein $Chrom_1$ is a group of formula (Ia) and $Chrom_2$ and $Chrom_3$ are each a group of formula (Ic), identical or different.

6. The lanthanide complex according to claim 5, wherein $Chrom_2$ and $Chrom_3$ are identical.

7. The lanthanide complex according to claim 1, wherein $Chrom_1$ and $Chrom_2$ are each a group of formula (Ib), identical or different, and $Chrom_3$ is a group of formula (Id).

8. The lanthanide complex according to claim 7, wherein $Chrom_1$ and $Chrom_2$ are identical.

9. The lanthanide complex according to claim 1, wherein $R_1$ is a —$CO_2H$ or —$P(O)(OH)R_3$ group wherein $R_3$ is a $(C_1$-$C_4)$alkyl or phenyl.

10. The lanthanide complex according to claim 1, wherein $L_1$ is a direct bond; a —$(CH_2)_r$— group optionally interrupted by at least one atom selected from an oxygen atom and a sulphur atom, and r=2 or 3; a —CH=CH— group; a —CH=CH—$CH_2$— group; or a —$CH_2$—CH=CH— group.

11. The lanthanide complex according to claim 1, wherein E is a —$CH_2$—$(CH_2)_s$—$CH_2$—$SO_3$— group with s=0 or 1; —$(CH_2)_s$—$N^+ Alk_1 Alk_2 Alk_3$ with $Alk_1$, $Alk_2$, $Alk_3$, identical or different, representing $(C_1$-$C_4)$alkyl and s=0 or 1; or a group of formula:

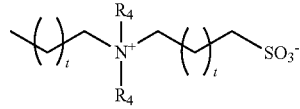

wherein $R_4$ is a $(C_1$-$C_4)$alkyl and t is 1 or 2.

12. The lanthanide complex according to claim 1, wherein the reactive group G is a group of formula:

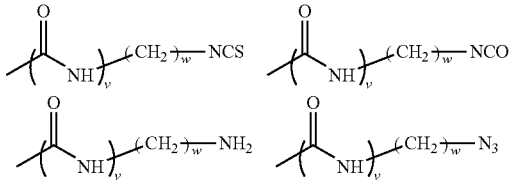

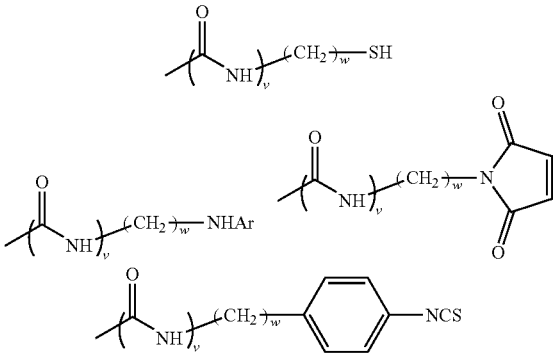

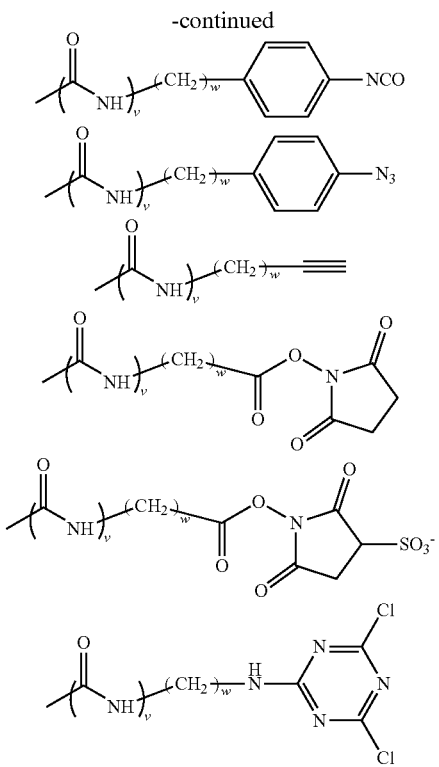

wherein w varies from 0 to 8 and v is equal to 0 or 1, and Ar is a saturated or unsaturated 5- or 6-membered heterocycle, comprising 1 to 3 heteroatoms, optionally substituted by a halogen atom.

13. The lanthanide complex according to claim 1, wherein the -$L_2$-G group consists of (i) a reactive group G selected from the group consisting of: a carboxylic acid, an amine, a succinimidyl ester, a haloacetamide, a hydrazine, an isothiocyanate, and a maleimide group, and (ii) a spacer arm $L_2$ consisting of an alkylene chain having from 1 to 5 carbon atoms or a group selected from groups of formula:

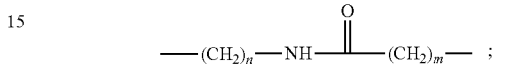

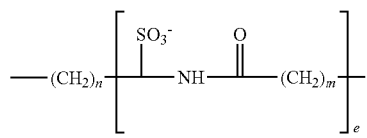

where n, m are integers from 1 to 16 and e is an integer from 1 to 6, the group G being linked to either end of these divalent groups.

* * * * *